(12) United States Patent
Wilson et al.

(10) Patent No.: US 11,648,070 B2
(45) Date of Patent: May 16, 2023

(54) REAL TIME IMAGE GUIDED PORTABLE ROBOTIC INTERVENTION SYSTEM

(71) Applicant: Mendaera, Inc., San Carlos, CA (US)

(72) Inventors: Jason Tomas Wilson, San Carlos, CA (US); Kevin Christopher Chu, San Carlos, CA (US); Benjamin Joseph Greer, Golden, CO (US); Alexander Tarek Hassan, San Francisco, CA (US); Joshua Francis DeFonzo, San Carlos, CA (US); Aren Calder Hill, Mountain View, CA (US); Erica Ding Chin, Mountain View, CA (US); Trent Michael Callan, San Francisco, CA (US)

(73) Assignee: Mendaera, Inc., San Carlos, CA (US)

( * ) Notice: Subject to any disclaimer, the term of this patent is extended or adjusted under 35 U.S.C. 154(b) by 0 days.

(21) Appl. No.: 17/860,970

(22) Filed: Jul. 8, 2022

(65) Prior Publication Data

US 2023/0008419 A1  Jan. 12, 2023

Related U.S. Application Data

(60) Provisional application No. 63/219,662, filed on Jul. 8, 2021.

(51) Int. Cl.
*G06F 17/00* (2019.01)
*A61B 34/30* (2016.01)
(Continued)

(52) U.S. Cl.
CPC ........ *A61B 34/30* (2016.02); *A61B 2034/107* (2016.02); *A61B 2034/2059* (2016.02); *A61B 2034/305* (2016.02); *A61B 2090/367* (2016.02)

(58) Field of Classification Search
CPC .............. A61B 34/30; A61B 2034/107; A61B 2034/2059; A61B 2034/305; A61B 2090/367
(Continued)

(56) References Cited

U.S. PATENT DOCUMENTS 10,898,286 B2 * 1/2021 Srinivasan ............. A61B 34/30
11,197,728 B2 * 12/2021 DeFonzo ............... A61B 34/25
(Continued)

FOREIGN PATENT DOCUMENTS

WO   WO 2017/220822 A1   12/2017
WO   WO 2019/148154 A1   8/2019

OTHER PUBLICATIONS

International Search Report and Written Opinion, PCT Application No. PCT/US2022/036576, International Filing Date Jul. 8, 2022, dated Oct. 14, 2022.

*Primary Examiner* — Ronnie M Mancho
(74) *Attorney, Agent, or Firm* — Kramer Levin Naftalis & Frankel LLP

(57) ABSTRACT

An image-guided robotic intervention system ("IGRIS") may be used to perform medical procedures on patients. IGRIS provides a real-time view of patient anatomy, as well as an intended target or targets for the procedures, software that allows a user to plan an approach or trajectory path using either the image or the robotic device, software that allows a user to convert a series of 2D images into a 3D volume, and localizes the 3D volume with respect to real-time images during the procedure. IGRIS may include sensors to estimate pose of the imaging device relative to the patient to improve the performance of that software with respect to runtime, robustness, and accuracy.

20 Claims, 48 Drawing Sheets

(51) Int. Cl.
 *A61B 90/00* (2016.01)
 *A61B 34/20* (2016.01)
 *A61B 34/10* (2016.01)
(58) Field of Classification Search
 USPC .......................................................... 700/245
 See application file for complete search history.

(56) References Cited

U.S. PATENT DOCUMENTS

| | | | |
|---|---|---|---|
| 11,376,083 B2 * | 7/2022 | Harris | A61B 46/40 |
| 11,399,906 B2 * | 8/2022 | Shelton, IV | B25J 9/1666 |
| 11,432,885 B2 * | 9/2022 | Shelton, IV | A61B 34/35 |
| 11,432,895 B2 * | 9/2022 | Loh | A61B 34/71 |
| 2019/0365209 A1 | 12/2019 | Ye | |
| 2020/0253670 A1 * | 8/2020 | Doisneau | A61B 17/221 |
| 2021/0093399 A1 * | 4/2021 | Hassan | A61B 34/71 |
| 2021/0137617 A1 * | 5/2021 | Srinivasan | A61B 34/20 |
| 2021/0298850 A1 * | 9/2021 | Huang | A61B 34/30 |
| 2022/0226059 A1 * | 7/2022 | Beckman | A61B 34/37 |

* cited by examiner

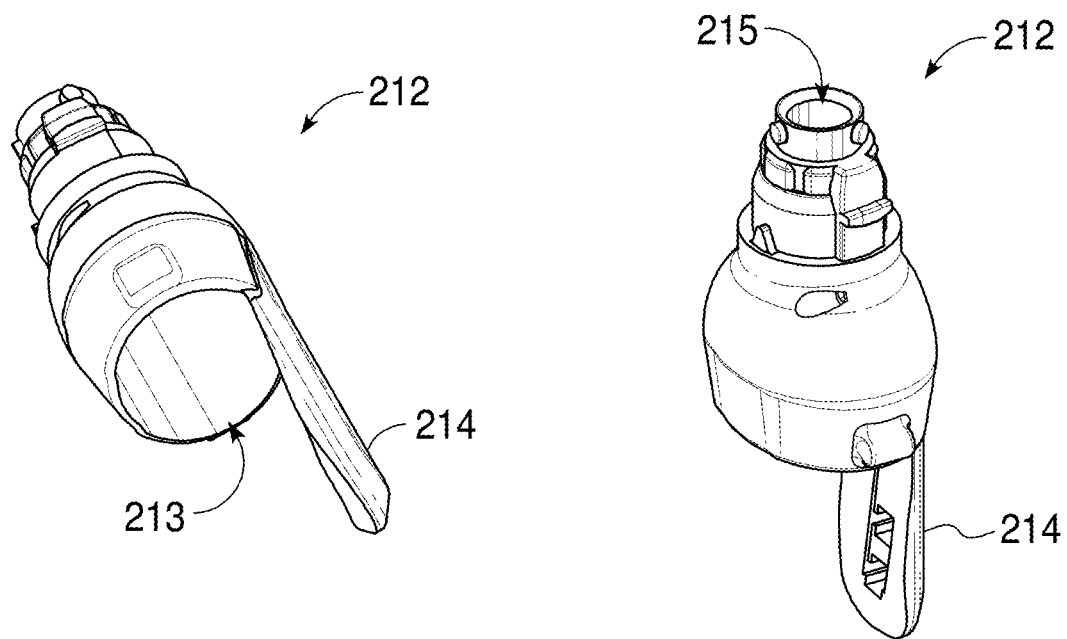
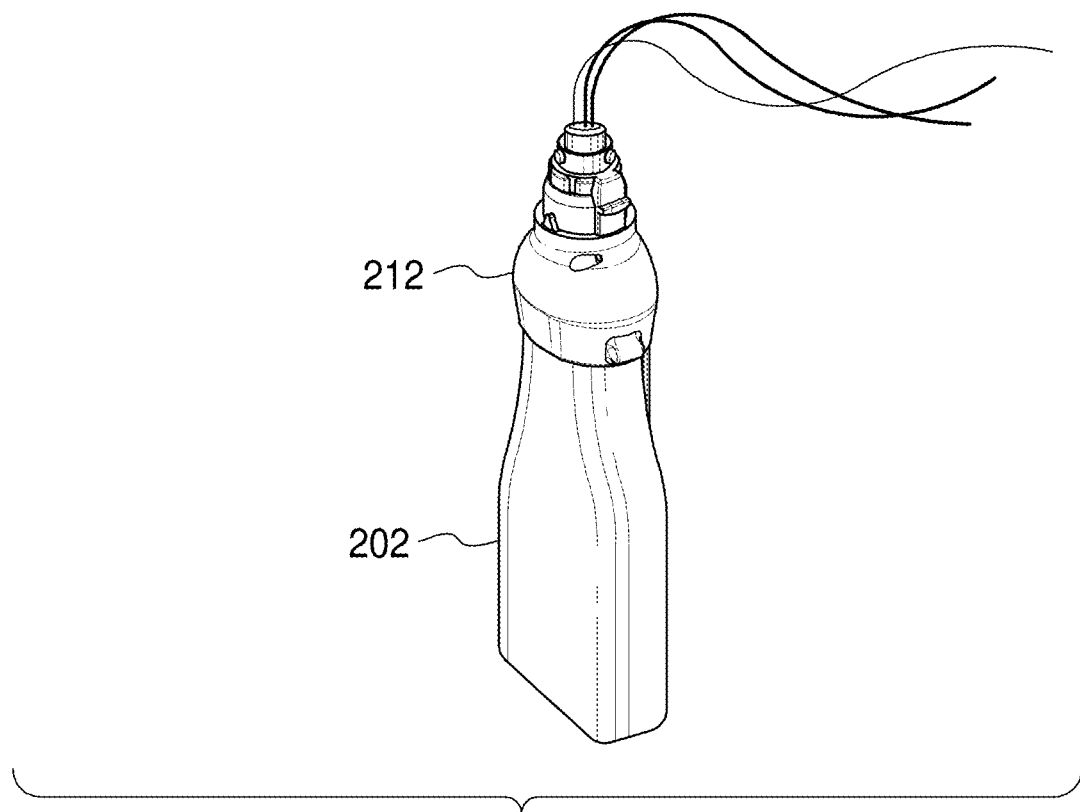
FIG. 2D

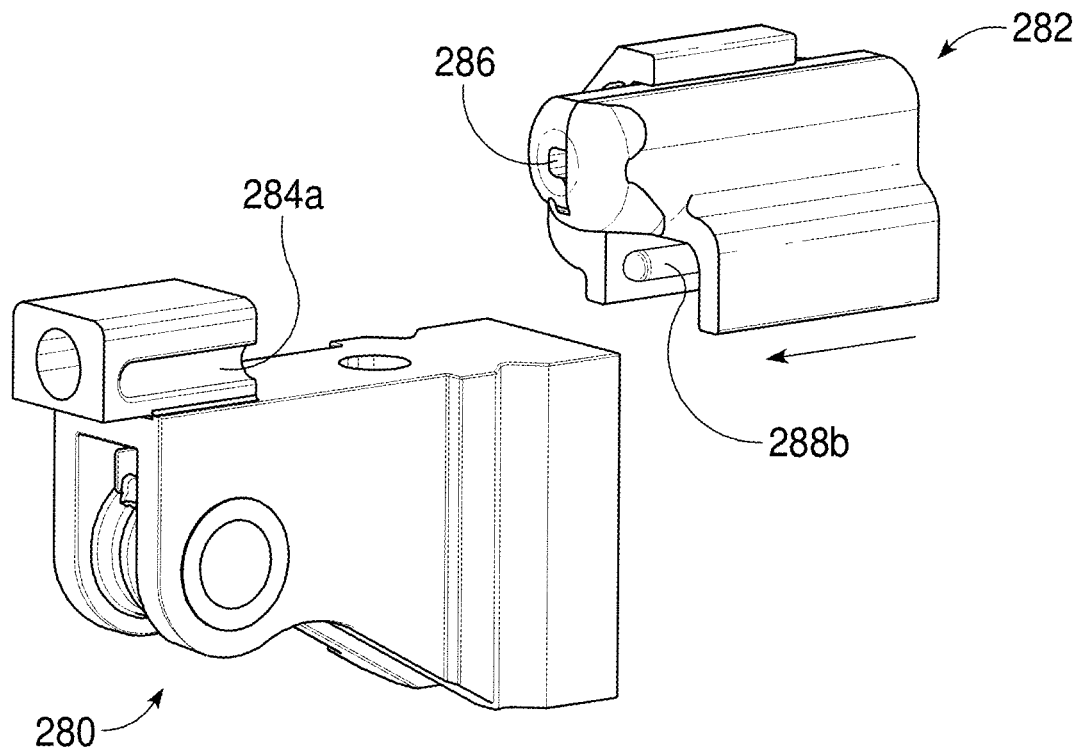
FIG. 2Q1
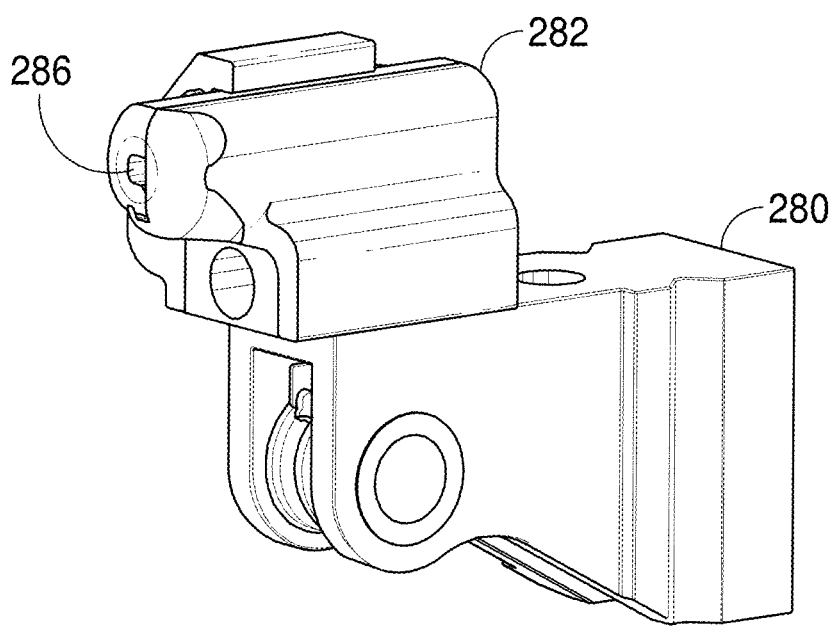
FIG. 2Q2

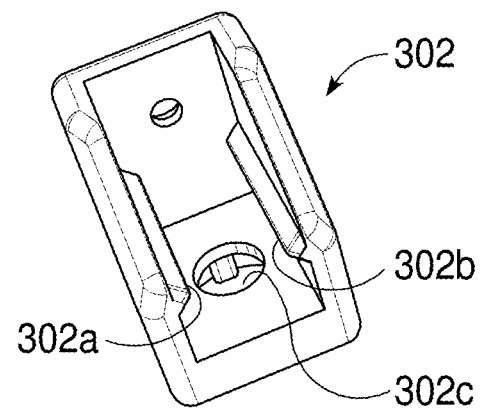
FIG. 2R1
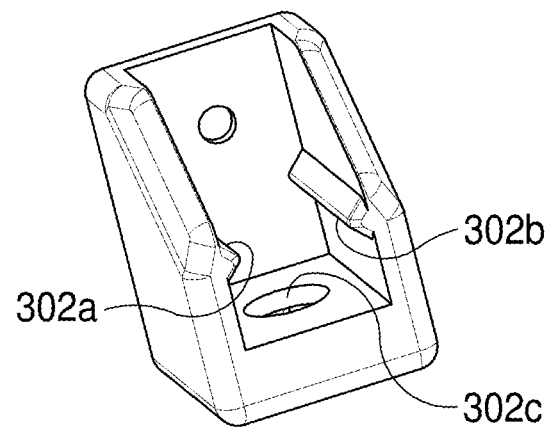
FIG. 2R2
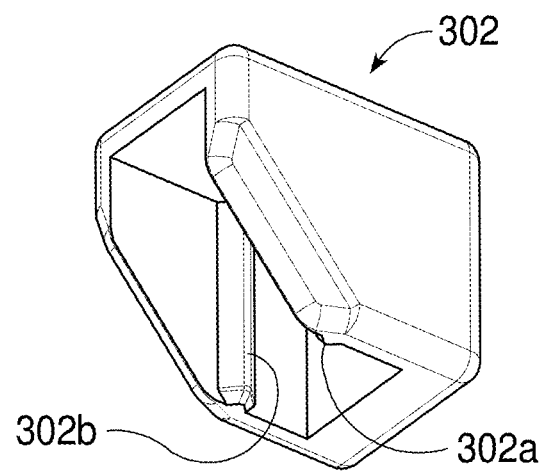
FIG. 2R3

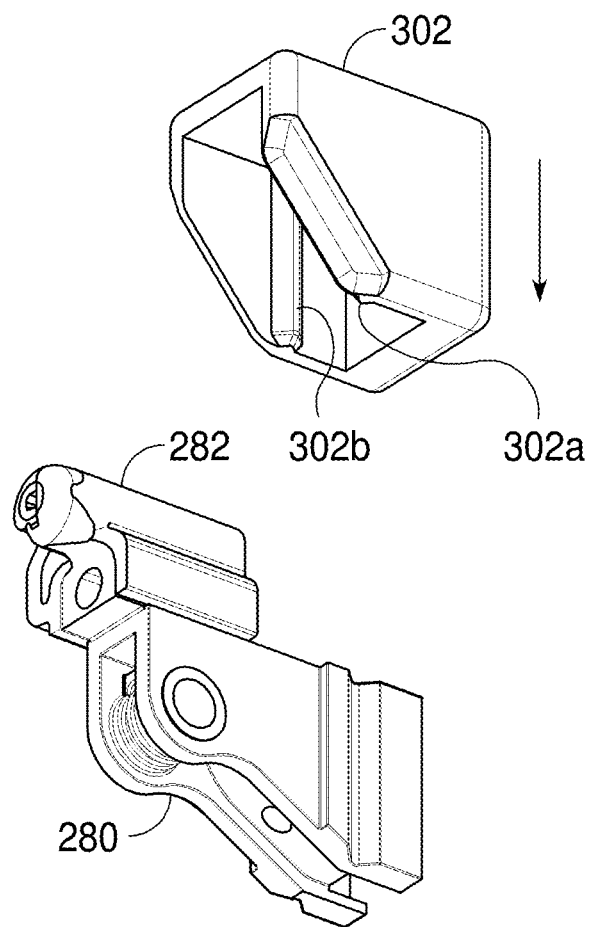
FIG. 2S1
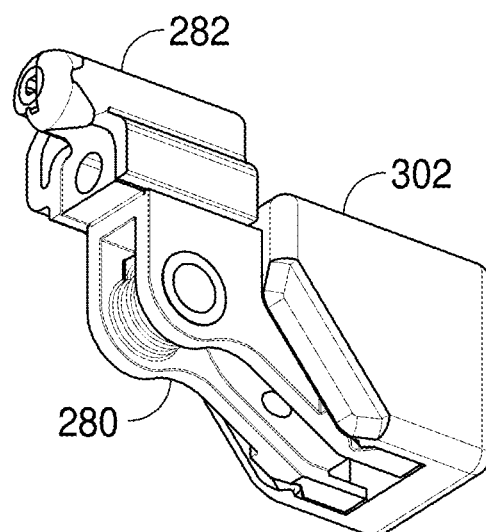
FIG. 2S2

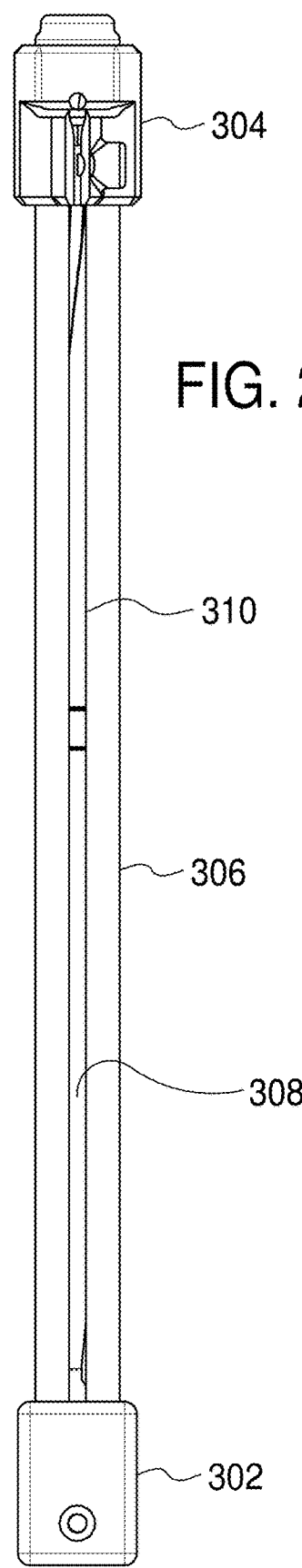
FIG. 2T1
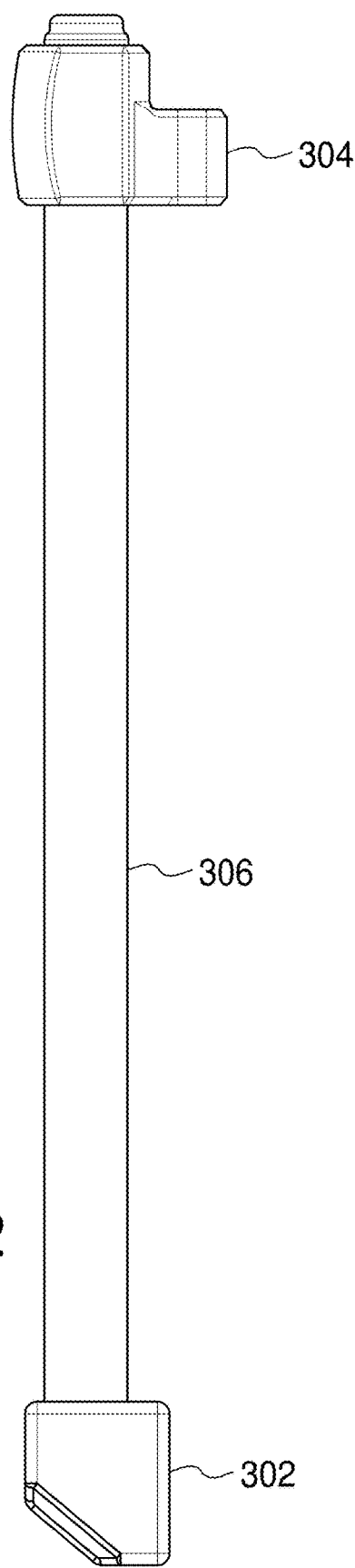
FIG. 2T2

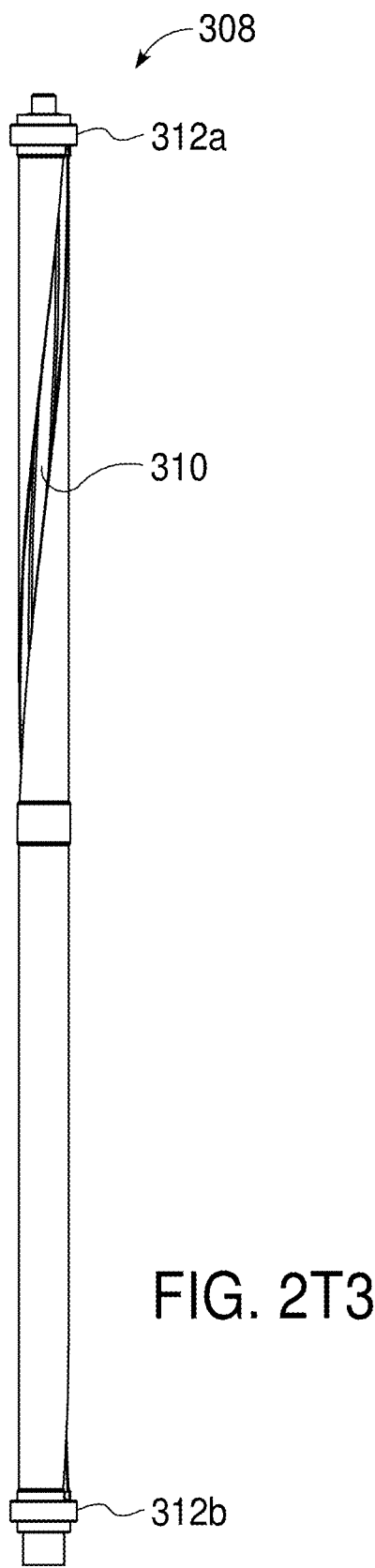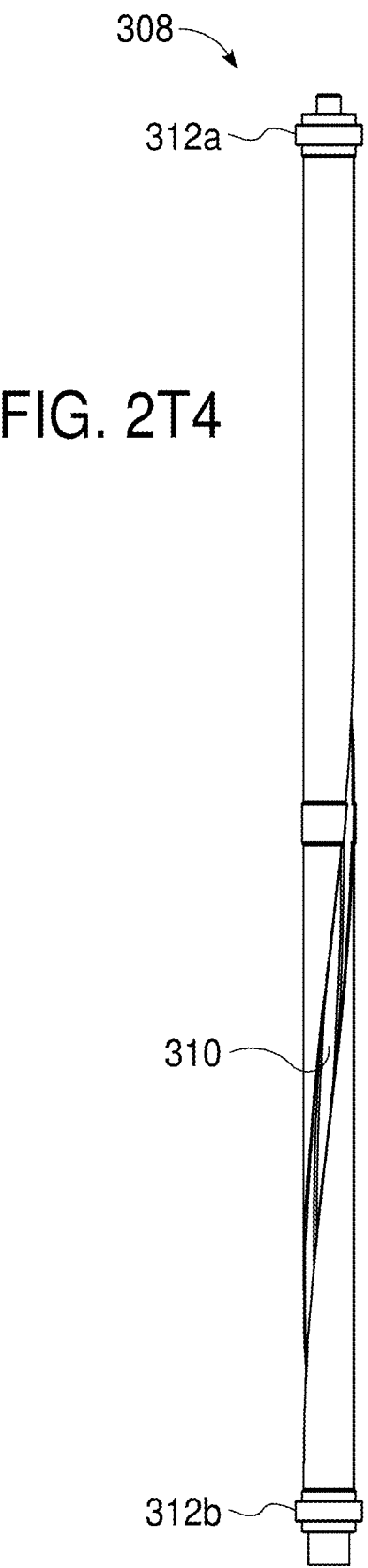
FIG. 2T3  FIG. 2T4

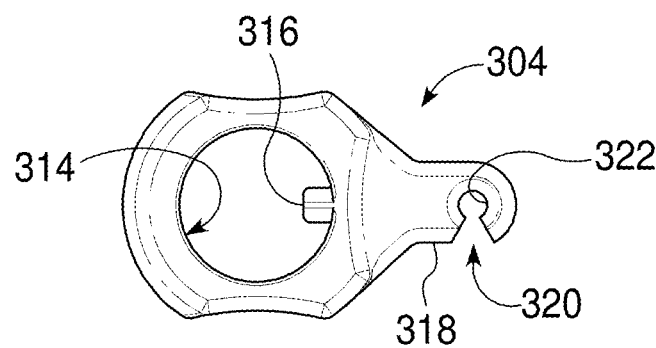
FIG. 2U1
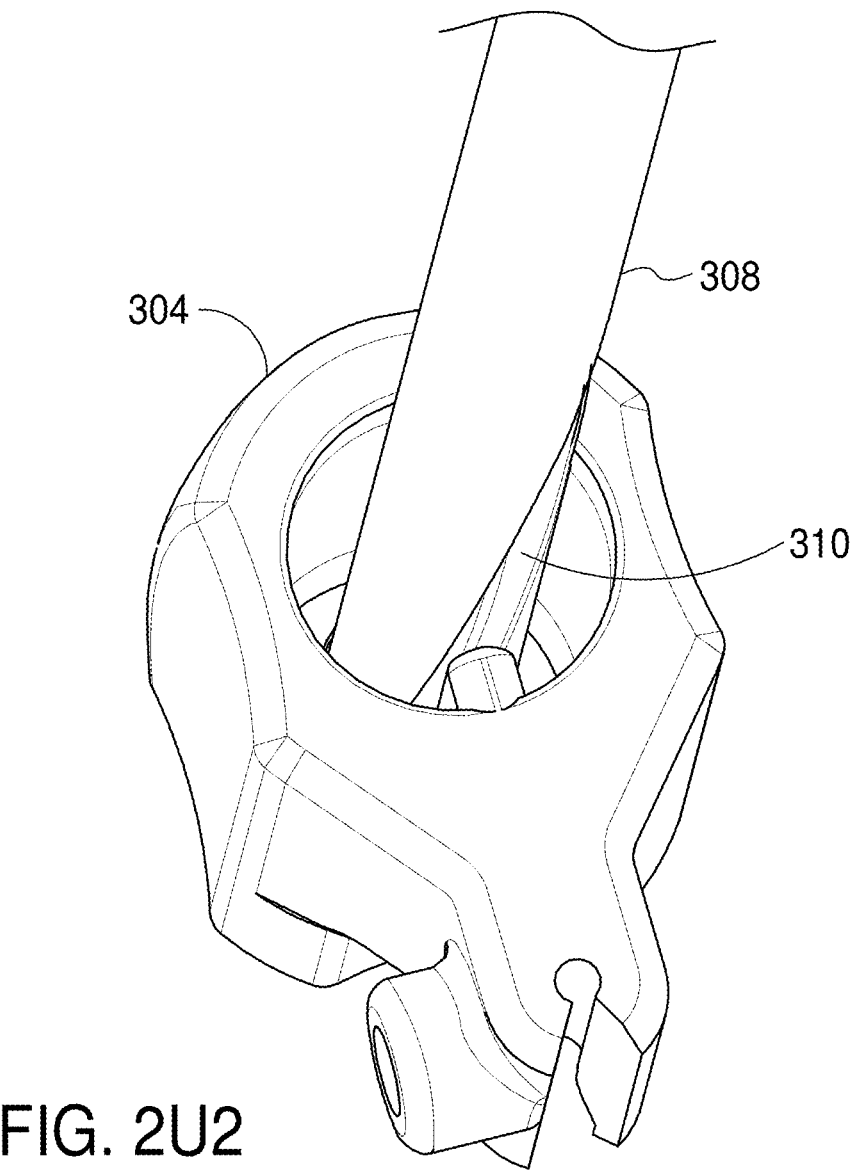
FIG. 2U2

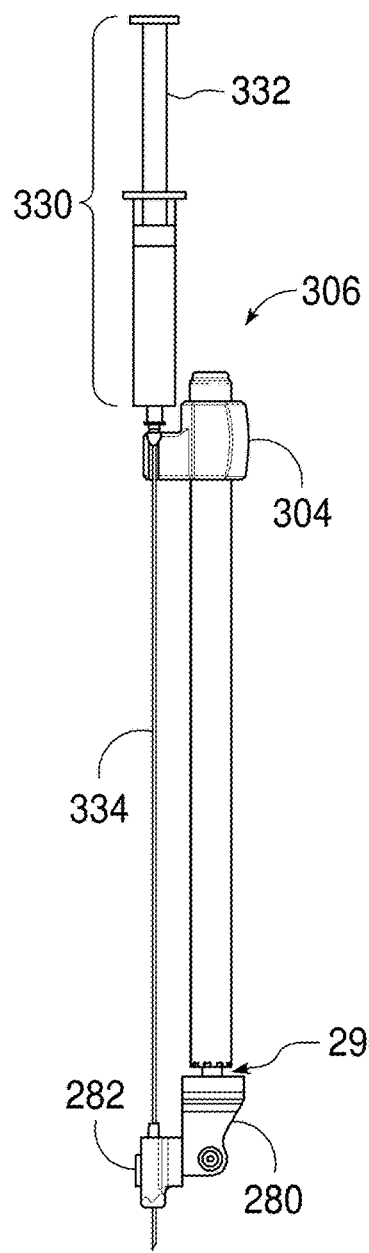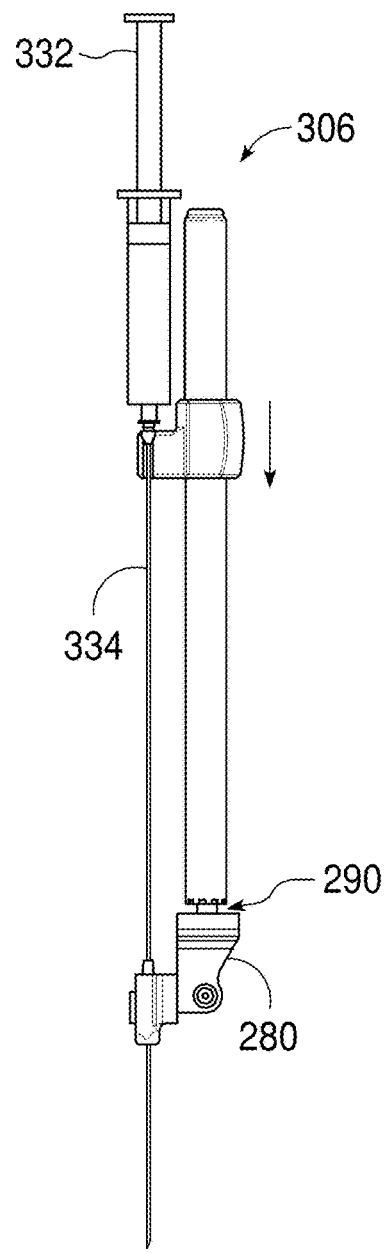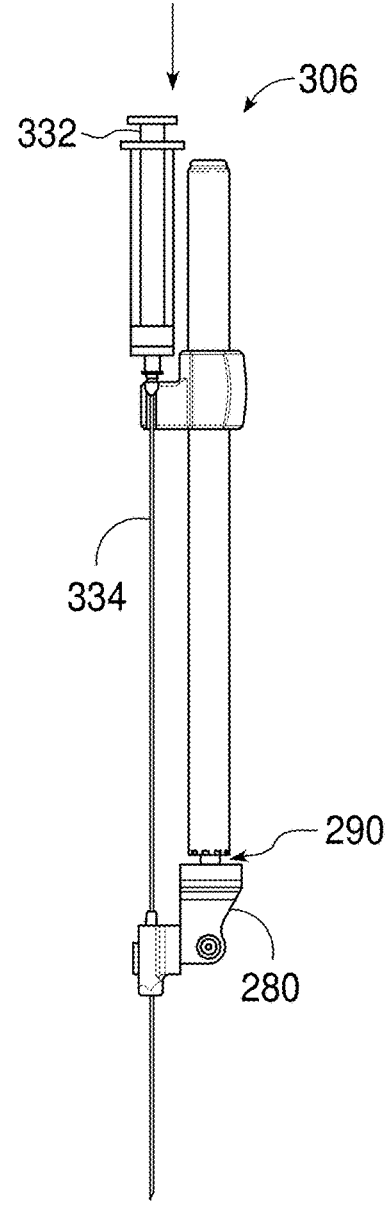
FIG. 2V1          FIG. 2V2          FIG. 2V3

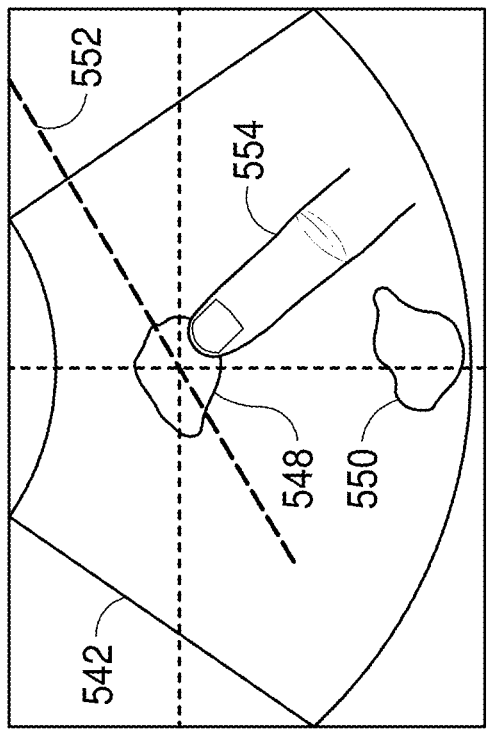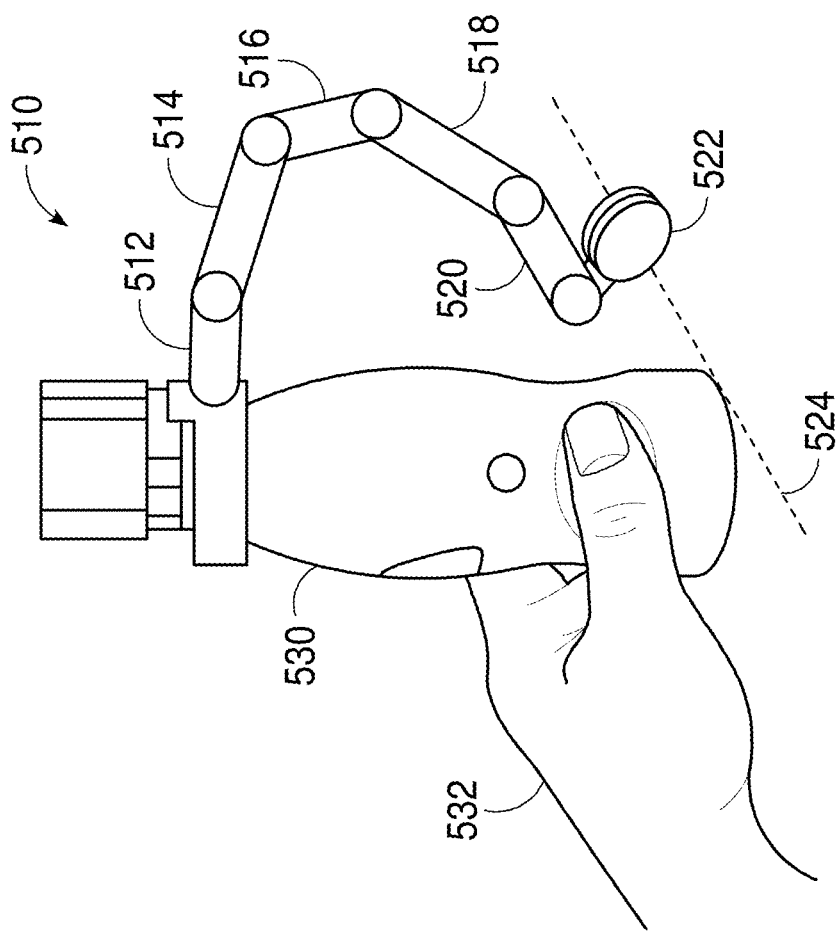
FIG. 5C

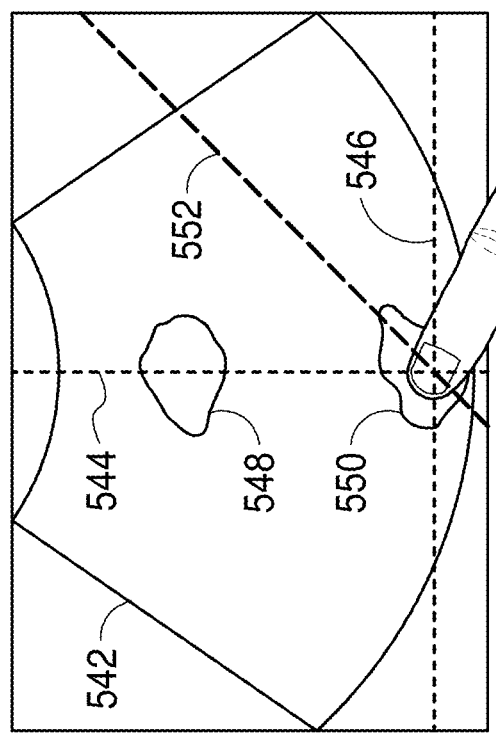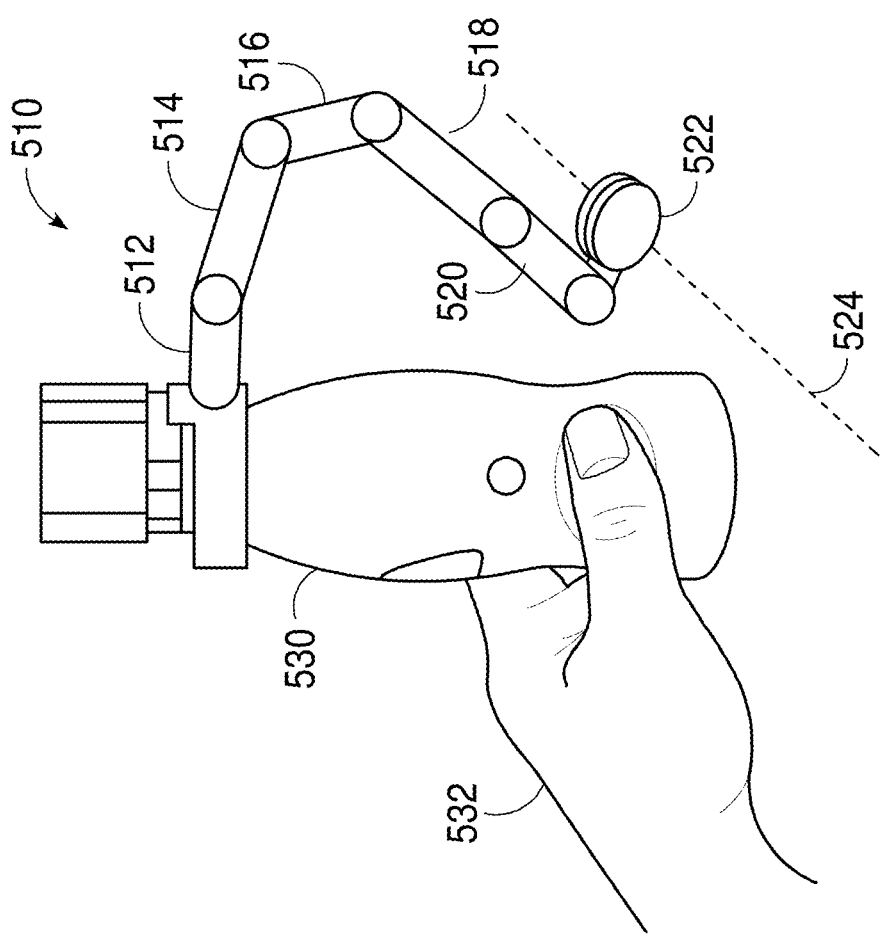
FIG. 5D

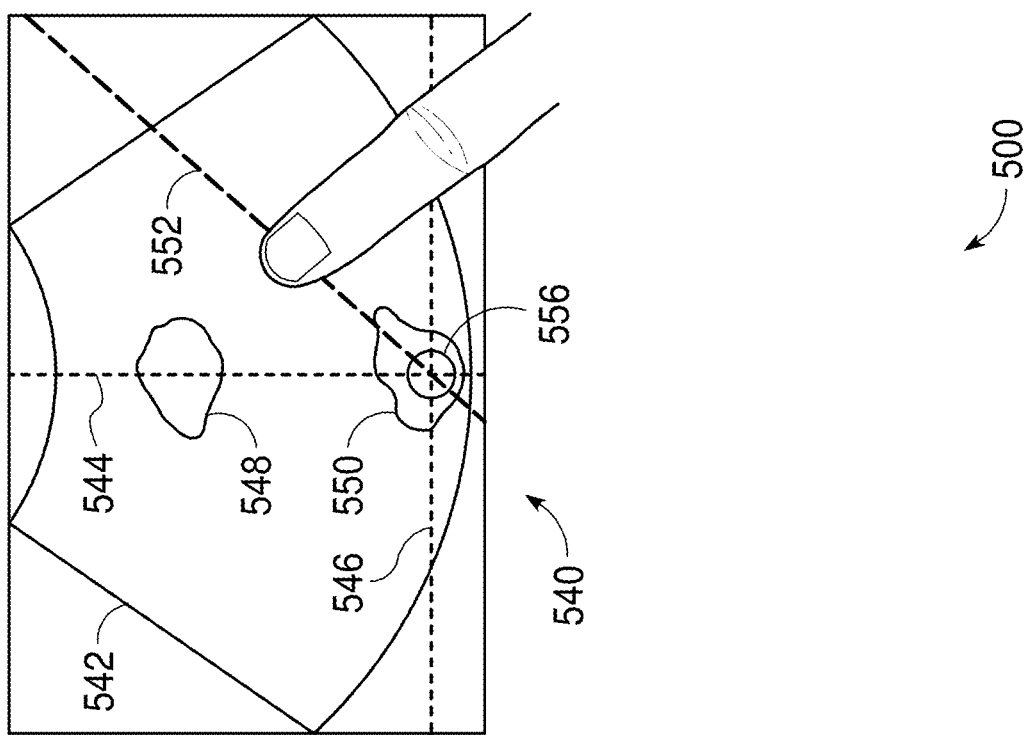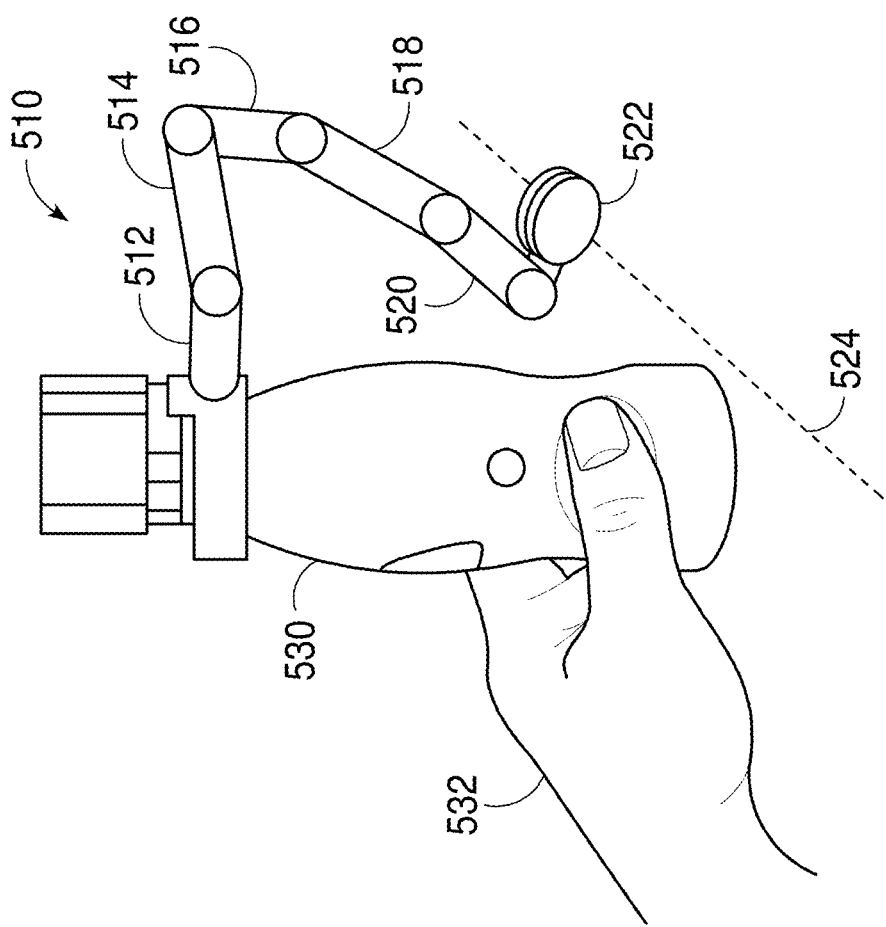
FIG. 5E

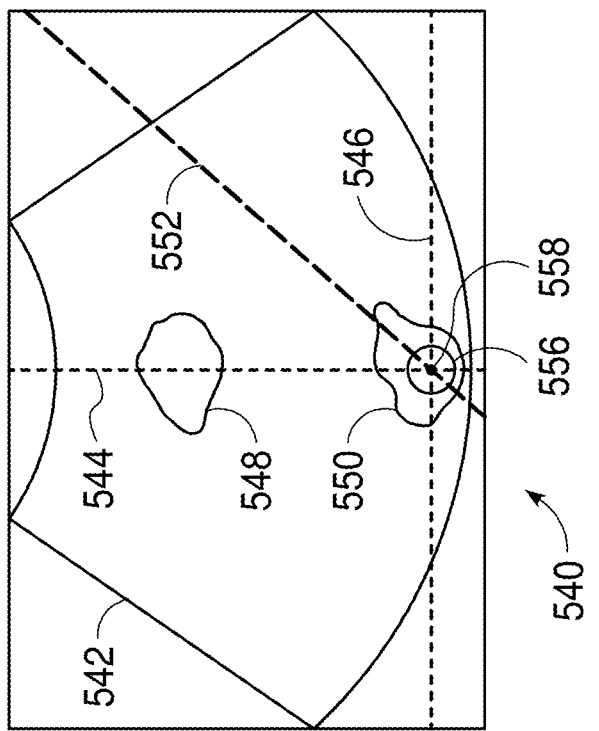
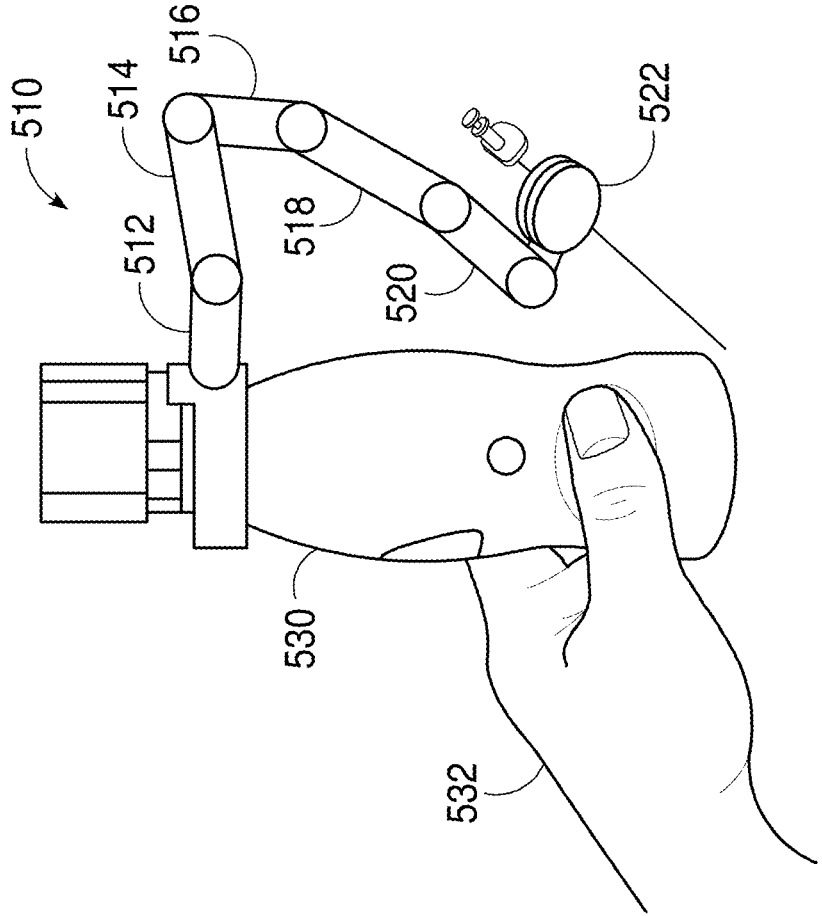
FIG. 5G

REAL TIME IMAGE GUIDED PORTABLE ROBOTIC INTERVENTION SYSTEM

CROSS REFERENCE TO RELATED APPLICATIONS

This application claims priority to U.S. Provisional Patent Application No. 63/219,662 filed Jul. 8, 2021, entitled "REAL TIME IMAGE GUIDED PORTABLE ROBOTIC INTERVENTION SYSTEM," which is incorporated by reference herein in its entirety.

TECHNICAL FIELD

The present invention relates to the field of medical imaging systems.

BACKGROUND

Minimally invasive medical techniques limit the size of incisions and minimize the iatrogenic effects of performing procedures in or on the human body. Minimally invasive medical techniques are inherently challenging to perform. They often include the use of imaging technology, specific devices that provide the ability to perform tasks despite constrained access to the body, and significant skill on the part of the user. In particular, the user must have spatial reasoning ability, as well as know how to effectively utilize imaging and minimally invasive devices. By contrast, open interventions are more invasive, but afford healthcare providers ("HCP" or "HCPs") the benefit of directly visualizing and accessing anatomy and pathology with their own hands.

Of the imaging modalities that enable minimally invasive interventions, ultrasound has many attractive characteristics namely, portability, cost, and absence of ionizing radiation. There has been an emerging trend in the development and use of even smaller, less expensive ultrasound systems to enable point-of-care ultrasound (POCUS) imaging to diagnose and potentially address medical issues where a patient is being treated rather than having to send or refer that patient to an imaging center and radiologist. While this technology has seen significant adoption for use in diagnostic applications, it has yet to transform ultrasound guided intervention at scale.

It is often desirable or necessary to enable percutaneous procedures with ultrasound image guidance despite the difficulty associated with manually inserting an interventional instrument through the skin while adequately visualizing both the target and the device. Doing so requires substantial training and practice to estimate the optimal entry point, trajectory, and depth for an interventional instrument to reach a target that is being imaged by the US probe. This specialized skill is difficult to acquire and precludes many clinicians from performing successful ultrasound guided percutaneous interventions.

Although performing these techniques is challenging, ultrasound systems are ubiquitous in healthcare systems. Due to the existing install base of ultrasound systems, there is a need to augment existing ultrasound systems with devices that allow clinicians to perform ultrasound guided percutaneous procedures.

There are four fundamental challenges associated with imaging (e.g., ultrasound) based intervention: Image acquisition, Image interpretation, Intervention planning, Intervention execution.

Image acquisition. Image acquisition may be challenging to HCPs due to various factors, including but not limited to poor motor skills, poor acoustic coupling, poor understanding of how to hold, apply, rotate, and angulate probe relative to the body to establish a relevant imaging window.

Image interpretation. Interpreting images (e.g., reading ultrasound images) may be challenging to HCPs due to various factors, including varying levels of understanding how ultrasound images are formed, how anatomy and pathology appears on ultrasound, and how to create cognitive three-dimensional (3D) information from a series of 2D planar images.

Intervention planning. Defining an optimal trajectory for an instrument (e.g., a needle) to hit an intended target with consistency, while avoiding anatomic constraints (e.g., avoiding contacting an unintended part of the anatomy) is challenging for HCPs due to various factors, including the absence of being able to consistently acquire, interpret 2D images, as well as derive a 3D volume from that information. Another challenge HCPs may face include the inability to contextualize the 2D images with respect to surrounding anatomy, which is more intuitive using 3D information.

Intervention execution. Even if an optimal trajectory for an instrument is defined, it is challenging for HCPs to consistently initiate and follow-through on their planned target due to various factors, including use of non-dominant hand to execute tasks, the ability to introduce instruments with the appropriate force and control with a single hand, challenge associated with obtaining optimal ultrasonic view of instrument tip while maintaining view of relevant anatomy, poor motor skills, steep needle insertion angles yielding poor reflection of sound waves, and planned versus actual needle path due to deflection. Moreover, manual techniques require the intervention plan to be created in the mind of the HCP based on a mental map created from scanning across the anatomy. The intervention execution requires the HCP to then manipulate a needle to through the skin to a target using a single image as a reference.

The challenges may compound due to all the aforementioned issues. For example, HCP is burdened with simultaneously attempting to acquire 2D images of the anatomy and surrounding structures, interpreting the 2D image to mentally map the anatomy, identify a trajectory for a needle to hit the target and avoid contacting unintended parts of the anatomy, hold the imaging device still, and insert the needle along the trajectory and compensate for issues (such as deflection).

SUMMARY

Embodiments disclosed herein describe an image-guided robotic intervention system ("IGRIS") comprised of a robotic instrument guide, an imaging device, a sterile boundary, patient-based fiducials, and system software. Each of these may be employed by healthcare professionals (i.e. users) when performing one or more medical procedures on patients. The IGRIS relies on imaging to provide the user with a real-time view of patient anatomy and pathology, as well as an intended target or targets for the procedures, software that allows a user to plan an approach or trajectory path using either the image or the robotic device, software that allows a user to convert a series of 2D images into a 3D volume, and localizes the 3D volume with respect to real-time images during the procedure. Additionally, IGRIS may include sensors to estimate pose (also referred to as position and orientation) of the imaging device relative to the patient to improve the performance of that software with respect to runtime, robustness, and accuracy.

The IGRIS is comprised of the following hardware components: (1) an Imaging Device capable of imaging objects, such as patient anatomy and pathology, (2) a computer to perform calculations and algorithms based on those images, and (3) a robotic arm (e.g., a robotic manipulator and an instrument guide) that affects the use of an instrument which interacts with the patient anatomy and pathology. Here, the Health Care Provider ("HCP") or user interacts with the system and potentially the instrument itself to execute the procedure.

In one embodiment of the system disclosed here, the imaging is real-time ultrasound; the instrument is intended to be introduced percutaneously, directed in an approximately straight line to an anatomical target. The imaging, a computer, and robotic arm may be handheld. Alternatively, the elements may be mounted on at least one positioning apparatus where the elements are manipulated manually or via robotic actuation.

As such the HCP interacts with IGRIS to physically stabilize the system and acoustically couple the ultrasound transducer to the patient; acquire and interpret ultrasound images; configure, plan and execute an intervention using typical computer input interfaces (e.g., touch screen, mouse, keyboard, joy stick, track ball, etc.); and may collaboratively manipulate the instrument to optimize the intervention.

In some embodiments, IGRIS may not include an Imaging Device and may be operated to couple with existing Imaging Devices. For example, IGRIS may be attached to a standard ultrasound device and operate in the same manner as an IGRIS with an integrated Imaging Device.

The IGRIS supports multiple operational modes or embodiments, including Basic Targeting and Intelligent Targeting. Each shall be described in further detail below.

Modular Robotic Arm

Embodiments disclosed herein describe a modular robotic arm, which is designed to mount to an Imaging Device (e.g., any standard ultrasound probe). The modular robotic arm may be referred to herein as modular robotic assembly, robotic arm, robot arm, robot, or arm. In some embodiments, modular robotic arm may comprise a robotic manipulator, instrument guide, motors, encoders/IMU, and may be coupled to a computer. In some embodiments, modular robotic arm may support a detachable or disposable instrument guide. In some embodiments, modular robotic arm may be represented as IGRIS 100 without the Imaging Device. As such, modular robotic arm supports the same modes and embodiments as IGRIS 100 once coupled to an Imaging Device.

The modular robotic arm may be used in a wide variety of percutaneous procedures on an object (e.g., human anatomy). In some embodiments, a user may hold the Imaging Device (e.g., ultrasound probe) with the modular robotic arm mounted in one hand, the modular robotic arm points an instrument guide at the target, and the user manually inserts the needle through the instrument guide. In some embodiments, the modular robotic arm may also automatically insert the needle through the instrument guide.

Sterile Boundary

Embodiments disclosed herein describe a sterile boundary (or sterile barrier), comprising one or more highly compliant (e.g., drape-like) sections and one or more rigid (e.g., plastic- or rubber-like) sections to limit communication of particles from an image guided robotic intervention system ("IGRIS") (e.g., modular robotic arm or IGRIS 100). In some embodiments, sterile boundary may be used with modular robotic arm or IGRIS 100 discussed herein to maintain a sterile barrier between the HCP, patients, and all non-sterile equipment (e.g. ultrasound probe) during procedures.

The sterile boundary may couple to key features of the robotic device (e.g., IGRIS 100 or modular robotic arm), and may include transparent elements to permit visualization of a screen/user interface and to allow touch signal to pass through it to enable interaction with a touchscreen. The sterile boundary may comprise integrated coupling gel. In some embodiments, the sterile boundary may also cover an instrument guide (e.g., a physical needle guide).

Instrument Guide

Embodiments disclosed herein describe an instrument guide. The instrument guide may be used in robotic percutaneous procedures which use a robotic arm (e.g., IGRIS 100 or modular robotic arm) to guide or drive an instrument (e.g., a needle) through the skin to target anatomy. In some embodiments, instrument guide may be integrated into modular robotic arm, or may be attached/detached from the modular robotic arm.

In some embodiments, a custom sterile boundary for the instrument guide may be created for the instrument guide, and may include a factory integrated model, or a model which can be affixed prior to use. In some embodiments, the instrument guide may be disposable for sterility.

In some embodiments, the instrument guide may include grip/guide/release capabilities. The instrument guide may grip an instrument (e.g., a needle) securely so the user may perform various tasks, such as remove accessories from the needle (e.g. a syringe) or perform ancillary tasks while constraining axial and rotational motion. The instrument guide may guide the instrument along an axial trajectory to hit a target, and allow rotation. The instrument guide may release the instrument while it is inserted in the patient to allow subsequent procedural tasks without the robotic arm or IGRIS.

In some embodiments, instrument guide may measure the depth of the needle to provide feedback to the user and/or robotic system.

In some embodiments, instrument guide may support the instrument (e.g., needle) in a manner that allows the user to Backdrive the robotic arm to manually and collaboratively adjust the needle trajectory, or interact with the robot in a haptic manner.

In some embodiments, the sterile boundary may integrate as an interface between a sterile instrument guide and a non-sterile modular robotic arm (or IGRIS), covering the modular robotic arm (or IGRIS) and exposing the sterile instrument guide, essentially allowing for an entirely sterile device using the sterile needle guide functionality.

Calibration

IGRIS 100 may perform an initial calibration using Software 120 which performs an optimization and synchronization of the IGRIS 100 hardware components, including Imaging Device 146, Robotic manipulator 126, and Instrument Guide 128. Calibration may compute an accurate mathematical representation or transformations between components of the Imaging Device 146, Robotic manipulator 126, and Instrument Guide 128. Calibration may be performed during manufacture and assembly, prior to use, or during use. Calibration may also be performed automatically by Software 120.

IGRIS 100 includes various types of calibration including (1) Robotic manipulator 126 to Instrument Guide 128 calibration, (2) Imaging Device 146 to Robotic manipulator 126 calibration, and (3) Real-time Images (acquired from Imaging Device 146) to Imaging Device 146. In some embodiments, Calibration may be performed during or prior to each procedure, or calibrated prior to deployment (e.g., during manufacture/assembly).

Basic Targeting

Using IGRIS, Basic Targeting allows a user to plan and execute an intervention (e.g., inserting an instrument, such as a needle, into a patient) in a more precise manner than conventional methods. In some embodiments, IGRIS 100 may perform an initial calibration step prior to use to ensure targeting accuracy.

IGRIS may acquire real-time images of an object (e.g., a human anatomy) using an Imaging Device (e.g., ultrasound) for display on a user interface of a computer.

IGRIS comprises a robotic manipulator (e.g., robotic arm) coupled to the Imaging Device and an instrument guide. The robotic manipulator may be driven by motors and sensors (encoders), which may be used to control the pose (e.g., position and orientation) of the instrument guide, and thus the instrument relative to the Imaging Device.

IGRIS tracks the instrument guide's pose relative to the Imaging Device using data from Calibration and the robotic manipulator, including (1) the pose of the robotic manipulator relative to the Imaging Device and/or (2) the pose of the instrument guide relative to the robotic manipulator to determine the desired trajectory of instrument guide relative to the Imaging Device.

IGRIS may augment the real-time images on the user interface with a first graphical overlay that represents the planned trajectory of the instrument relative to the image and a second graphical overlay that represents the projected instrument depth during an intervention. The graphical overlays are updated in real-time based on any adjustments of the robotic manipulator and instrument guide. Conversely, the pose of the robotic manipulator and/or instrument guide are also updated in real-time based on any adjustments of the user interface.

Basic Targeting supports multiple modes, including Backdrive and Tap to Target. Backdrive allows a user to adjust the pose of the instrument guide and/or the robotic manipulator manually, and the updated pose or needle path is represented on the user interface in real-time. Tap to Target automatically adjusts the pose of the instrument guide and/or robotic manipulator by selecting, or "tapping," an area of interest on the user interface displaying the real-time images of the object using an input device (e.g., touch screen, mouse, keyboard, joy stick, track ball, etc.). The area of interest may define a desired target location for the needle, adjust the path the needle takes to the target, or both.

Intelligent Targeting

Using IGRIS, Intelligent Targeting allows a user to plan and execute an intervention using 3D reconstructions of anatomy generated from 2D real-time images and using enhanced localization techniques to target specific areas of the anatomy. This may assist an HCP visually and offload the cognitive burden of attempting to interpret and identify target areas in the real-time images. For example, an HCP, who may be unsuccessful in locating a specific target location in the anatomy for a needle insertion using real-time ultrasound, may instead use Intelligent Targeting to generate a 3D reconstruction of the anatomy based on the real-time ultrasound images to more easily identify the target location. The HCP may also use enhanced localization techniques to track and lock on to the target location to prepare for the needle insertion. In some embodiments, IGRIS 100 may perform an initial calibration step prior to use to ensure targeting accuracy.

Intelligent Targeting includes two main features to facilitate such interventions: 3D Reconstruction and Localization.

3D Reconstruction refers to the creation of volumetric information based on a plurality of 2D real-time images (e.g., ultrasound) of an object (e.g., anatomical region of a body) and rendering the reconstruction to present a human interpretable view of the anatomy for procedural planning, as well as assisting in automatically planning the procedure. This includes the anatomy of interest as well as surrounding anatomy for detailed trajectory planning.

Localization refers to computing the pose of a real-time image (e.g., ultrasound), and as a result IGRIS, with respect to the target object and the volumetric imaging data of the scanned anatomy. Localization provides the ability to infer the location of target and surrounding anatomy in space relative to IGRIS as well as any trajectory planning primitives defined as a result of analyzing or interpreting the volumetric data, whether it be by a human or computer.

For example, IGRIS may acquire a plurality of real-time images of an object (e.g., a human anatomy) using an Imaging Device (e.g., ultrasound). IGRIS may also include sensors to generate metadata for each of the real-time images, including information related to IGRIS when each image was captured (e.g., the pose of the components of IGRIS, the location of IGRIS relative to the object, timestamp information, the orientation of IGRIS, the velocity and direction of IGRIS, etc.). IGRIS comprises a computer which receives the plurality of real-time images and the associated metadata. IGRIS performs a correlation of the real-time images and metadata to generate a 3D Reconstruction of the object. In some embodiments, IGRIS may perform a non-linear optimization of the real-time images (without the metadata), based on consistency or correlation to generate a 3D Reconstruction of the object.

IGRIS includes an interactive user interface for display of the 3D Reconstruction in multiple view angles (e.g., coronal view (frontal), sagittal (lateral), and transverse (axial)). IGRIS may augment the 3D Reconstruction on the user interface with a first graphical overlay that represents the pose of the Imaging Device relative to the object by way of localization information. Additionally, IGRIS may augment the 3D Reconstruction on the user interface with a second graphical overlay that represents the desired (or planned) trajectory of the instrument relative to the anatomy. The graphical overlays are updated in real-time based on any adjustments of the Imaging Device, the robotic manipulator, and the instrument guide. A user may more easily locate and select the specific target area IGRIS may then provide an indicator on the user interface of the position and orientation of IGRIS relative to the specific target area. IGRIS comprises a robotic manipulator (e.g., robotic arm) coupled to the Imaging Device (e.g., ultrasound) and an instrument guide. IGRIS may be "locked" to the specific target area to prepare for the needle insertion, and the robotic manipulator will keep the instrument guide "locked on," or targeted, to the specific target area even if IGRIS is not still.

Instrument Insertion

Once IGRIS is in position for instrument insertion, possibly via the Basic Targeting and Intelligent Targeting flows, IGRIS may prepare for insertion of the instrument into the object (e.g., patient anatomy) using various techniques described herein.

BRIEF DESCRIPTION OF THE DRAWINGS

FIGS. 2A-2V3, inclusive, illustrate a modular robotic assembly 200.

FIGS. 5A-5G, inclusive, illustrate an embodiment of Basic Targeting.

DETAILED DESCRIPTION

Figure 1:
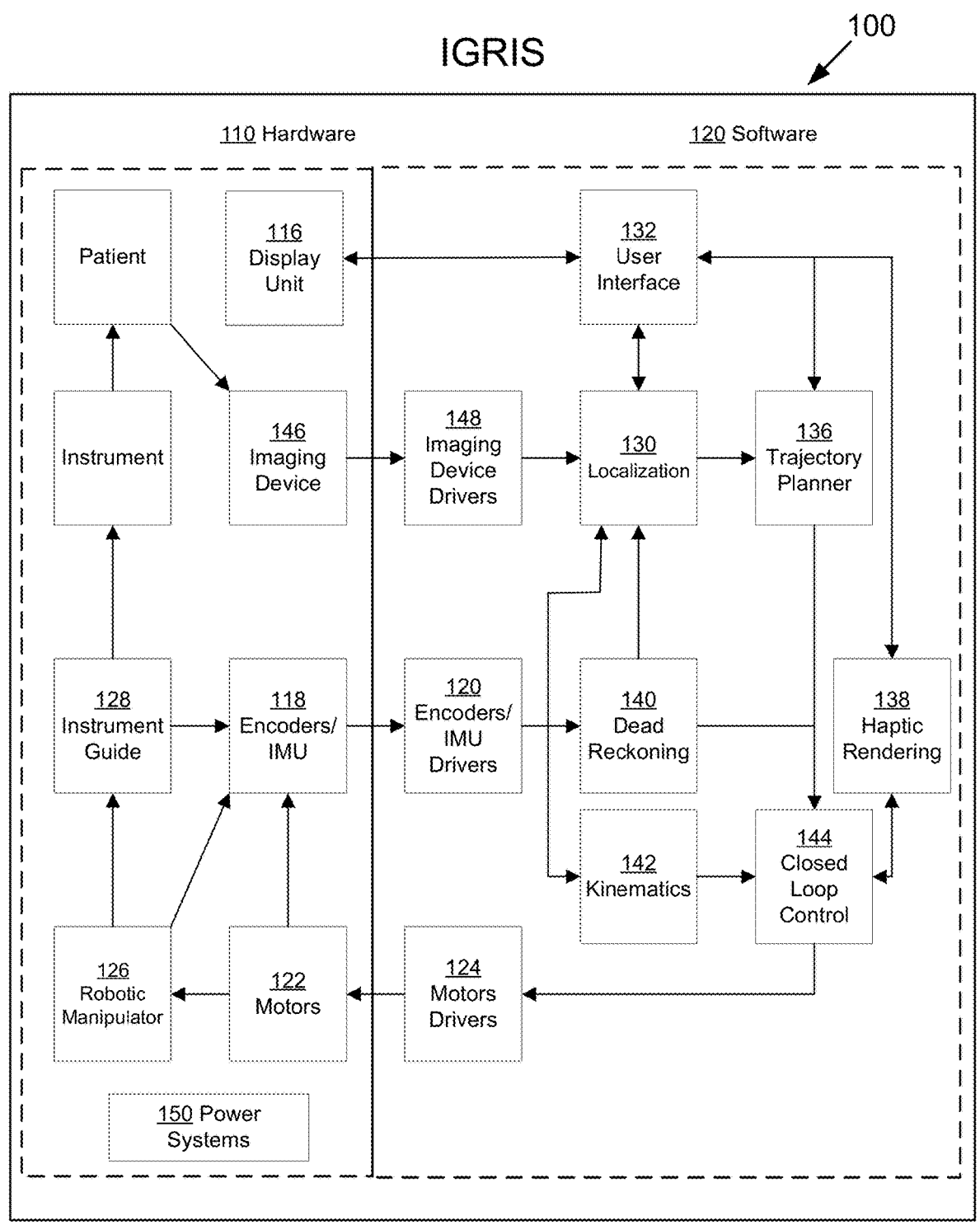
FIG. 1 illustrates an embodiment of an IGRIS 100 suitable for implementation of the inventive concepts described herein.

The following description is provided to enable any person skilled in the art to make and use the invention, and is provided in the context of a particular application and its requirements. Various modifications to the embodiments may be possible to those skilled in the art, and the generic principles defined herein may be applied to these and other embodiments and applications without departing from the spirit and scope of the invention. One skilled in the relevant art will recognize that embodiments of the inventive concepts disclosed herein can be practiced without one or more of the specific details, or in combination with other components, etc. In other instances, well-known implementations or operations are not shown or described in detail to avoid obscuring aspects of various embodiments of the inventive concepts disclosed herein. Thus, the present invention is not intended to be limited to the embodiments shown, but is to be accorded the widest scope consistent with the principles, features and teachings disclosed herein. In the following description, several specific details are presented to provide a thorough understanding of embodiments of the inventive concepts disclosed herein.

Image-Guided Robotic Intervention System ("IGRIS")

Embodiments disclosed herein describe an image-guided robotic intervention system ("IGRIS") comprised of a robotic instrument guide, an Imaging Device, a sterile barrier, patient-based fiducials, and system software. Each of these may be employed by healthcare professionals (i.e. users) when performing one or more medical procedures on patients. The IGRIS relies on imaging to provide the user with a real-time view of patient anatomy and pathology, as well as an intended target or targets for the procedures, software that allows a user to plan an approach or trajectory path using either the image or the robotic device, software that allows a user to convert a series of 2D images into a 3D volume, localization sensors to determine the pose of the devices relative to the patient, patient anatomy and pathology.

The IGRIS is comprised of the following hardware components: (1) an Imaging Device capable of imaging objects, such as patient anatomy and pathology, (2) a computer to perform calculations and algorithms based on those images, (3) a robotic arm (e.g., a robotic manipulator and an instrument guide) that affects the use of an instrument which interacts with the patient anatomy and pathology, and (4) external sensors (e.g., IMU and cameras). Here, the Health Care Provider ("HCP") or user interacts with the system and potentially the instrument itself to execute the procedure.

In one embodiment of the system disclosed here, the imaging is real-time ultrasound; the instrument is intended to be introduced percutaneously, directed in an approximately straight line to an anatomical target. The imaging, a computer, and robotic arm may be handheld. In some embodiments, computer processor operations, including and not limited to machine learning and/or artificial intelligence, may be offloaded to the cloud for processing.

Alternatively, the elements may be mounted on at least one positioning apparatus where the elements are manipulated manually or via robotic actuation.

As such the HCP interacts with IGRIS to physically stabilize the system and acoustically couple the ultrasound transducer to the patient; acquire and interpret ultrasound images; configure, plan and execute an intervention using typical computer input interfaces (e.g., touch screen, mouse, keyboard, joy stick, track ball, etc.); and may collaboratively manipulate the instrument to optimize the intervention.

In some embodiments, IGRIS may not include an Imaging Device and may be operated to couple with existing Imaging Devices. For example, IGRIS may be attached to a standard ultrasound device and operate in the same manner as an IGRIS with an integrated Imaging Device. This may be represented at a "modular robotic arm," which is discussed in further detail below.

The IGRIS supports multiple operational modes or embodiments, including Basic Targeting and Intelligent Targeting. Each shall be described in further detail below.

Referring now to FIG. 1, an embodiment of an IGRIS 100 suitable for implementation of the inventive concepts described herein. In some embodiments, IGRIS 100 and/or the components thereof may be portable and/or handheld. IGRIS 100 includes hardware components 110, software modules 120, and power system(s) 150 may include any source(s) of power which provides power to IGRIS 100.

Hardware components 110 may include Imaging Device 146, display unit 116, encoders/IMU 118, motors 122, robotic manipulator 126, and instrument guide 128.

Software components may include Imaging Device Driver 114, encoders/IMU drivers 120, motors drivers 124, user interface 132, localization 130, trajectory planner 136, haptic rendering 138, dead reckoning 140, kinematics 142, closed loop control 144.

Imaging Device 146 may include any device configured for emitting and/or acquiring signals representative of anatomical feature(s) and converting the signals into data representative of the same feature(s). One such device could be an ultrasound (US) sensor configured with an US transducer and processing hardware configured to transmit and receive ultrasonic signals and process raw data for extracting useful information related to imaging modalities such as, but not limited to, M-Mode, B-Mode, and/or Doppler. In some embodiments, transducer architectures or technologies which facilitate a steering of US signals may be employed such as, but not limited to, linear array, matrix array, phased array, actuated or wobbled transducers, and/or rotated transducers. Imaging Device drivers 148 could be any software configured to receive information from the Imaging Device 146 and provide one input to a localization module.

Display unit 116 may include any interfaces and displays for user input and displaying images and video to the user. In some embodiments, display unit 116 may include an integrated touch screen and display on the handheld device, but alternative embodiments could include a user interface and/or display attached to a portable cart, instead of or in addition to the interface/display on the handheld device. In some embodiments, alternative input devices (e.g., touch screen, mouse, keyboard, joy stick, track ball, etc.) may be used to provide input.

Encoders/IMU 118 may include sensors that capture and provide information related to motions of the inertial and/or dynamic state of IGRIS and/or robotic manipulator 126 and/or instrument guide 128. Encoders/IMU drivers 120 could be any software configured to receive information from the Encoders/IMU and provide inputs to the localization module, a dead reckoning module, and a kinematics module. Additional sensors (e.g., external sensors) which are not shown are discussed in further details in the "3D Reconstruction and Localization" section below.

Motors 122 may include one or more motors (e.g., actuators) used in the positioning of the distal end of the robotic arm of robotic manipulator 122 for guiding the instrument to the target or locus. Motor drivers 124 may be employed to receive motor driver information from a motor driver module and provide control information to the one or more motors.

Robotic manipulator 126 may be a device configured to convert motions of actuators to an Instrument Guide 128 pose. Robotic arm includes robotic manipulator 126 coupled to an instrument guide 128. In some embodiments, robotic manipulator 126 can be coupled on a robotic stereotactic frame, where robotic manipulator 126 and/or Imaging Device 146 may be actuated or manually manipulated. In some embodiments, robotic manipulator 126 and Imaging Device 146 may be coupled to a robotic arm(s) which could be controlled to position these in the desired location. In some embodiments, these may be employed as a handheld, a second robotic arm other than the arm coupled to robotic manipulator 126, or with a structure employing the second robotic arm. In some embodiments, robotic manipulator 126 may be attachable to and removable from any of the stabilizing structures such as, but not limited to, the second robotic arm stereotactic frame as described above.

In some embodiments, kinematic relationships between robotic manipulator 126 and Imaging Device 146 may be computed to target the anatomical target or locus captured in an image of Imaging Device 146. For example, through the use of the ultrasound imaging, targeting may be updated in real time by servo(s) controlling the robotic arm. An exemplary robotic manipulator 126 is discussed in detail below.

Instrument guide 128 may be an interface for coupling the instrument to robotic manipulator 126, where the instrument coupled to instrument guide 128 may be any implement which is designed to pierce a body. Instrument guide 128 and instrument are discussed in detail below.

In some embodiments, instrument guide 128 may have different geometries for different procedures. In some embodiments, instrument guide 128 may be sterile and/or integrated with sterile draping as discussed below. In some embodiments, instrument guide 128 may be passive to allow the user to freely insert the instrument through it. In some embodiments, instrument guide 128 may be automated for complete automated instrument insertion.

Software modules 120 may include modules applicable to the user interface 132, localization 134, trajectory planner 136, haptic rendering 138, dead reckoning 140, kinematics 142, and closed loop control 144.

User interface 132 may be configured to receive user inputs and presents visualizations. Inputs may include data entry from the user for configuration of IGRIS 100, selection of the procedure to be performed or anatomy to be targeted, procedure planning, and confirmatory steps. Visualizations may include real-time imaging acquired by Imaging Device 146 that could include planar, multi-planar, and/or volumetric imaging.

In some embodiments, images may be augmented with graphical overlays that may enhance the visualizations to include, but not limited to, annotated anatomy, instrument location, and other guidance cues for steering the instrument. In some embodiments, MRI/CT and 3D US reconstructions may overlay the real-time images. In some embodiments, simulated views representative of anatomy and instrument locations and anatomical features may be graphically displayed.

Localization module 130 may be employed to find the anatomical site at which a medical procedure may be performed. In some embodiments, the user could either randomly or systematically manipulate the US transducer until the user happens upon the procedure site. IGRIS 100 could then identify the anatomy and indicate on the user interface that the procedure site is within the image. In some embodiments, IGRIS 100 could guide the user with audible, visual, and/or haptic cues to perform a systematic search in order to find the anatomy of interest.

Localization module 130 may compute the pose of anatomy in a known coordinate frame. Input of real-time information may include input of Imaging Device information such as, but not limited to, acquired images (e.g., ultrasound images), input of sensor information, IMU/encoder information and/or other motion capture information. In some embodiments, a priori information may be included as inputs. A priori information includes information used to assist with the procedure, including MRI, CT Scans, general human models, which may be implemented via neural networks. A priori information may also include pre-procedure planning information, including patient-specific (e.g., pre-op imaging, planning, no-fly zones, volumetric measurements, etc.) and non-patient-specific (e.g., learned or heuristic models tuned to general human anatomy, or other information which may enable the user the ability to identify and segment observed anatomy and understand deformation.).

Localization module 130 may also localize anatomy directly in a single image slice in addition to user-localizing. An US image is a 2D slice of the 3D objects being imaged, and as such, anatomy may be localized in 3D space relative to the US probe by directly processing the image itself. For example, segmented pixels associated with the periphery of a kidney are inherently localized in that their precise position is known relative to the transducer.

Heuristics could include a class of classical image analysis techniques which encode rules to extract information from an image. Techniques include, but are not limited to, thresholding, shape fitting, and center of mass computations. When employed, these techniques are useful to segment anatomy explicitly from simple anatomical structure in a general way without the need for training data. These techniques may have to handle various complications such as, but not limited to, image quality variance (contrast, brightness, etc.) and deformation (write a heuristic that is robust to it).

The invention may also train AI/ML models to directly detect anatomical features. Instead of comparing the US images to volumetric models, the anatomy could be encoded in the networks themselves as statistical models. Using these types of models, it may be possible to classify pixels and derive information including, but not limited to, identification of organs, identification of pathology, calculation of organ volume, identification of anatomy-to-target, and identification of anatomy to avoid during an intervention. Alongside the ability to classify pixels, additional tasks such as, but not limited to, a method of joint estimation through an estimation of a deformation field could be embedded into the network.

Trajectory planning module 136 may be configured to receive inputs that include localization data, constraints informed by user inputs, the intervention plan, and any other a priori information. From at least these inputs, a reference trajectory may be determined for the robotic end effector (or robotic arm distal end) and commands could be provided to facilitate the steering or approach of the instrument to the target anatomy. In some embodiments, this trajectory could include an avoidance of critical anatomical obstacles, a rejection of disturbances, and the like. In some embodiments, the input could include an estimate of actual instrument tip location to compensate for a presence of undesirable instrument deflection and error.

Haptic rendering module 138 may include a rendering of reference geometries for display to the user such as, but not limited to, walls, springs, dampers, repulsive fields (opposite of spring), and masses. Haptic rendering could also include stimuli input to the user such as, but not limited to, applying desired tactile sensory stimuli. These may be useful to guide the user when there are, for example, adjustments to the interventional plan and enforcement of boundaries to prevent the user from inadvertently hitting objects that should be avoided or inserting an instrument tip beyond an intended target.

Dead reckoning module 140 may be configured to compensate for inertial disturbances at a relatively high update rate to improve targeting. Because US image based algorithms could have relatively large computational requirements, anatomical image feedback (e.g., image-based feedback of trajectory planning) may be provided at a relatively slower and potentially non-deterministic rate through a soft real time system comprised of components associated with complex algorithms and interfaces requiring relatively high computational performance. Feedback loops in a hard real time system comprised of components associated with algorithms and interfaces that are not as complex may be more reliable and realized at a higher update rate, such that dead reckoning could allow for higher bandwidth compensation of inertial disturbances in between image-based feedback updates.

Kinematics module 142 may be configured to determine the instantaneous position (and velocity) of the end effector from motion and/or positional measurements of the current state of the robotic arm information.

Closed loop control module 144 may be configured to receive outputs from the trajectory planning and haptic rendering modules, and compare those to measurements received from the dead recognizing and forward/inverse kinematics modules to determine motor commands. In some embodiments, information corresponding to these commands could adjust trajectory planning, haptic rendering, and active compensation of the user's interface (i.e., hand motion) to keep the needle guide stable by rejecting inertial disturbances resulting from rotations and small translations of the robotic arm.

Modular Robotic Arm

Embodiments disclosed herein describe a modular robotic arm, which is designed to mount to an Imaging Device (e.g., any standard ultrasound probe) and coupled to a computer. The modular robotic arm may be referred to herein as modular robotic assembly, robotic arm, robot arm, robot, or arm. In some embodiments, the modular robotic arm may be represented as IGRIS 100 without the Imaging Device 146.

The modular robotic arm may be used in a wide variety of percutaneous procedures on an object (e.g., human anatomy). In some embodiments, a user may hold the Imaging Device (e.g., ultrasound probe) with the modular robotic arm mounted in one hand, the modular robotic arm points an instrument guide at the target, and the user manually inserts the needle through the instrument guide. In some embodiments, the instrument guide may be removable and replaceable. Preferably, the modular robot arm may operate in a sufficiently large workspace to accommodate inserting a needle near the ultrasound probe, as well as far away to enable a wide variety of percutaneous procedures. Further, the instrument guide and the robotic joints of the modular robotic arm are slim in profile to avoid collision with the Imaging Device, the robot itself (self collisions), and surrounding external anatomy. The modular robotic arm may also comprise gripping and insertion mechanisms to allow the modular robotic arm to measure and/or control the instrument insertion degree of freedom.

Modular robotic arm (1) may be universally mountable to a plurality of Imaging Devices, (2) may be mountable around an existing cabling (which may not be removable) while maintaining 360 degree rotation (3) includes a homogenous kinematic architecture, and (4) a low profile wrist via remote actuators (e.g. cable drives).

The modular robot arm may support backdriving, which allows the user to adjust the instrument guide manually. This backdriven motion may be constrained or unconstrained to help the user more easily adjust the needle trajectory. For example, the instrument guide (e.g., needle guide) may point at the target while allowing the user to adjust the entry site—or vice versa. For the backdriving mode to be intuitive, the robot may include homogeneous kinematic properties throughout the workspace keeping it away from singularities.

In some embodiments, the modular robot arm may be symmetrically mounted on an Imaging Device to ensure flexibility in probe/robot orientation, thereby facilitating left and right hand use, as well as robot in front and behind configurations.

The modular robotic arm may be coupled to a computer. The computer is calibrated such that defining anatomy in the image space (pixels) allows the robot to point the end effector to target the same anatomy in physical space. Further details regarding calibration are discussed in further detail below.

The modular robotic arm may include a first joint that can fit around existing Imaging Device cabling (e.g., a fixed ultrasound probe cable), yet still rotate freely. The modular robotic arm may attach to the Imaging Device via a semi permanently mounted Imaging Device specific receptacle. The receptacle/robot interface may be standardized such that the robot may attach to any Imaging Device with a corresponding receptacle.

Modular robotic assembly may mount to any Imaging Device (e.g., any ultrasound probe) using an interface. A specific interface may exist for every compatible Imaging Device. One end of the interface may include a unique design to couple to the external housing of Imaging Device. The other end of the interface may include coupling geometry to attach to the modular robotic arm. The coupling geometry may include a number of features: (1) keying geometry to control the orientation of the mechanical mounting of the robot to the Imaging Device; (2) locking features so that the modular robotic assembly may be locked on top of the Imaging Device; and (3) electrical contacts to provide power and communication to accessories that may be embedded in the interface including buttons, cameras, and an IMU.

In some embodiments, modular robotic assembly comprises complimentary coupling geometry that attaches to the interface at the first rotational joint. In some embodiments, the robotic arm comprises a relief that allows the joint to slip past cabling that drives the Imaging Device. For example, this relief may create a distinctive C shaped geometry as opposed to the traditional O shaped geometry of a traditional robotic joint. In some embodiments, the components of the joint (e.g. bearings, bushing, etc.) must "jump the gap" to provide stiffness through large rotations. In some embodiments, a recirculating bearing may be used. In some embodiments, when paired with multiple drive gears, the joint can still rotate 360 degrees around the Imaging Device. In some embodiments, when paired with a single drive gear, the joint may allow almost 360 degree rotation.

Modular robotic assembly comprises a unique kinematic geometry that has the following joint types: Rotational, Rotational, Prismatic (or Linear), Rotational, Rotational ("RRPRR") which allows for a large workspace with very homogeneous kinematic properties. Aspects of the present invention may operate using other kinematic geometries as understood by one of skill in the art, including and not limited to parallel manipulator systems. In some embodiments, the first rotational joint may be mounted such that the rotational axis is along the axis of the probe, acting similar to a turret. In some embodiments, the turret may position the rest of the modular robotic arm symmetrically around the Imaging Device. This enables the modular robotic arm to be positioned arbitrarily and symmetrically around the Imaging Device in rotation and in a mirroring fashion.

In some embodiments, the rotational axis of the modular robotic arm may be "locked" in fixed positions using constrained motion. For example, the "turret" may be locked at certain positions, such as the 3, 6, 9, and 12 o'clock positions, or any 360 degree position. In some embodiments, the first rotational joint may be a passive joint that may also be "locked" in fixed positions, however, is not robotically actuated. For Example, the first rotational joint may be manually rotated and locked into a desired position. In some embodiments, the locking mechanism may include a clicking mechanism, or detent, where first rotational joint clicks into place. In some embodiments, the locking mechanism may include a button or trigger that can lock the first rotational joint in place. The passive joint may still include an encoder to measure the joint position to facilitate kinematic computations.

Modular robotic arm comprises a second and third rotational joint to form a "wrist" to orient the instrument. The second and third rotational joints may be cable driven, or other mechanisms like pushrods or gears to remotely actuate the joint, to allow the geometry to be small near the instrument insertion site and near the Imaging Device. Modular robotic arm comprises corresponding motors for the rotational joint. In some embodiments, the motors may be housed in the joint link just proximal to the wrist. The cables may be routed through the first rotational joint to access the second rotational joint. The cables may be routed around capstans and crimped such that when the motors rotate, the cables transfer force to the joint capstan and rotate the wrist.

Figure 2A:
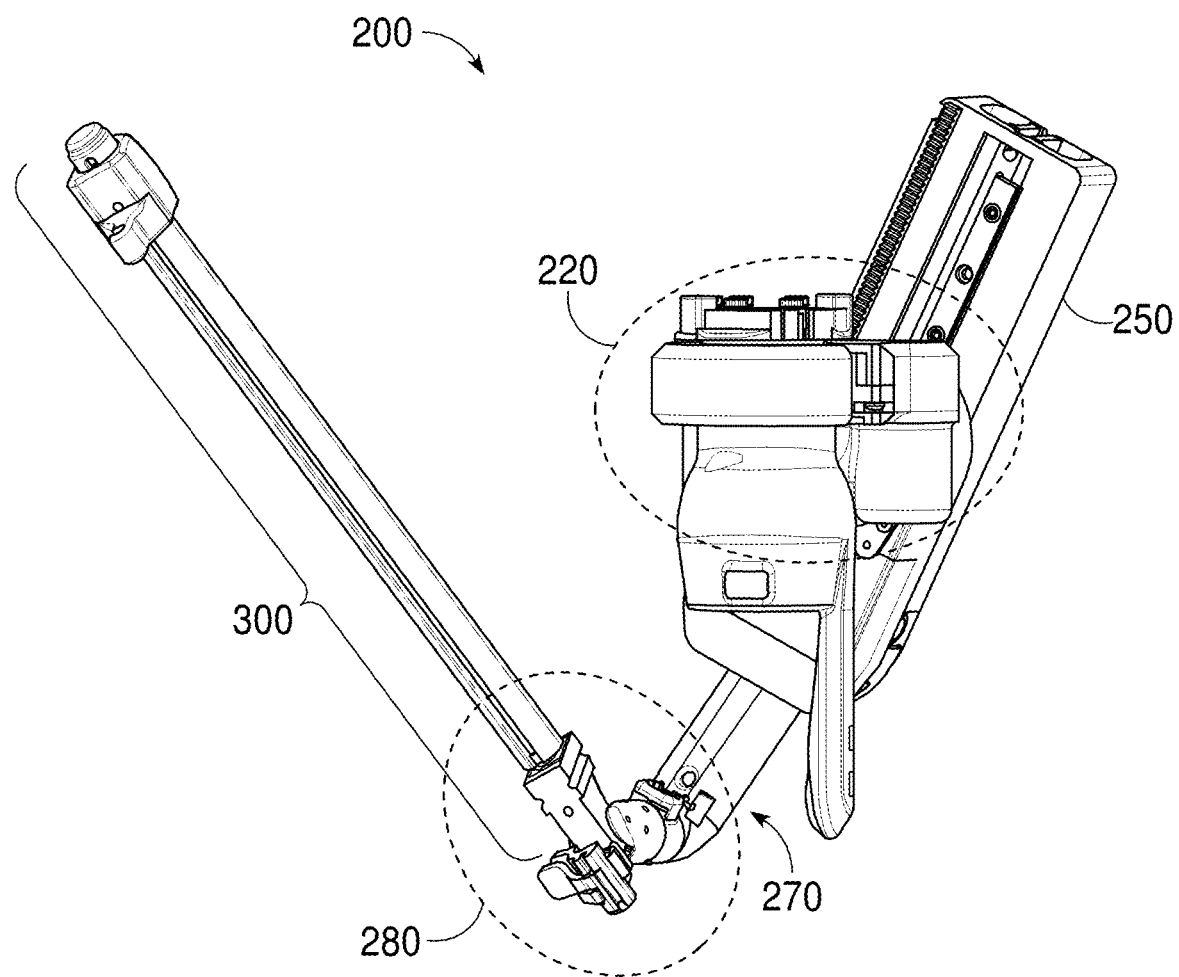
Figure 2B:
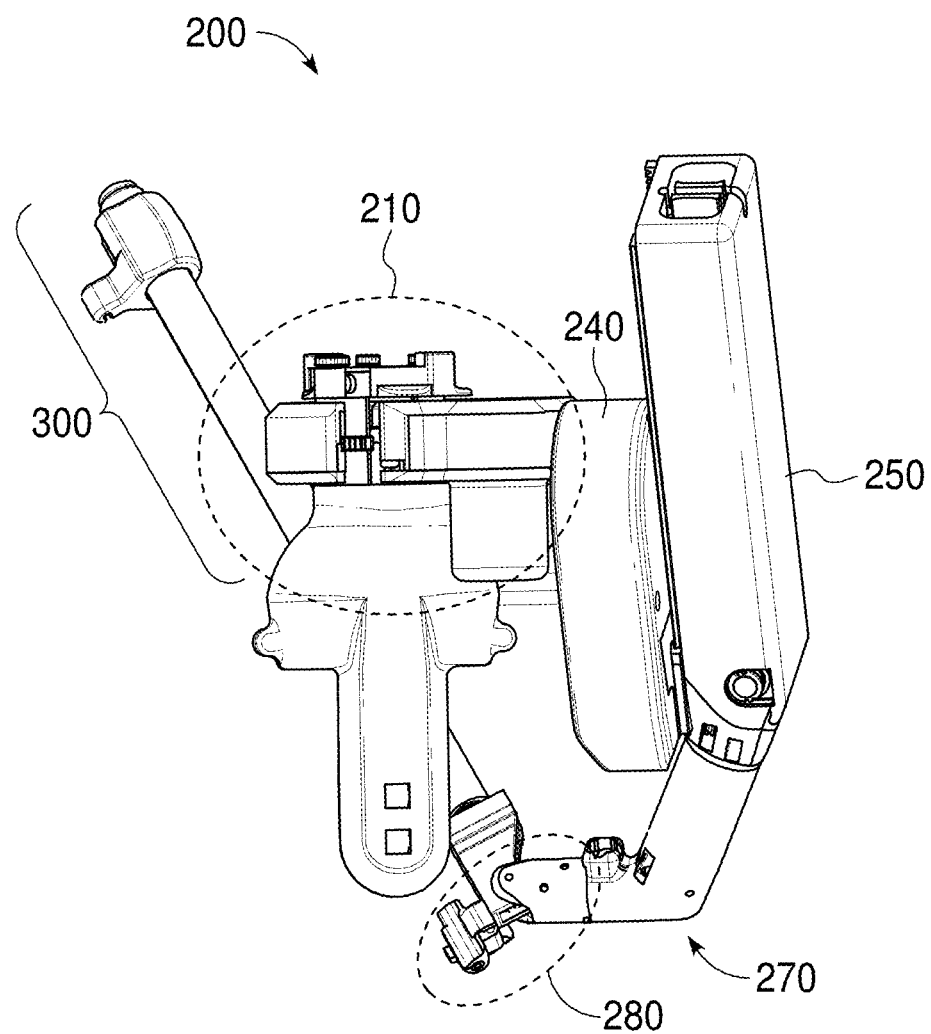
Figure 2C:
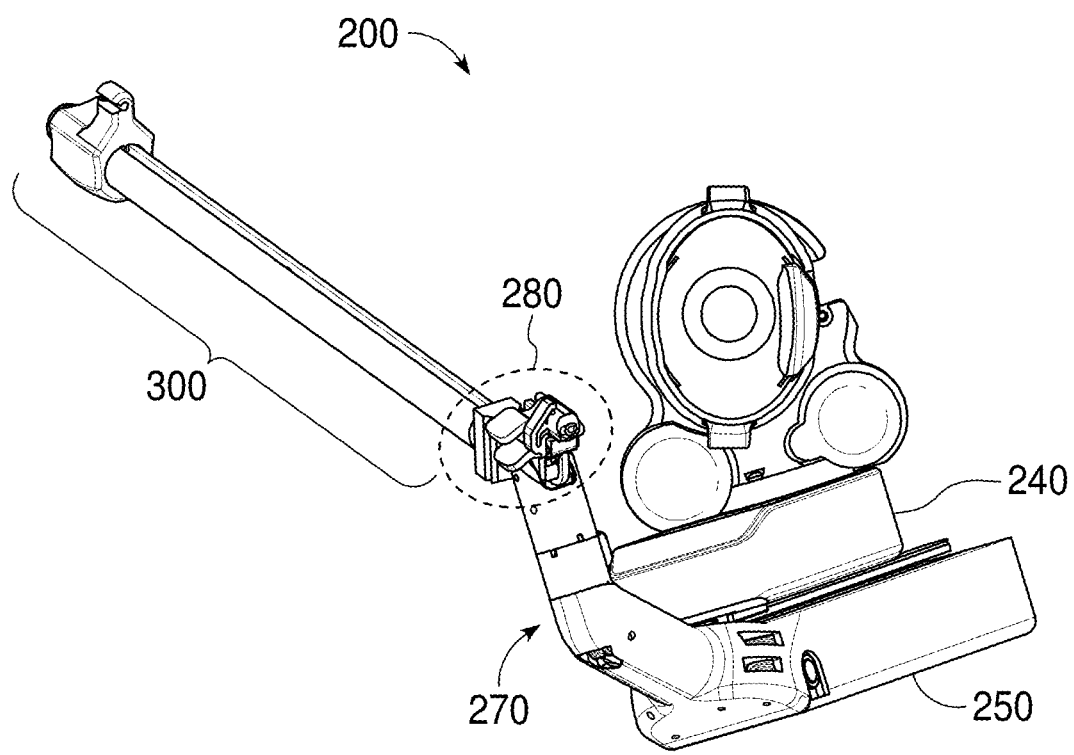
Figure 2E:
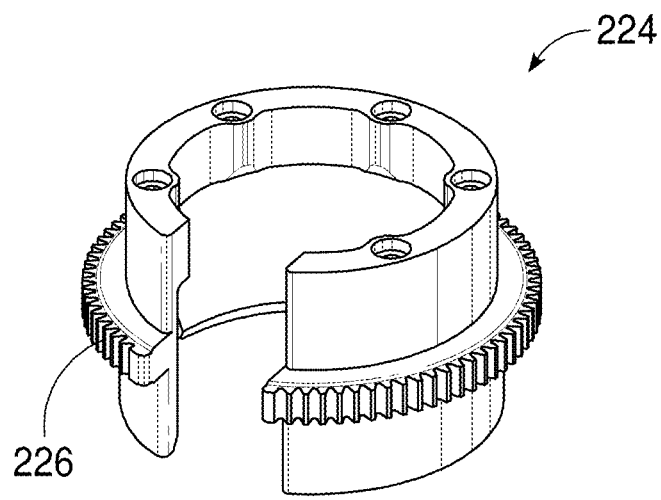
Figure 2F:
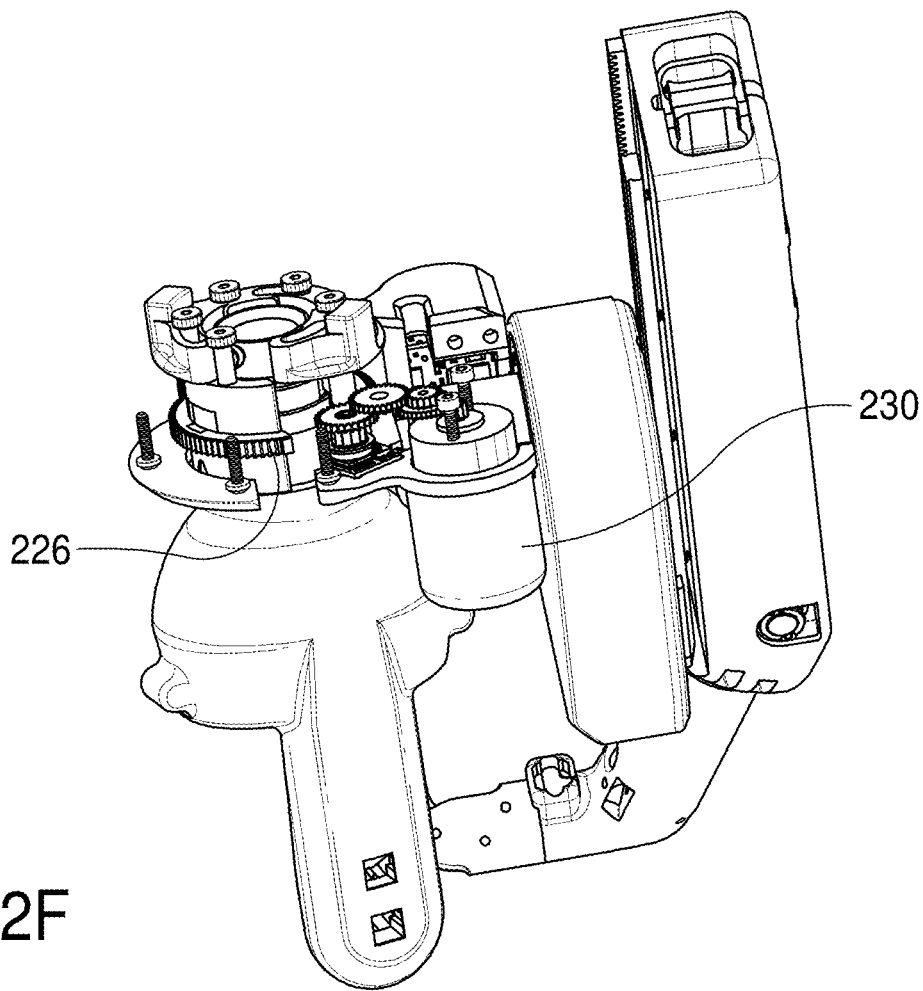
Figure 2G:
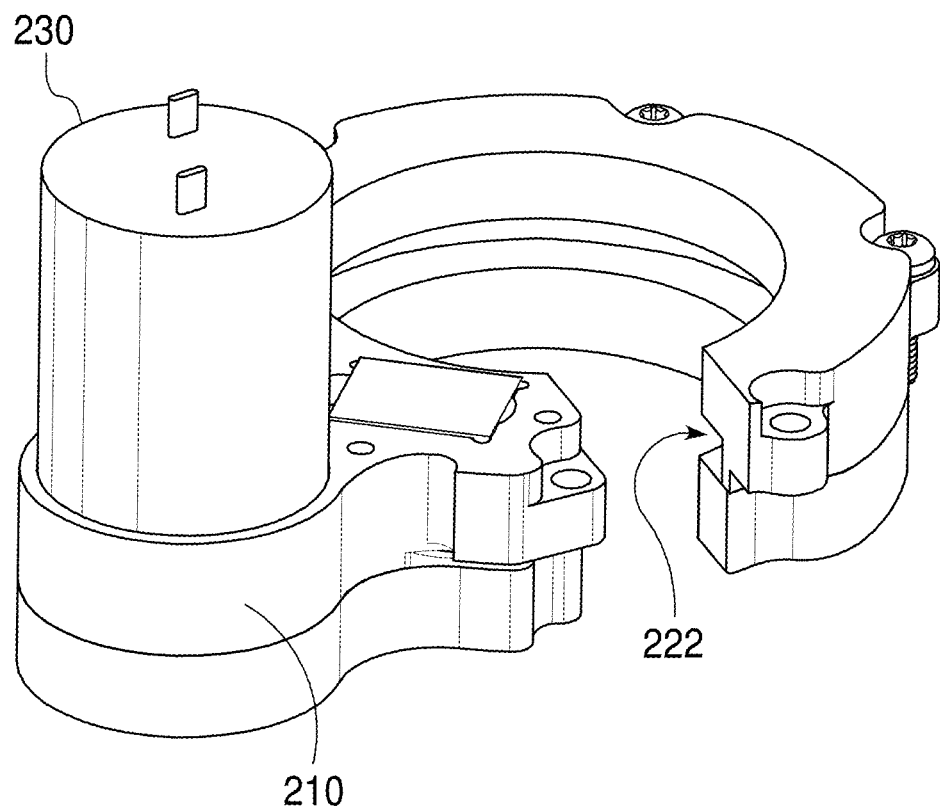
Figure 2H:
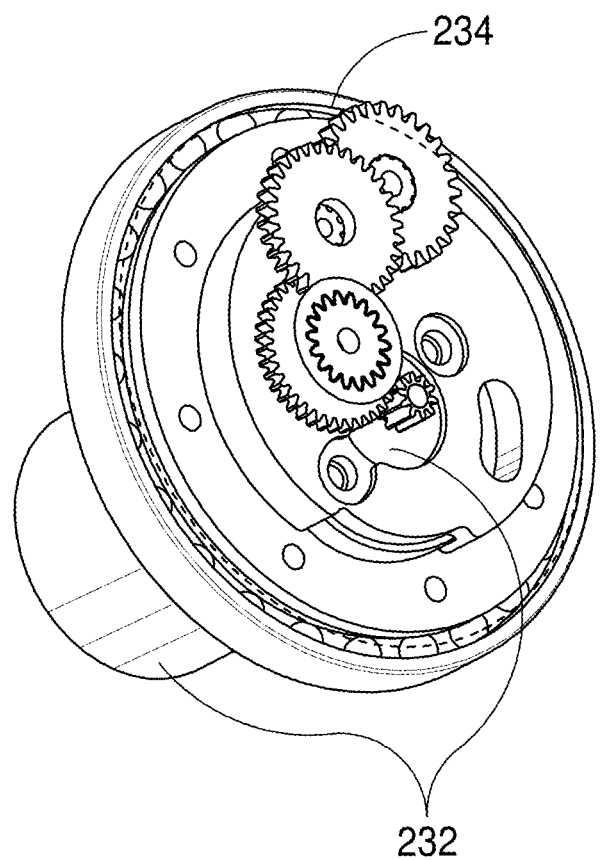
Figure 2I:
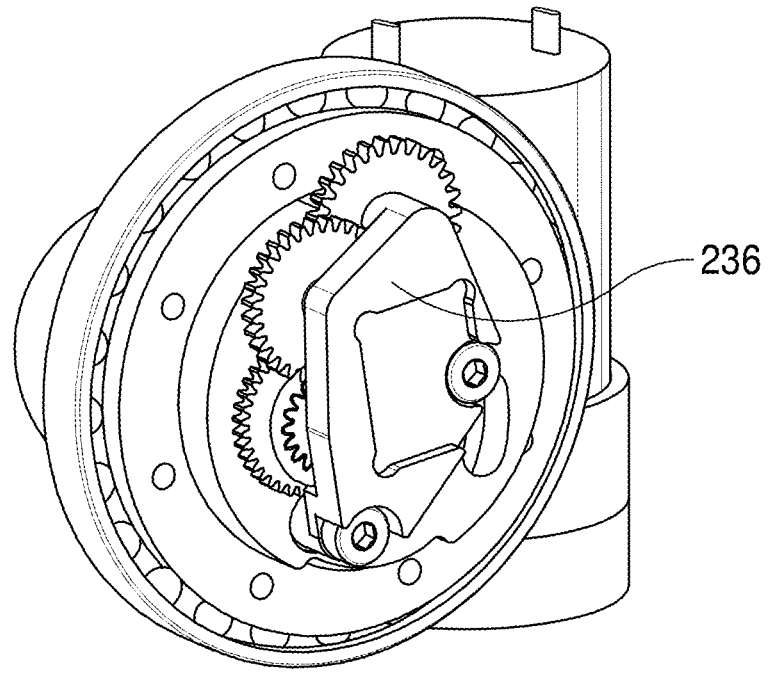
Figure 2J:
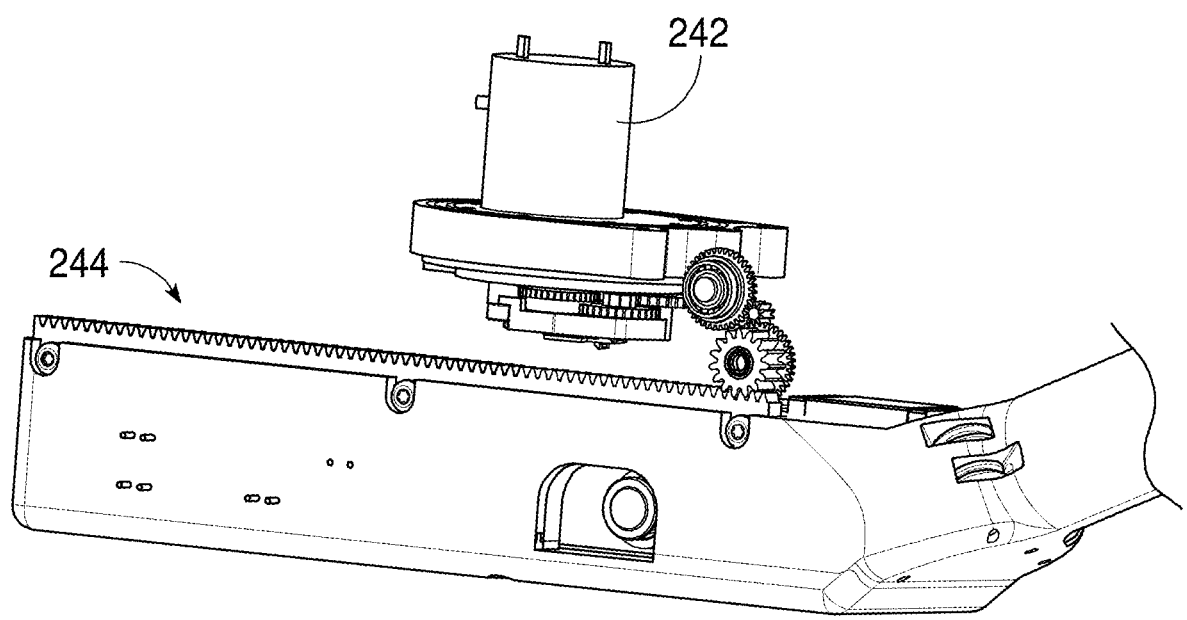
Figure 2K:
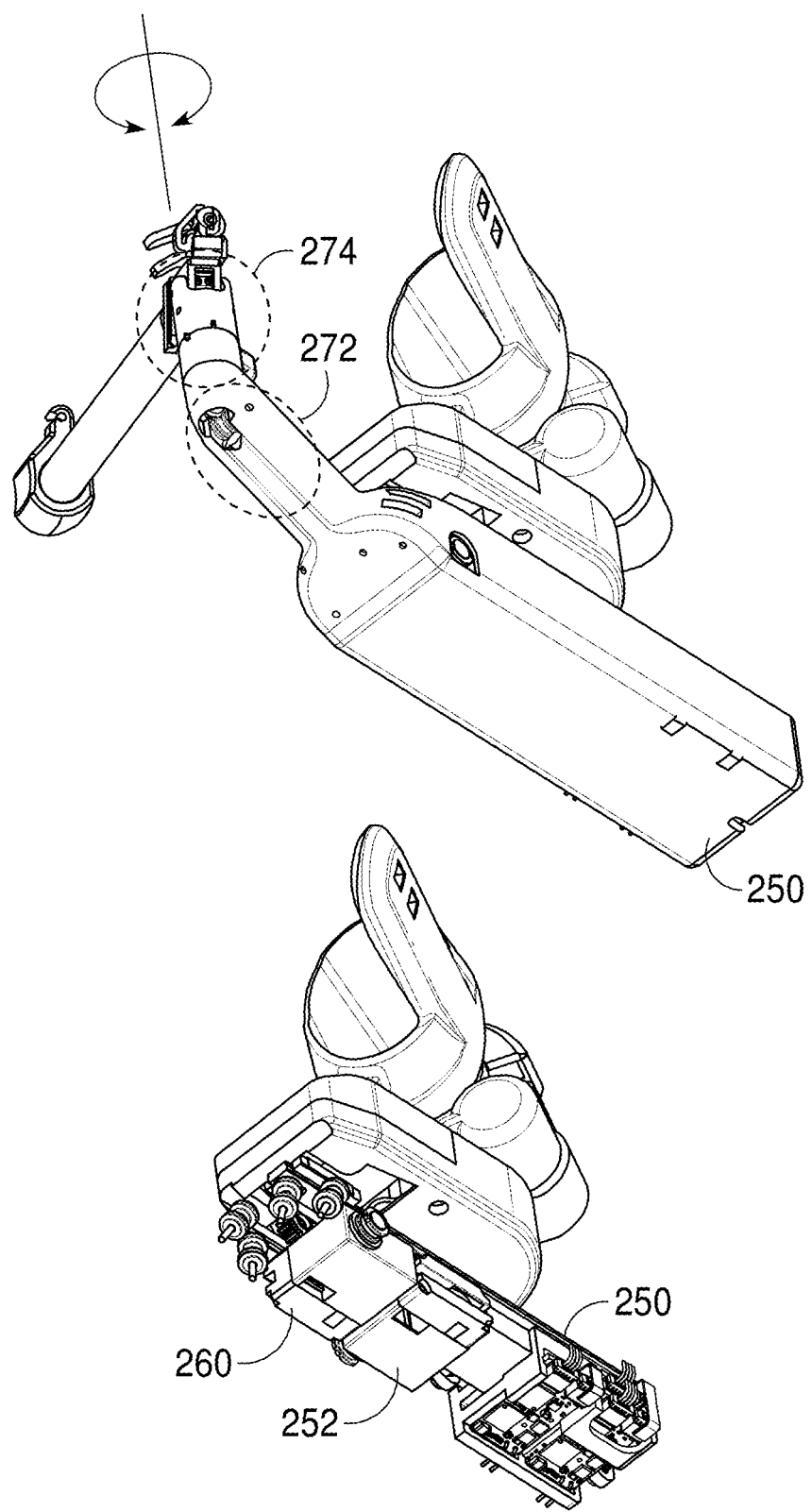
Figure 2L:
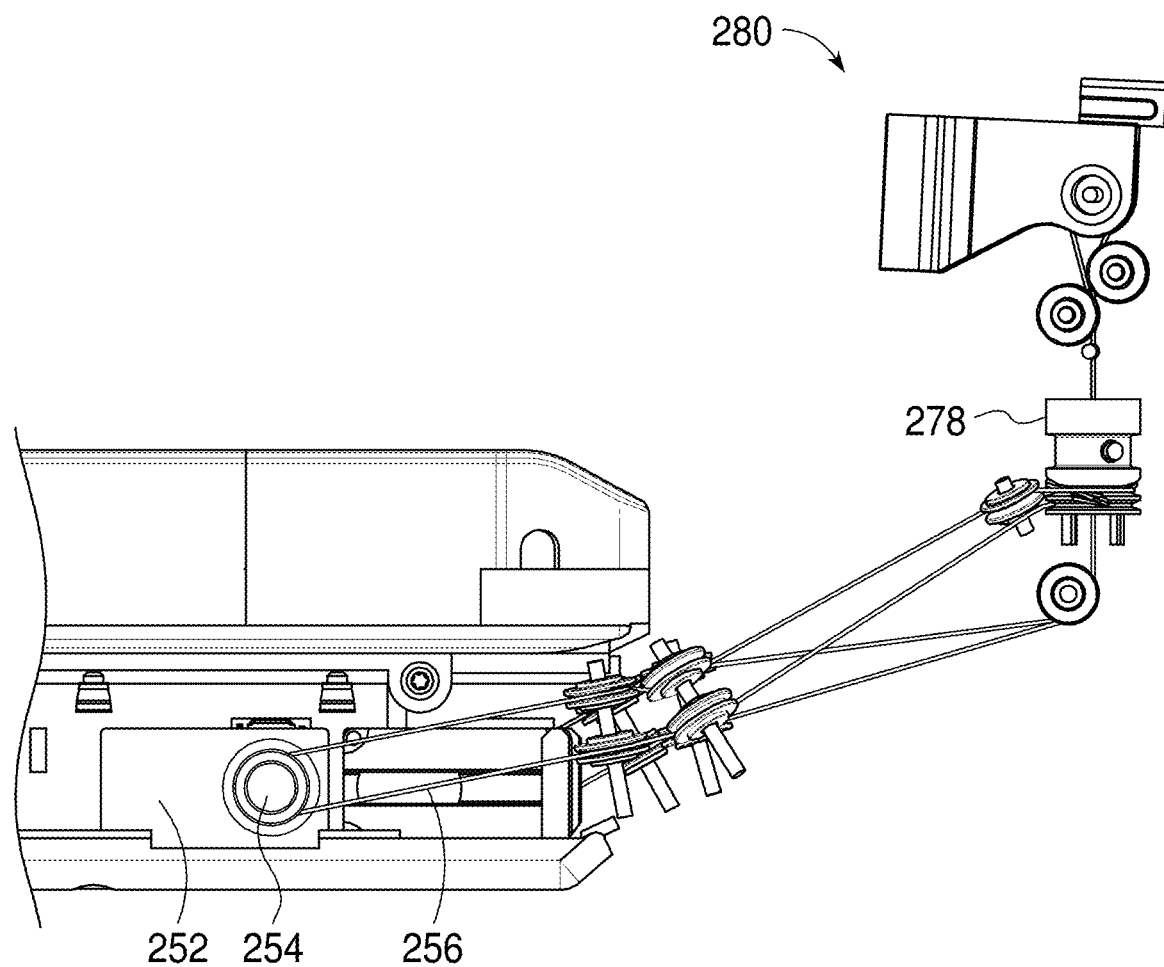
Figure 2M:
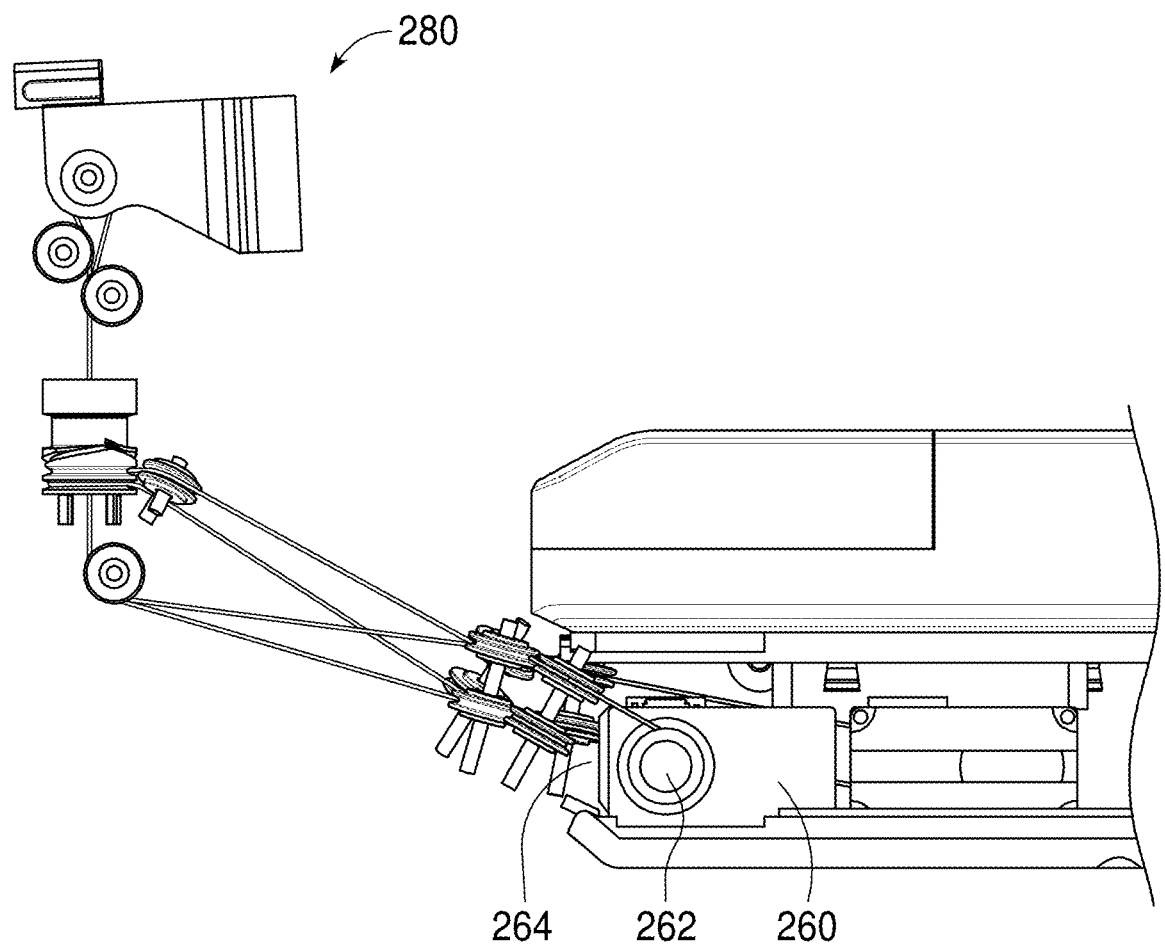
Figure 2O:
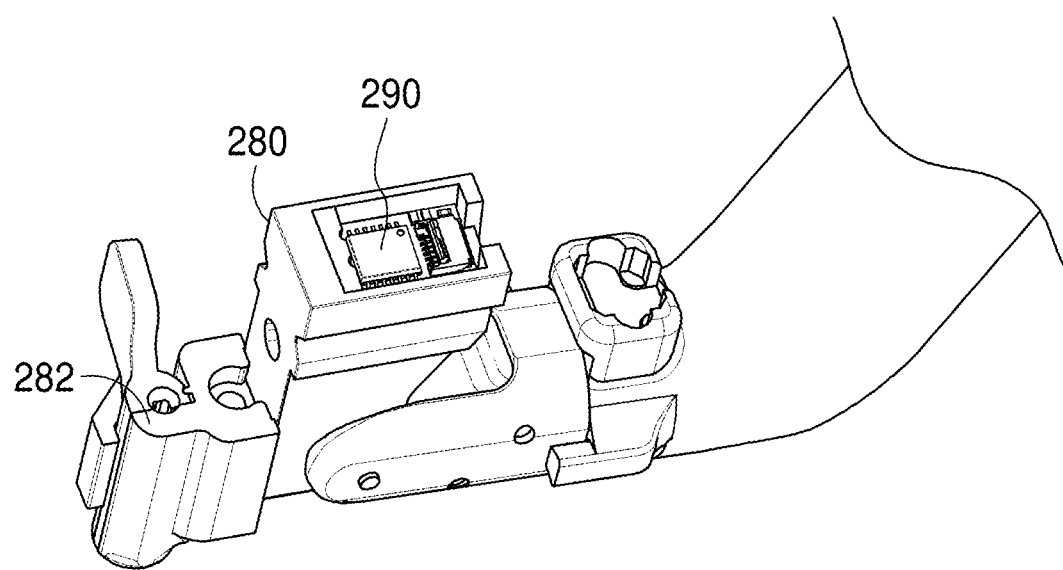
Figure 201:
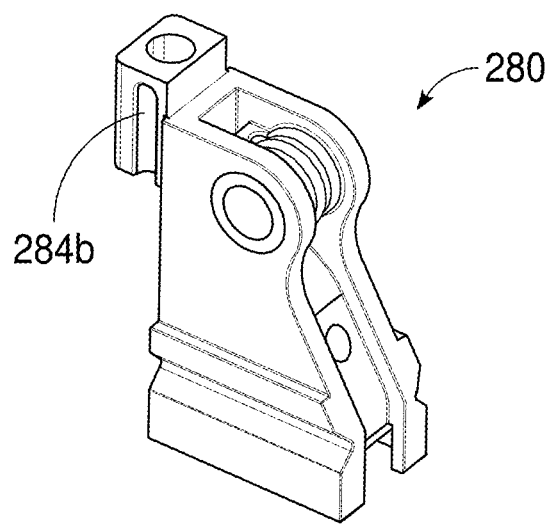
Figure 202:
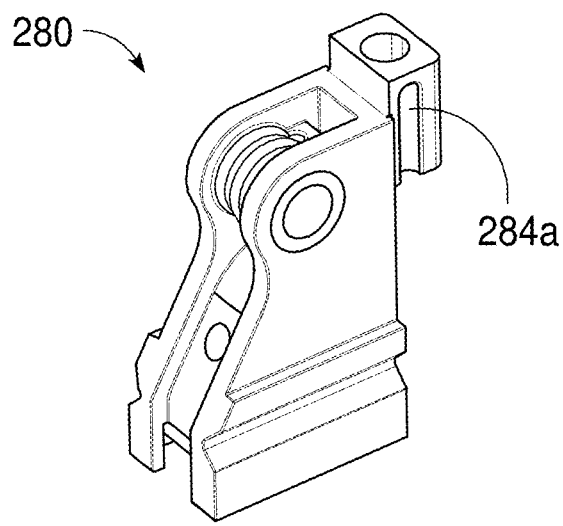
Figure 203:
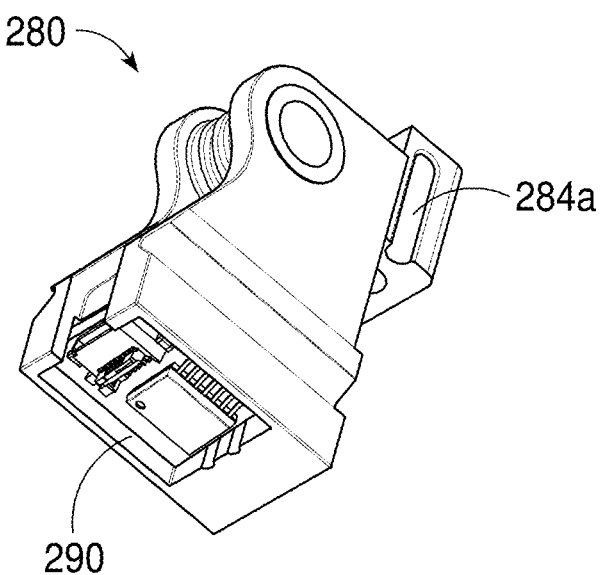

FIGS. 2A-2O3, inclusive, illustrate a modular robotic assembly 200 including a first enclosure 210, a second enclosure 240, a third enclosure 250, an elbow assembly 270, and interface 280.

First Enclosure 210 includes a receptacle 212 within which a body of an Imaging Device (e.g., ultrasound probe) may be placed and against an inner surface 113 of receptacle 212. Receptacle 212 includes a button holder 214 and an opening 215 through which electrical cords of Imaging Device may extend.

First Enclosure 210 includes a spur casing 216 having an opening 218 and an inner surface with a circular groove 222. Spur casing 216 is adapted to receive ring 224 configured with a spur 226 extending away from an outer surface of ring 224, wherein gear teeth of spur 226 are adapted for placement within circular groove 222. The depth of circular groove 224 exceeds the length of gear teeth to ensure the gear teeth 228 rotate within circular groove 224 without teeth engagement as ring 224 rotates within spur casing 216.

Ring 224 is configured to receive and secure to an outer surface of receptacle 222. Enclosure 210 includes a first rotary motor 230 rotationally coupled with gear teeth 228 that, when powered, in enabled to drive a rotation of an Imaging Device secured to receptacle 212 about spur casing 216.

First Enclosure 210 includes a second rotary motor 232 and a circular opening 234 within which a gearbox housing 236 is secured. When powered, second rotary motor 232 in enabled to drive a rotation of a US probe secured to receptacle 212 about circular opening 234.

Referring to FIG. 2J, second enclosure 240 (not shown) includes a rotary motor 242 and a gear rack 244 which form a rack-and-pinion assembly to convert rotary motion produced by the rotary motor 242 into linear motion to linearly drive the elbow 270 and interface 280 toward and away from enclosure 240.

Referring to FIGS. 2M-2K, inclusive, third enclosure 250 includes a roll servo motor 252, a pitch servo motor 260, and an elbow 270 with a stationary portion 272 and a rotatable portion 274 to which an interface 280 may be coupled. Roll servo motor 252 includes a spool 254 to which both ends of a cable 256 are connected. Cable 256 runs along a series of roll pulleys arranged within elbow 270 as it is routed to and from a spool 278 that is secured within rotatable portion 274 of elbow 270. When powered, roll servo motor 252 applies a rotational force to spool 254 in one direction, a force of tension is applied to one end of the cable which, through cable transmission, imparts a roll motion to spool 278, rotatable portion 274, and interface 280; likewise, when a rotational force is applied by roll servo motor 252 in the opposite direction, a force of tension is applied to the other end of the cable which imparts a roll motion in the opposite direction.

Pitch servo motor 260 includes a spool 262 to which both ends of a cable 264 are connected. As observed, cable 264 runs along a series of pitch pulleys arranged within elbow 270 as it is routed to and from interface 280. When powered, pitch servo motor 260 applies a rotational force to spool 262 in one direction, a force of tension is applied to one end of the cable which, through cable transmission, imparts a pitch motion to interface 280; likewise, when a rotational force is applied by pitch servo motor 260 in the opposite direction, a force of tension is applied to the other end of the cable which imparts an opposite pitch motion.

It should be noted that, although the forces created through roll servo motor 252 and pitch servo motor 260 have been transmitted through cables routed along arrangements of pulleys, the embodiments disclosed herein are not limited to cables. For the purpose of illustration and not of limitation, rods and linkages may be employed or any other means for force transmission to induce the roll and pitch motions.

Referring to FIGS. 2O-2V3, inclusive, interface 280 includes a hinge pin 282 and hinge pin recesses 284a and 284b to provide a mating surface to which hinge pin 282 may be coupled. Hinge pin 282 provides a grip/guide/release mechanism to control the insertion and release of an instrument. It may include a passive mechanism that relies on the actuator of the robotic arm to move while allowing the HCP to manipulate the instrument.

As shown, hinge pin 282 includes an aperture 286 for receiving an instrument (not shown). In some embodiments, hinge pin 282 may comprise a tab that may be pressed to insert and release instrument (not shown). In some embodiments, interface 280 may include an encoder 290 for measuring rotational movement of an inner shaft with helical groove. In some embodiments, the encoder 290 could be magnetically engaged with an end of inner shaft with helical groove 310.

In some embodiments, instrument guide assembly may be coupled with an actuator to provide an automated insertion of the instrument into a person's body. Instrument guide assembly includes a coupler 302, sleeve 304, an outer shaft 306 with a helical groove 310, and inner shaft configured with a helical groove 310.

As shown in FIGS. 2R1-2R3, coupler 302 includes rails 302a and 302b, and opening 302c through which one end of the inner shaft 308 with a helical groove 310 engages with encoder 290. As shown in FIGS. 2S1-2S2, coupler 302 (not enumerated) is configured to slidably engage interface 280 (not enumerated, see FIGS. 2Q1-2Q2) along with the slidable engagement of hinge pin 282 (not enumerated, see FIGS. 2Q1-2Q2).

As shown in FIGS. 2U1-2U2, sleeve 304 may comprise an interface 312, an inner surface 314 for a slidable engagement with outer shaft 306, helical tracking pin 316, an arm 318 extending in an opposite direction away from helical tracking pin 316, a V-shaped groove 320 through which a HCP may insert an instrument guide (not shown) may be received into aperture 322. As shown, aperture 322 is aligned with aperture 286 for receiving an instrument extending the distance between sleeve 304 and interface 280.

This is illustrated in FIGS. 2V1-2V3 where a syringe 330 with plunger 332 and needle 334 extends between aperture 322 and aperture 286 (not shown) of hinge pin 282. FIG. 2V2 illustrates the downward travel of syringe 330, plunger 332, and needle 334 as helical tracking pin 316 slides within helical groove 310 to impart a rotation of the inner shaft 308, where encoder 290 captures the rotation through its magnetic engagement with the one end of the inner shaft 308. As a result of capturing the rotation, IMU 130 may determine the depth of the needle's travel. After the needle reaches its desired depth, a downward force may be exerted on the plunger 332 as shown in FIG. 2V3 to deliver the ingredients in the syringe.

Inner shaft 308 may comprise a sensing mechanism for measuring the depth that an instrument inserted through instrument guide (not shown). Because an instrument is inserted into the instrument guide (not shown), the instrument may be inserted into a person's body as the encoder measures its depth.

Sterile Boundary

Embodiments disclosed herein describe a sterile boundary (or sterile barrier), comprising one or more highly compliant (e.g., drape-like) sections and one or more rigid (e.g., plastic- or rubber-like) sections to limit transmission of particles from an image guided robotic intervention system ("IGRIS") (e.g., modular robotic assembly 200 or IGRIS 100). In some embodiments, sterile boundary may be used with modular robotic assembly 200 or IGRIS 100 discussed herein to maintain a sterile barrier between the HCP, patients, and all non-sterile equipment (e.g. ultrasound probe) during procedures.

The sterile boundary may couple to key features of the robotic device (e.g., modular robotic arm, or the robotic portions of IGRIS 100), and may include transparent elements to permit visualization of a screen/user interface and to allow touch signal to pass through it to enable interaction with a touchscreen. The sterile barrier may comprise integrated coupling gel. In some embodiments, the sterile barrier may also cover an instrument guide (e.g., a physical needle guide), or interface with a sterile guide tightly to create a sterile barrier.

In some embodiments, a sterile boundary may be used during every medical procedure. In some embodiments, the sterile boundary (or portions) may be disposable.

The specific interface between the IGRIS and the sterile instrument (e.g., needle) needs to be sterile, and rigidly in contact with the modular robotic arm (so that it can be steered by the robotic arm). In some embodiments, the sterile barrier may be coupled to the instrument guide (e.g., as one of the rigid sections). In some embodiments, the instrument guide may be attach-able to one of the rigid elements of sterile boundary.

In some embodiments, the rigid elements of the sterile barrier may attach to key features of the robotic arm, such as the Imaging Device head (e.g., ultrasound probe head), the robotic manipulator (e.g., needle targeting arm), instrument guide (e.g., a needle guide), a screen and/or user interface, or buttons.

In some embodiments, the sterile barrier and robotic device may have complementary features to support easy attachment and/or removal of the sterile barrier, such as insets into the housing of the robotic device and corresponding rigid features on the drape, snap fasteners on the robotic device and drape respectively, adhesives, elastic or magnets. These interface features may be related to the rigid features described above, or be part of the compliant portion of the drape.

In some embodiments, the sterile barrier comprises a rigid element that would act as an interface between the instrument guide and the instrument being inserted (e.g., a needle).

In some embodiments, the rigid features of the barrier may include one or more highly transparent elements (glass, plastic, polycarbonate, etc.) to support visualization of a screen/user interface that is included in the robotic device, and to allow capacitive or resistive touch signal to pass through it so that a user can interact with user interfaces included in the robotic device. In some embodiments, the highly transparent elements may be used for other aspects, including sensors, lights, cameras, or other components that may require transparency. In some embodiments, the highly transparent elements may be compliant components of the drape itself.

In some embodiments, the sterile barrier may include integrated cartridges, pockets, or free-floating acoustic coupling gel, which additionally may be enabled to come in contact with the robotic device via removal of adhesive coverings, pull tabs, etc. Integration of a gel cartridge, pocket, or even free-floating gel in the housing of the drape may enhance workflow dramatically. In some embodiments, the pockets may be covered (e.g., using pull-tabs or adhesive layers), such that the user remove the cover adhesive layer and expose the gel, thereby allowing contact between the probe and the gel, and thus ensuring acoustic coupling.

In some embodiments, the sterile barrier may include an integrated instrument guide. For example, the sterile barrier with instrument guide may be used with embodiments of IGRIS 100 or modular robotic arm without an instrument guide. In some embodiments, the sterile barrier may comprise unique features on the instrument guide and/or robotic arm to ensure the instrument guide is properly secured to the robotic arm and that the system has an accurate understanding of the location of the instrument (e.g., needle), and the trajectory it would follow when inserted into an object (e.g., anatomy). In some embodiments, sterile barrier may include an integrated instrument guide and an integrated instrument. For example, a needle with syringe preloaded may be incorporated into a sterile barrier with integrated instrument guide as one piece.

Figure 3A:
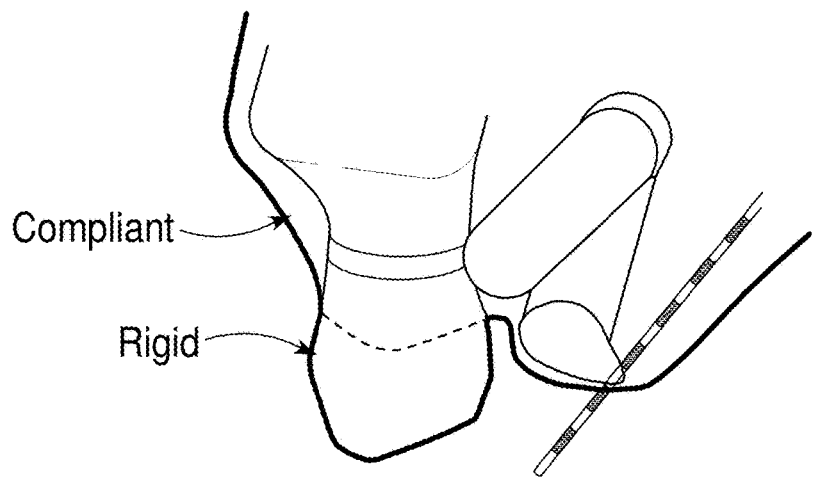
FIGS. 3A-3B, inclusive, illustrate embodiments of a sterile barrier

Referring now to FIG. 3A, an instrument guide and a sterile barrier having one or more highly-compliant coverings (e.g., drape(s)) and one or more rigid (i.e., plastic or rubber-like) sections having rigid features are illustrated to limit transfer of particles from the robotic manipulator to the patient. In some embodiments, the sterile barrier and robotic manipulator may have complementary features to support easy attachment and/or removal of the sterile barrier such as, but not limited to, insets into the housing of the robotic device and rigid features complementary to the insets in the drape, snap fasteners on the robotic arm and drape, adhesives, and magnets. These interface features may be part of the rigid features and/or highly compliant sections of the barrier.

In some embodiments, the sterile barrier may include an instrument guide as disclosed above by, for example, integrating a sterile instrument guide into the drape. In embodiments in which the robotic arm may have the instrument guide integrated into the robotic manipulator, the rigid section of the sterile barrier could interface between the instrument guide and the instrument as it is being inserted as disclosed above.

Figure 3B:
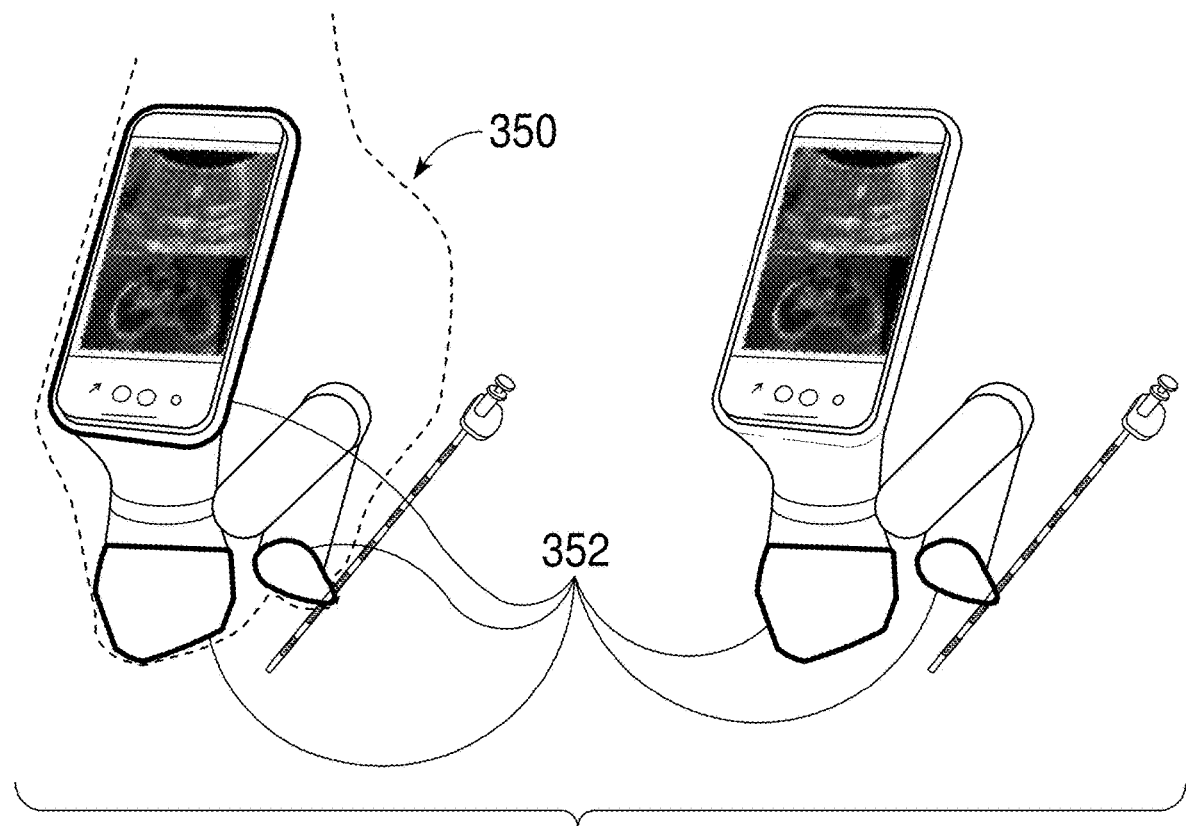

Referring now to FIG. 3B, exemplars of a sterile barrier are illustrated. As shown, dashed line 350 represents the outside edge of the highly-compliant section, and lines 352 represent the boundaries of the rigid section; here, rigid sections are coupled to the US transducer, user interface/screen, and distal end of a robotic manipulator. Intersections of the orange and yellow lines represent places where compliant and rigid sections are coupled to one another. As shown in the right-hand illustration, the sterile barrier may cover only the US head and distal end of the robotic manipulator.

In some embodiments, sterile barrier may be shaped similar to a pair of pants, with one leg of the "pants" for the Imaging Device, and the other leg for the modular robotic assembly. In other embodiments, two sterile barriers may be utilized (one for the Imaging Device and one for the robotic arm), and the sterile barriers may be attached in a secure manner. In some embodiments, sterile barrier may be entirely compliant, such that the instrument guide clips over the compliant sections and sandwiches the barrier between the instrument guide and the distal end effector of the robot manipulator.

Instrument Guide

Embodiments disclosed herein describe an instrument guide. The instrument guide may be used in robotic percutaneous procedures which use a robotic arm (e.g., IGRIS 100 or modular robotic arm) to guide or drive an instrument (e.g., a needle) through the skin to target anatomy.

In some embodiments, a custom sterile boundary for the instrument guide may be created for the instrument guide, and may include a factory integrated model, or a model which can be affixed prior to use. In some embodiments, the instrument guide may be disposable for sterility.

In some embodiments, the instrument guide may include grip/guide/release capabilities. The instrument guide may grip an instrument (e.g., a needle) securely so the user may perform various tasks, such as remove accessories from the needle (e.g. a syringe) or perform ancillary tasks while constraining axial and rotational motion. The instrument guide may guide the instrument along an axial trajectory to hit a target, and allow rotation. The instrument guide may release the instrument while it is inserted in the patient to allow subsequent procedural tasks without the robotic arm or IGRIS.

In some embodiments, instrument guide may measure the depth of the needle to provide feedback to the user and/or robotic system.

In some embodiments, instrument guide may support the instrument (e.g., needle) in a manner that allows the user to Backdrive the robotic arm to manually and collaboratively adjust the needle trajectory, or interact with the robot in a haptic manner.

In some embodiments, the sterile boundary may integrate as an interface between a sterile instrument guide and a non-sterile modular robotic arm (or IGRIS), covering the modular robotic arm (or IGRIS) and exposing the sterile instrument guide, essentially allowing for an entirely sterile device using the sterile needle guide functionality.

Referring now to FIGS. 2T1-2T4, an illustration of an embodiment of a detachable instrument guide is shown. Instrument Guide comprises an outer shaft 306, a carriage 304, a coupler 302, a helical groove 308, an inner shaft 310, and roller bearings 312a and 312b. In some embodiments, the detachable instrument guide may mate with interface 280 and the grip/guide/release mechanism via coupler 302. Additionally, the detachable instrument guide may mate with robotic manipulator via couple 302.

In some embodiments, the grip/guide/release mechanism may be a passive mechanism that relies on the actuator of the robotic arm to move. In some embodiments, the instrument insertion motion may be arrested by braking the carriage motion rather than gripping the instrument itself.

Coupler 302 may comprise mating features (e.g., magnets, screw, or other mating interfaces known to one of skill in the art) be used to couple Instrument Guide to a robotic assembly (e.g., modular robotic arm or IGRIS 100). Coupler 302 may also comprise an encoder read head to measure the carriage motion as well as an actuator to actuate the grip/guide/release mechanism.

Instrument Guide may comprise carriage 304 that may run along a linear axis to fix the instrument (e.g., needle) at the most proximal part of the needle near the instrument/accessory (e.g., syringe portion of the needle instrument). This beneficially allows forces at the accessory to be transferred to the arm in a way that doesn't rely on the structural integrity of the needle itself. This is particularly useful for small diameter needles (e.g. 27 gauge) which are highly compliant.

Instrument Guide may comprise a sensing mechanism to measure the depth that the instrument is inserted through the grip/guide/release mechanism. In one embodiment, the sensing mechanism may comprise a lead screw 308 coupled to a sensor (e.g., an encoder). The sensing mechanism may detect instrument (e.g., needle) depth using the carriage's linear motion drives a lead screw that spins an encoder magnet or disc. For example, the transition from FIG. 2V1 to 2V2 illustrates the carriage's downward linear motion. Further, the transition from FIG. 2V2 to 2V3 illustrates the needle insertion downwards. The encoder may be read in a non-contact way by an encoder read head in the robotic arm and may be performed optically or magnetically. In some embodiments, sensing mechanism may include a telescoping insertion axis for measuring depth or inserting a needle. This allows for the measurement to happen across the sterile barrier.

In some embodiments, the encoder assembly attached to the lead screw may be replaced with an actuator for servo control to allow for active insertions.

In some embodiments, instrument guide may comprise a stabilizing structure that runs along the length of the instrument to stabilize instruments (e.g., needles) that may deform (e.g., bend) when manipulated. In some embodiments, the stabilizing structure may also comprise a sensing mechanism to measure insertion depth of the instrument using a variety of depth measurement techniques (e.g., using cables, belts, leadscrews, rack and pinion mechanisms, or others known of one of skill in the art. In some embodiments, sensing mechanism may include a telescoping insertion axis for measuring depth or inserting a needle. In some embodiments, the stabilizing structure may be a variable length to support different instrument sizes, may be expandable (e.g., to support longer needles), or collapsible (e.g., to support shorter needles), or may come in multiple lengths. In some embodiments, the stabilizing structure may be modular and attached when needed.

The stabilizing structure may also comprise motorization capabilities, which may facilitate actuation of insertion of the instrument, and/or roll of the instrument. For example, the instrument may be rolled through the use of rollers along the shaft rolling a mechanism clamped to the shaft of the needle.

Calibration

IGRIS 100 may perform an initial calibration using Software 120 which performs an optimization and synchronization of the IGRIS 100 hardware components, including Imaging Device 146, Robotic manipulator 126, and Instrument Guide 128. Calibration may be necessary because the settings, operation, and specifications of various Imaging Devices 146 may slightly differ, and IGRIS 100 may need to compensate for the differences. Calibration may determine the location of the real-time image from the raw video feed input from Imaging Device 146. Calibration may then determine the conversion from image pixel space to real world coordinates (e.g., millimeters or mm). These transformations may be referred to as the scale and offsets, or may be more complex to account for image deformation. For example, calibration may compute an accurate mathematical representation or transformations between components of the Imaging Device 146, Robotic manipulator 126, and Instrument Guide 128. Calibration may be performed during manufacture and assembly, prior to use, or during use. Calibration may also be performed automatically by Software 120.

IGRIS 100 includes various types of calibration including (1) Robotic manipulator 126 to Instrument Guide 128 calibration, (2) Imaging Device 146 to Robotic manipulator 126 calibration, and (3) Real-time Images (acquired from Imaging Device 146) to Imaging Device 146.

Robotic manipulator 126 to Instrument Guide 128 calibration involves computing the coordinate transformation between components of the Robotic manipulator 126 with components of the Instrument Guide 128 as a function of manipulator geometry and joint angles. In some embodiments, Instrument Guide 128 may be coupled, or attached, on one end of the Robotic manipulator 126. In such an embodiment, the calibration is performed between the base of the Robotic manipulator 126 and the Instrument Guide 128 (e.g., proximal and distal ends of the Robotic manipulator 126). This is generally known as kinematics to one of skill in the art.

Imaging Device 146 (e.g., the probe of an ultrasound) to Robotic manipulator 126 (e.g., robotic arm) calibration performs a coordinate transformation between the Imaging Device 146 and Robotic manipulator 126. These coordinate transformations may vary based on probe housing and robot adapter geometry.

Real-time Images (acquired from Imaging Device 146) to Imaging Device 146 calibration maps image locations in pixels, to locations under the Imaging Device 146 in distance (e.g., millimeters). The X-Y axis plane may be mapped based on pixels, voxels, blocks, measurements (e.g., inches, centimeters, millimeters ("mm")), or other mapping means that may be understood by one of ordinary skill in the art.

In some embodiments, a calibration station may be available for use prior to, or during use, to quickly and easily calibrate the IGRIS components (e.g., Imaging Device 146, Robotic manipulator 126, and Instrument Guide 128). IGRIS 100 may be placed on, inserted into, or connected to the calibration station for detection. The calibration station is able to detect the different makes and models of the IGRIS components and load an appropriate calibration profile for the specific IGRIS components. In some embodiments, the Display Unit 116 of IGRIS 100 may receive input to manually identify the makes and models of the IGRIS components, such as imaging device 146 (e.g., including a drop down list, or manually typing in such information). In some embodiments, the calibration station may receive zero external inputs, and calibrate based on an automated mask of the ultrasound and a live calibration, obviating the need for the user to configure the system manually. Further a change detector may be employed outside of the mask to ensure the system faults if a setting is changed.

In some embodiments, IGRIS 100 may perform a calibration where IGRIS 100 may detect the makes and models of the components, however, IGRIS 100 may be unaware of its settings. IGRIS 100 may use the calibration station to compute the calibration. In some embodiments, IGRIS may interface with the imaging device by capturing video from the imaging device's graphical user interface. The graphical user interface includes indications of settings and the live ultrasound image. An automated mask of the ultrasound may be extracted as a region of interested to compute image (pixels) to imaging device 126 (mm) calibration using the calibration station. Additionally, IGRIS 100 may analyze Imaging Device 146 (e.g., the video or real-time images from the GUI) to detect any changes or errors. For example, IGRIS 100 may monitor and analyze the video or real-time images from an ultrasound, and may assume the settings of Imaging Device 146 may stay constant unless there is a change in User Interface 132). Once calibrated, IGRIS 100 shall store its settings and assumes the settings stay constant. In the event IGRIS 100 detects a change in the User Interface 132 outside of the real-time image pixels, IGRIS 100 may assume the settings have changed, throw a fault or indicate an error has occurred, and assume it is out of calibration. In some embodiments, the IGRIS employs naïve heuristics (e.g. pixel by pixel change detector) to detect GUI changes. At this point, IGRIS 100 may need to be calibrated again.

In some embodiments, the calibration station may comprise a known object (e.g., where the measurements of any internals of the object are already calculated and known to IGRIS). IGRIS 100 may be calibrated by performing a simple scan of the known image (using Imaging Device 148), and the proper measures and calculations may be derived based on the scan to the known object. The calibration station may save information regarding prior calibrations performed and generate new profiles for various components or improve existing profiles based on the information. The calibration station may also use computing techniques (e.g., Machine Vision, Image Analysis, Artificial Intelligence ("AI"), Machine Learning ("ML")) to improve future calibrations.

Calibration may involve IGRIS 100 performing a functional calculation to map the relationship between Imaging Device 146 and the location of internals of a known object (e.g., a spheroid, where the center of the spheroid is known to be at location (x, y)) and digitally map feature locations in the known object to the pixelized representation of the object (e.g., a real-time image scanned from Imaging Device 146). In other words, IGRIS 100 may scan, using the Imaging Device 146, a known object (where the location of its internal geometry has already been calculated and stored) to compare the real-time image with the stored settings of the known object. Because the calibration station is a known object (e.g. by manufacture or previous measurement), IGRIS 100 has already identified and determined the relational distances of different objects inside the station. By correlating the known object locations in mm with the image of those objects in pixels from the calibration scan (e.g., using the uncalibrated Imaging Device 146), IGRIS 100 may now properly pixel locations in the image to physical locations under the probe. Thus, the uncalibrated Imaging Device 146 is now calibrated with IGRIS 100.

IGRIS 100 maps the center of a spheroid where its center point is known to be at location (x,y) to the corresponding pixel locations of the center point (px, py). IGRIS 100 may map additional known points to corresponding pixel locations, and may compute the mapping using techniques, such as an affine transformation, or other techniques known to one of skill in the art.

In some embodiments, IGRIS 100 may be pre-calibrated during manufacture to obviate the need for the user to perform calibration. In some embodiments, IGRIS 100 may perform calibration prior to each use (e.g., prior to each procedure). In some embodiments, a software API may be exposed by the imaging device 126 such that IGRIS may simply query the API to obtain setting information.

In some embodiments, IGRIS 100 may utilize calibration profiles that are pre-generated for use for different Imaging Device 146 models. IGRIS 100 may automatically detect the make or model of a particular Imaging Device 146 along with its current settings, and Software 100 may load the appropriate profile for the specific make/model of the Imaging Device 146.

Figure 4A:
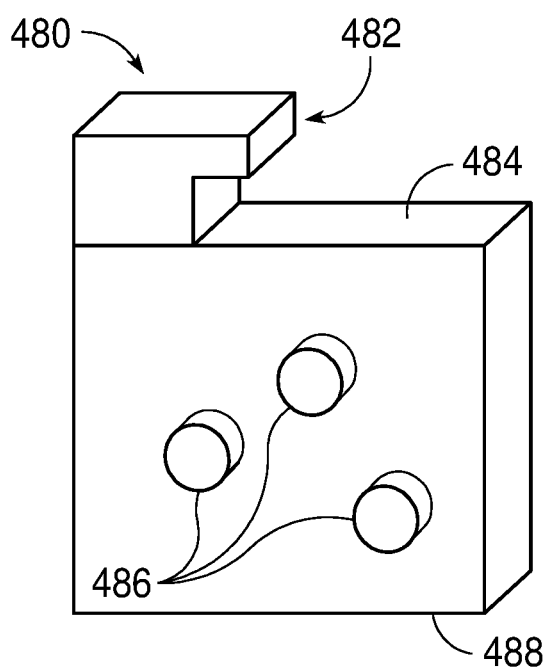
FIGS. 4A-4C, inclusive, illustrate embodiments of calibration performed on IGRIS.
Figure 4B:
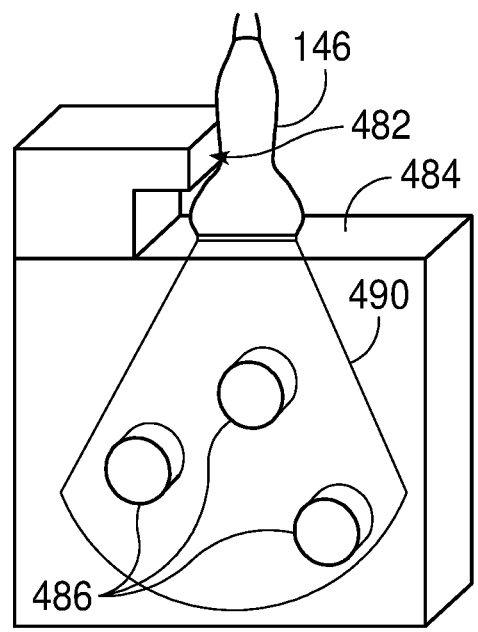
Figure 4C:
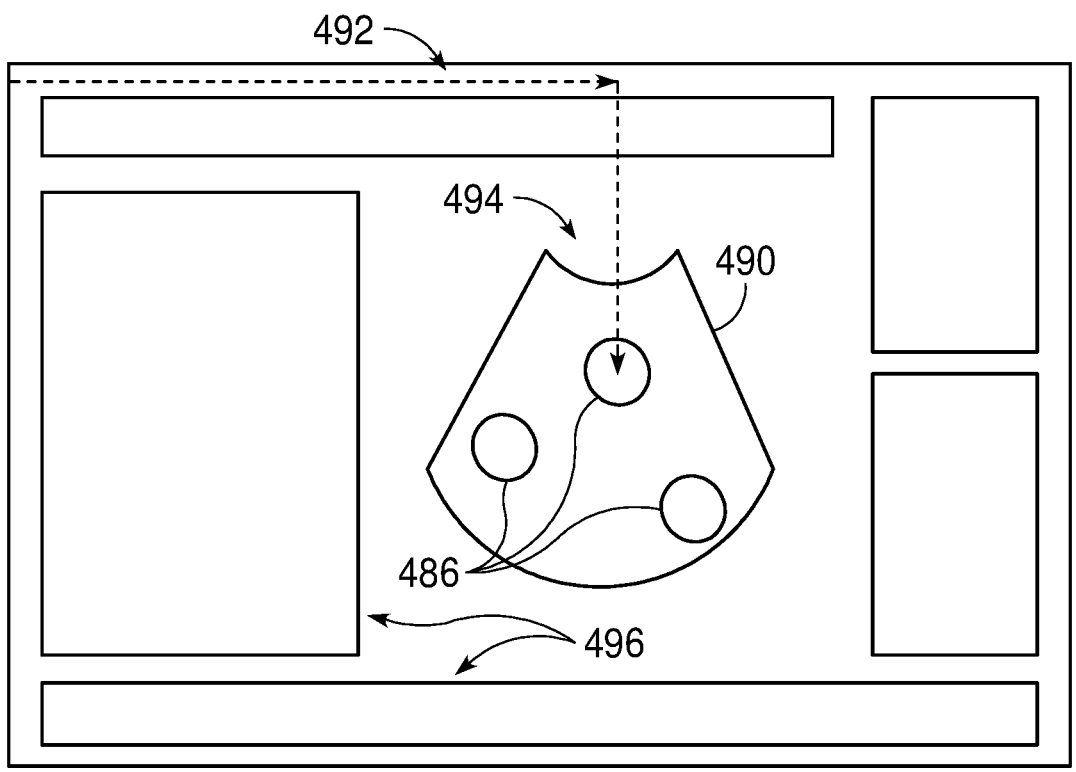

Referring now to FIGS. 4A-4C, an embodiment of calibration performed on IGRIS 100 is shown.

Referring to FIG. 4A, an embodiment of the calibration station. The calibration station may include a known calibration block 480. The known calibration block 480 may comprise a reference surface 482 for the Imaging Device 146 to use as a reference point, a material 484 (e.g., ultrasound gel, echogenic material, or material with the ability to reflect or transmit imaging waves in the context of surrounding regions), and one or more embedded known objects 486 (e.g., fiducial markers at known positions), and an enclosure surface 488.

In some embodiments, prior to the calibration, the user may configure the settings of the Imaging Device 146 as intended for use to perform a procedure. In some embodiments, the settings are automatically determined based on a priori information, including procedure type, prior calibration settings, or other information known to one of skill in the art to assist in calibration.

Referring to FIG. 4B, the user may place the Imaging Device 146 against the reference surface 482 and on material 484 to maintain rough positioning of the Imaging Device 146 once the settings are configured as desired. In some embodiments, the placement of Imaging Device 146 may only require a short amount of time (e.g., roughly one second or less). In some embodiments, reference surface 482 may be optionally replaced with a target indicator on material 484 indicating where the Imaging Device 146 should be positioned. The target indicator may appear as an X, a circular marking, a protrusion, an indent, or any other form which informs the user where the Imaging Device 146 should be positioned.

Once Imaging Device 146 is properly positioned, IGRIS may capture the real-time image 490, which may include capture of the one or more embedded known objects 486.

Referring to FIG. 4C, IGRIS may then perform an image registration function of the real-time image 490 and determine the horizontal offset 492 and vertical offset 494 coordinates (e.g., in pixels) for the one or more embedded known objects 486. In some embodiments, IGRIS may focus on real-time image 490 to perform its processing and ignore the user interface artifacts 496.

In some embodiments, one or more embedded known objects 486 may comprise any pattern or any image with distinguishable features. IGRIS 100 may fit a function known to the identified image/object pair data to determine the scale and offset, or any other sufficiently posed mathematical representation known to one of skill in the art, to map image pixels to physical locations under the probe.

In some embodiments, during the procedure IGRIS will analyze the ultrasound image 490 to enable robotic targeting including Basic Targeting and Intelligent Targeting. Further, in some embodiments, IGRIS will analyze the rest of the graphical user interface to detect changes that indicate that settings may have been adjusted and the system is out of calibration resulting in a safety fault.

IGRIS may also calculate a Calibration score which indicates the quality of the calibration. For example, a score of 90 on a scale of 100 may indicate a high quality calibration, a score of 70-89 may indicate an acceptable calibration, while a score of 0-69 may indicate the calibration may need to be performed again. The score may be based on the offset, scale, and/or scale transformation functions.

Factors that may affect the calibration score may include poor coupling of the Imaging Device 146 to the known calibration block 480, or uses an incorrect or damaged calibration block.

Basic Targeting

Using IGRIS, Basic Targeting allows a user to plan and execute an intervention (e.g., inserting an instrument, such as a needle, into a patient) in a more precise manner than conventional methods. In some embodiments, IGRIS 100 may perform an initial calibration step prior to use to ensure targeting accuracy.

For example, IGRIS may acquire real-time images of an object (e.g., a human anatomy) using an Imaging Device (e.g., ultrasound). IGRIS comprises a computer which receives the real-time images for display on a user interface of the computer. IGRIS comprises a robotic manipulator (e.g., robotic arm) coupled to the Imaging Device and an instrument guide. The robotic manipulator may be driven by motors and sensors (encoders), which may be used to control the pose (position and orientation) of the instrument guide, and thus the instrument relative to the Imaging Device. IGRIS tracks the instrument guide's pose relative to the Imaging Device. For example, IGRIS is capable of moving the instrument guide relative to the object that is being imaged, and can compute the location of the instrument guide relative to that image to facilitate targeting using data from Calibration and the robotic manipulator. For example, IGRIS tracks the pose of the instrument guide, the robotic manipulator, and Imaging Device by tracking (1) the position and orientation of the robotic manipulator relative to the Imaging Device and/or (2) the position and orientation of the instrument guide relative to the robotic manipulator to determine the desired trajectory of instrument guide relative to the Imaging Device.

IGRIS may augment the real-time images on the user interface with a first graphical overlay that represents the planned trajectory of the instrument relative to the image. The graphical overlays are updated in real-time based on any adjustments of the robotic manipulator and instrument guide. Conversely, the position and orientation of the robotic manipulator and/or instrument guide are also updated in real-time based on any adjustments of the graphic on the user interface.

Advantageously, the first graphical overlay and instrument guide may be used to guide an instrument (e.g., a needle) inserted into an object (e.g., human anatomy). For example, IGRIS may be used for medical procedures to determine insertion points and paths.

Basic Targeting supports multiple modes, including Backdrive and Tap to Target. Backdrive allows a user to adjust the pose (position and orientation) of the instrument guide and/or the robotic manipulator manually, and the updated pose is represented on the user interface in real-time. Tap to Target automatically adjusts the pose of the instrument guide and/or robotic manipulator by selecting, or "tapping," an area of interest on the user interface displaying the real-time images of the object using an input device (e.g., touch screen, mouse, keyboard, joy stick, track ball, etc.). Each shall be described in further detail below. In some embodiments, IGRIS 100 may optionally perform a Calibration step prior to use to ensure targeting accuracy.

Basic Targeting Flow

The following flow describes the set up for Basic Targeting, which allows for the execution of the aforementioned Backdrive and Tap-to-Target techniques. The flow for the Backdrive and Tap-to-Target techniques shall be described in further detail below.

Basic Targeting may operate according to the following steps and may be performed using IGRIS 100. In some embodiments, certain steps of this flow may be omitted. A health care practitioner ("HCP") may use IGRIS 100 to plan a medical procedure, such as an insertion or biopsy, which shall be used as an example to provide context.

Figure 5A:
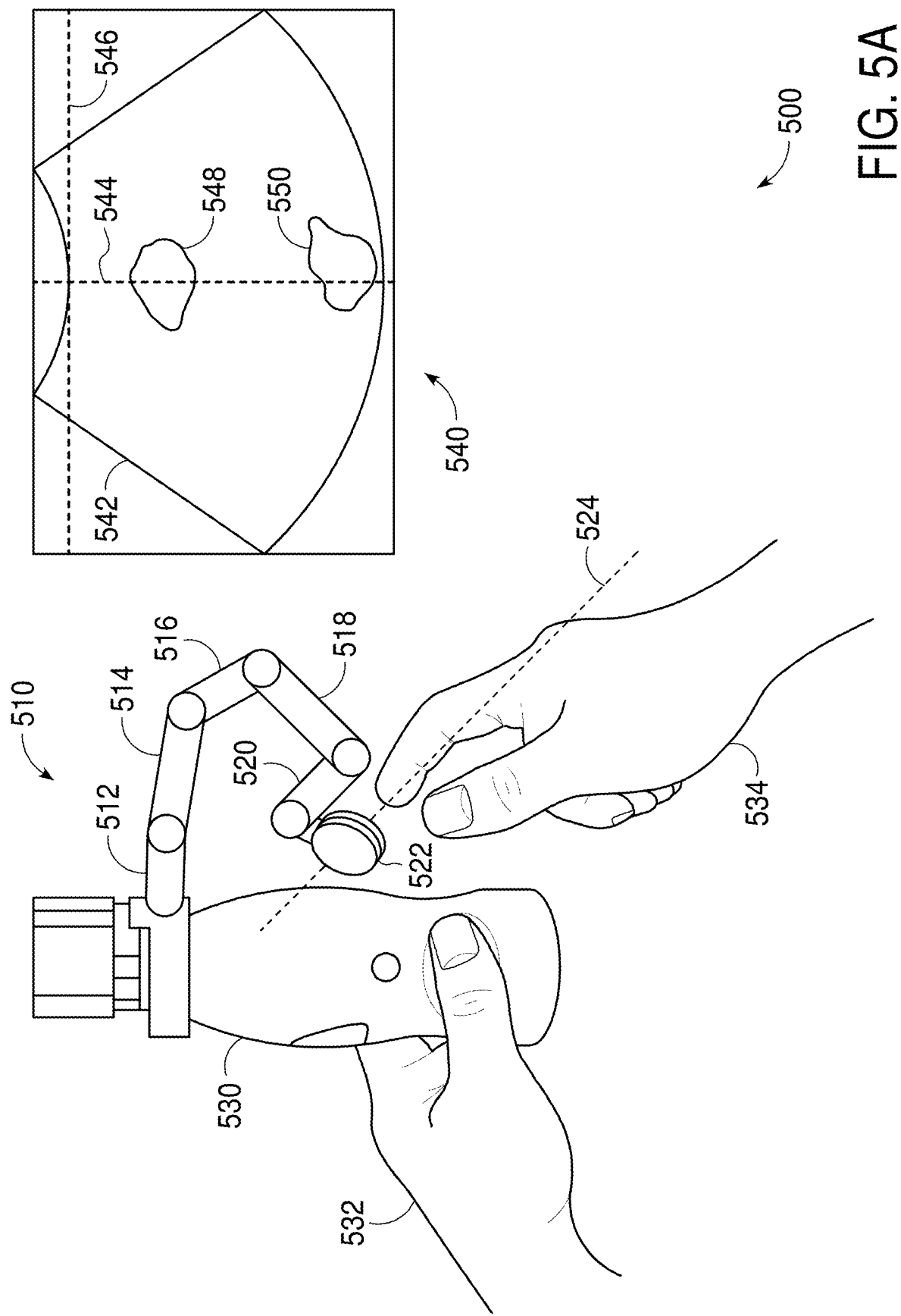

Referring now to FIG. 5A-5G, basic targeting as embodied herein illustrated. FIG. 5A illustrates a robotic arm 510 and image display 540. Robotic arm 510 includes links 512, 514, 516, 518, and 520, and instrument guide 522 having an alignment represented by needle trajectory 524. As an instrument is being inserted into instrument guide 522, it will follow along the instrument trajectory 524. In some embodiments, instrument guide 522 may come in various shapes, such as instrument guide discussed above. The HCP is holding an image device 530 in one hand 532 while preparing to manually move an instrument guide 522 with the other hand 534.

The anatomy scanned by image device 530 is presented in an image 540 presented on an image display; for the sake of discussion and illustration, the body of the patient being scanned below image device 530 has been intentionally omitted from FIGS. 5A-5G. The image includes the boundaries of the scan 542, a vertical axis 544, a horizontal axis 546, a first target of the anatomy 548, and a second target area 550 of the anatomy. Referring to FIG. 5A, a first graphical overlay of a desired target for final location of the instrument tip may be presented (represented by the intersection of the vertical axis 544 and the horizontal axis 546) on the ultrasound image 540 and is representative of a path aligned with the instrument trajectory 524 when the instrument is inserted into the patient through the instrument guide 522. A second graphical overlay representing the desired instrument path 552 is determined from the pixel calibration and the pose of instrument guide 522 as determined as a function of robot kinematics; as such, the desired instrument path 552 may be responsive to movement of instrument guide 522.

If the HCP wishes to identify an anatomical target and manually insert the instrument into the patient and steer the instrument to the target, the HCP may manually move instrument guide 522 until the desired instrument path 552 is seen as intersecting the target.

Figure 5B:
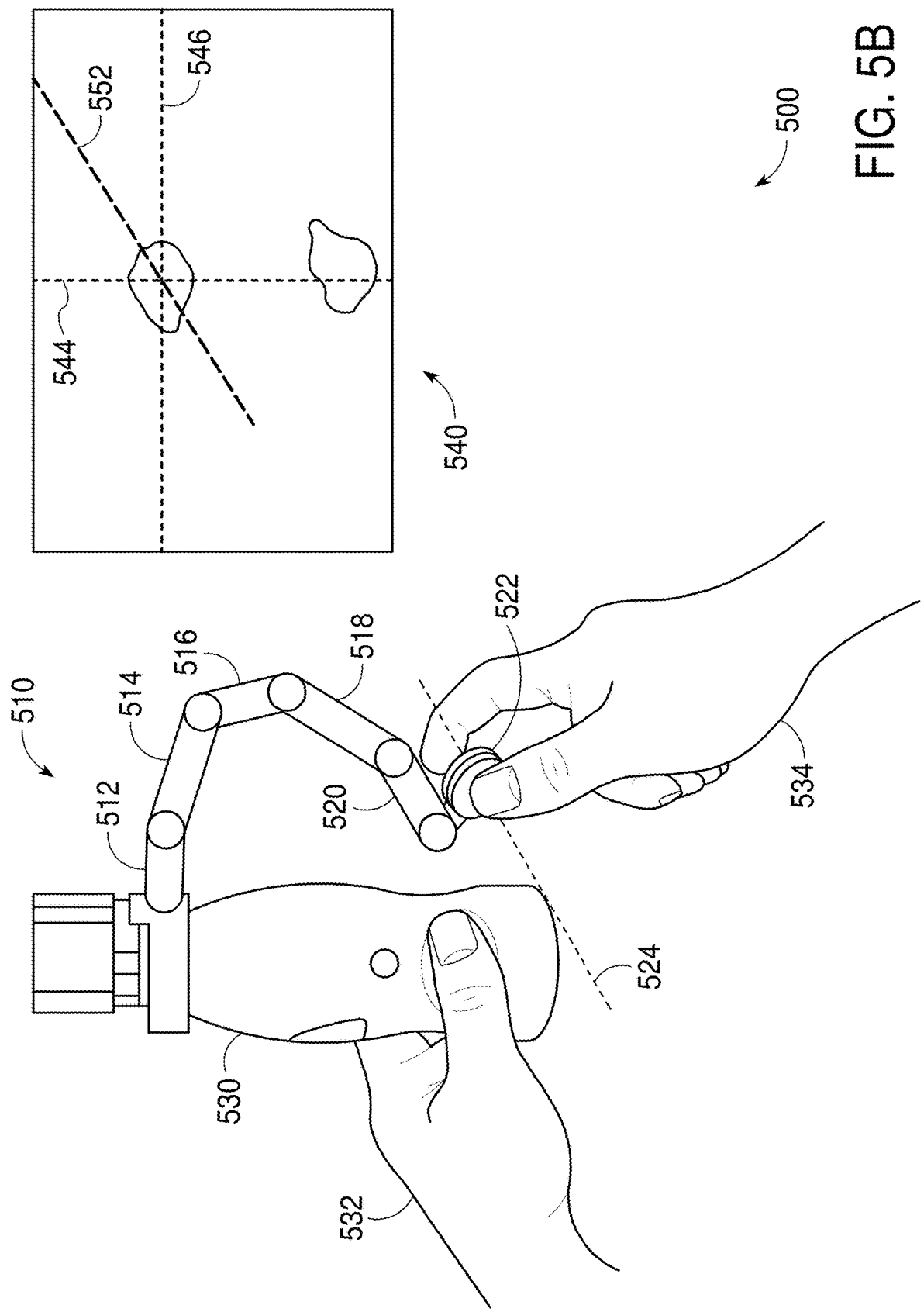

As shown in FIG. 5B and through a comparison with FIG. 5A, the HCP has physically changed the configuration of robotic arm 510 by moving instrument guide 522 downward as indicated by a change in the position of the instrument guide 522; this change has also resulted in changes to the positions of links 514, 516, 518, and 520. In response, the pixel locations of desired instrument path 552 have changed so that instrument trajectory 524 aligns itself with instrument guide 522 based upon the calibration and robotic kinematics.

As shown in FIG. 5C, the HCP may control the position of the instrument guide 522 by tapping on the desired instrument path 552 at the intersection of the vertical axis 544 and the horizontal axis 546.

As shown in FIG. 5D, the HCP has dragged the desired instrument path 552 to the second target 550. Although the second target happens to align with the vertical axis, the desired instrument path 552 may be dragged to intersect a target at any location in the image. In response and through a comparison with FIG. 5C, the configuration of robotic arm 510 as indicated by changes to the positions of instrument guide 522 and links 518 and 520. As a result of a corresponding change to the pixel locations of the desired instrument path 552, motor(s) (not shown) have driven robotic arm 510 into a new configuration. Based upon the calibration and robotic kinematics, signal(s) are generated in response to the change in pixel locations and provided to drive motor(s) so that instrument guide 522 is positioned to align itself with desired instrument path 552 to the second target 550.

As shown in FIG. 5E, after the user has touched the desired target on the screen (from FIG. 5D), a circle 556 appears representing the user's desired target for final location of the instrument tip. The configuration of robotic arm 510 has changed in response to the HCP changing planned instrument trajectory 552 by dragging it angularly upward from a location along the desired instrument path 552 other than from the second target 550. Once again, as a result of the change to the pixel locations of the desired instrument path 552, motor(s) have driven robotic arm 510 into a new configuration. Based upon the calibration and robotic kinematics, signal(s) are generated in response to the change in pixel locations and provided to drive motor(s) so that the instrument guide 522 is positioned to align itself with the desired instrument path 552.

Figure 5F:
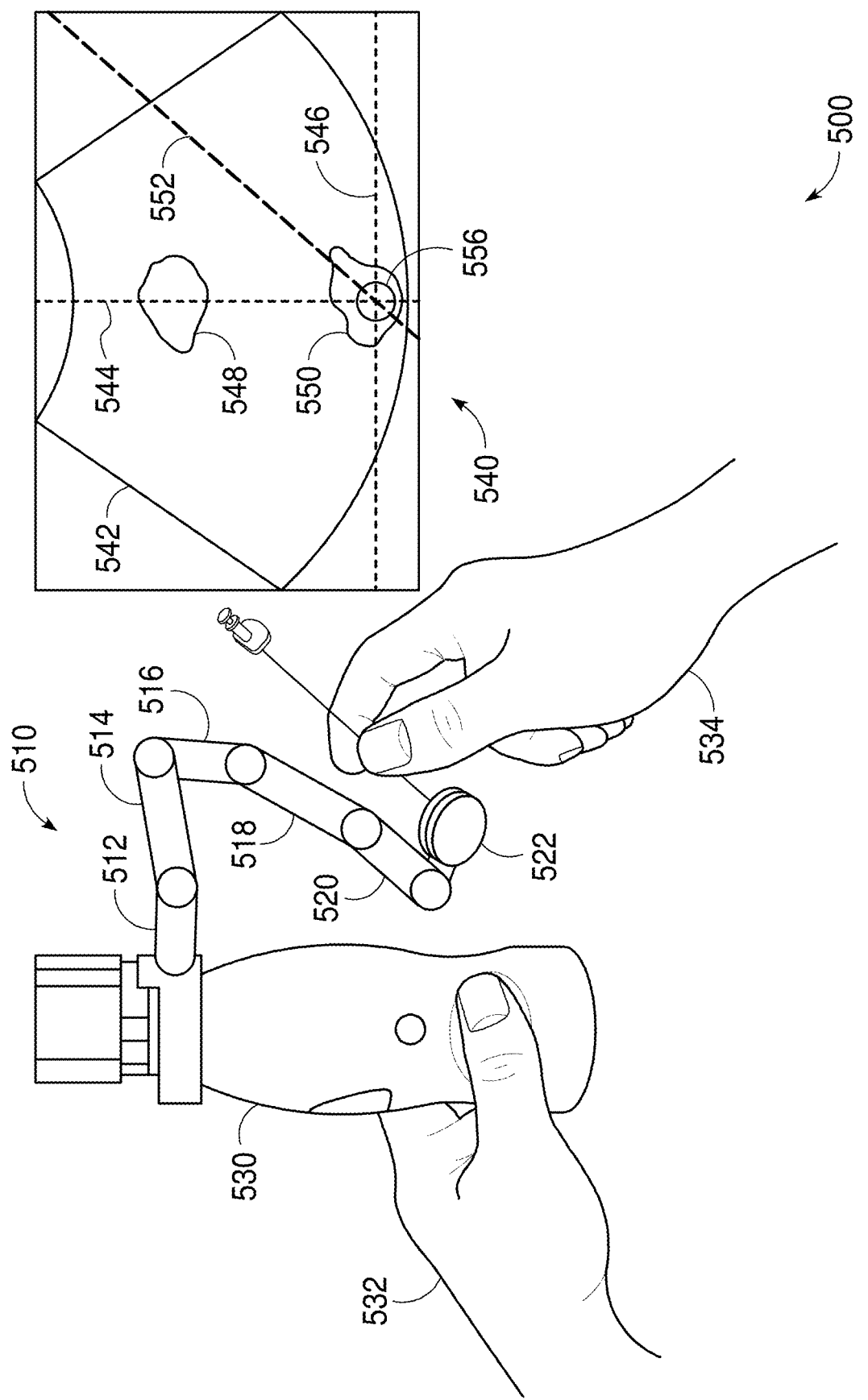

As shown in FIG. 5F, the HCP begins a process of manually inserting one end of an instrument into the instrument guide 522. Because the instrument guide 522 and the instrument trajectory are aligned with each other, the instrument will travel inside of the body along a path represented by desired instrument path 552.

As shown in FIG. 5G, the tip of the instrument is represented by a third graphical overlay (e.g., dot 558), and the instrument has reached the second target 550, which indicates the end of the manual insertion process of the instrument.

Figure 6A:
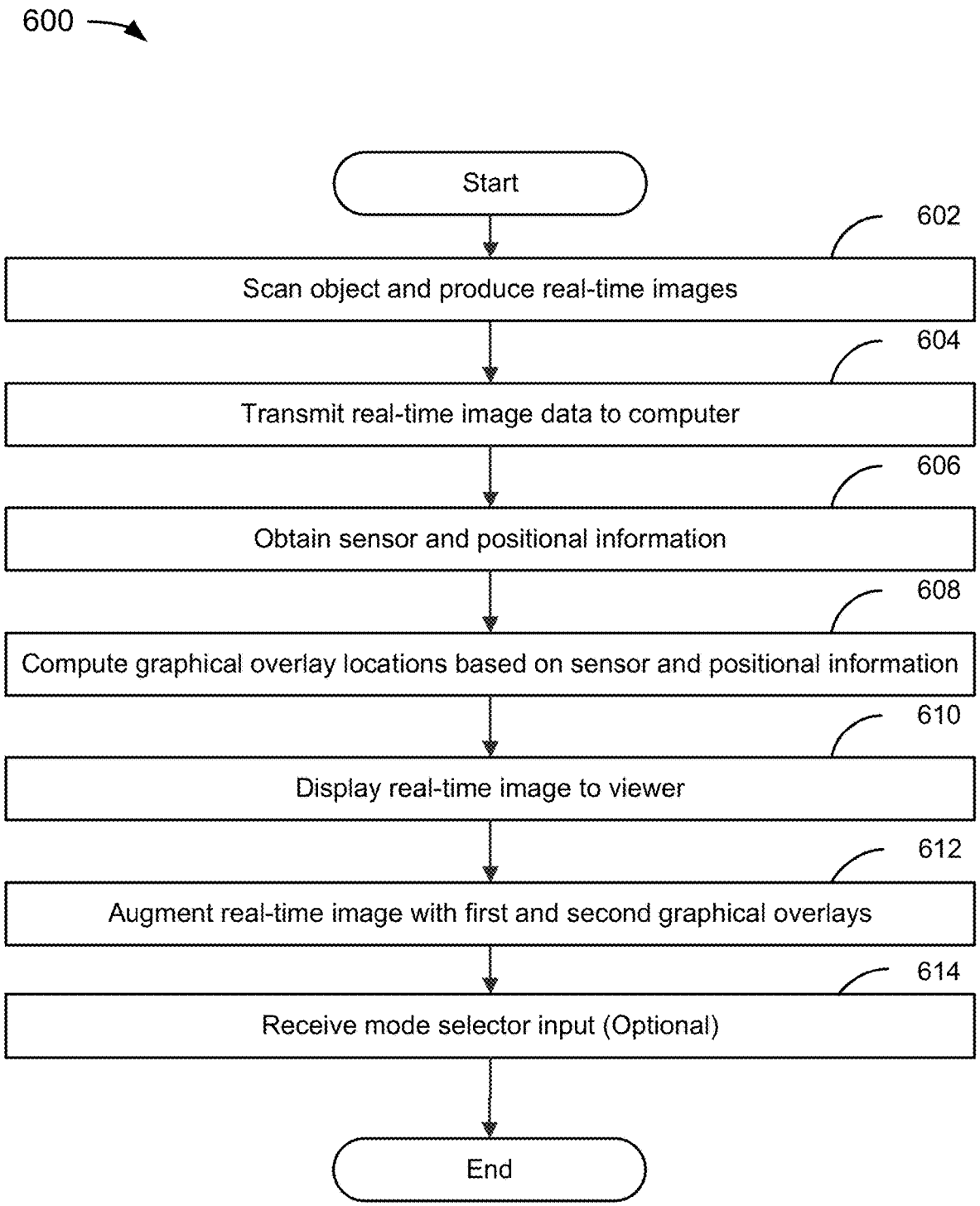
FIGS. 6A-6C, inclusive, illustrate an embodiment of the Basic Targeting flow, including Backdrive and Tap to Target.

FIG. 6A depicts flowchart 600 disclosing an example of a method for basic targeting, where the IGRIS 100 may be programmed or configured with instructions corresponding to the modules embodied in flowchart 600.

In step 602, IGRIS 100 comprises an Imaging Device 146 to scan an object and produce real-time images (e.g., ultrasound imaging) of the object (e.g., human anatomy of a patient). An example of an Imaging Device 146 includes an ultrasound transducer, commonly referred to as a probe. For example, HCP uses IGRIS 100 to scan a patient's anatomy and acquire real-time ultrasound images of the anatomy.

Imaging Device 146 also includes associated application specific data processing hardware to emit and receive ultrasonic signals, and process the raw data to extract useful information. In the example of an ultrasound transducer, the information may include M Mode, B Mode, Doppler and other imaging modalities. Further information may include different transducer architectures that allow the ultrasound signals to be steered to different regions of interest. There are many different ways to steer ultrasound including Linear Array, Curvilinear Array, Matrixed Array, Phased Array, Actuated or wobbled transducers, and Rotated transducers.

In step 604, the Imaging Device 146 transmits the real-time images to a computer coupled to the Imaging Device 146. The computer comprises drivers or video capture cards (e.g., Imaging Device Drivers 148) which receive the real-time images for processing.

In step 606, Encoders/IMU 118 may obtain or generate sensor and positional information from Instrument Guide 128 and Motors 122. Motors 122 may be coupled to Robotic manipulator 126, and thus positional information for Robotic manipulator 126 may be derived based on Encoders. Encoders/IMU 118 and Imaging Device 146 may communicate the sensor and positional information to the Drivers (e.g., Encoders/IMU Drivers 120 and Imaging Device Drivers 148, respectively).

In step 608, first and second graphical overlay locations (described in further detail in step 612) are computed based on the sensor and positional information from step 606 for display on the User Interface 132

In step 610, User Interface 132 may display the real-time images of the object for the user to view. In some embodiments, this may appear as a "live view" from Imaging Device 146. The real-time images are updated based on any change in position or orientation of the Imaging Device 146. In some embodiments, the User Interface 132 displays the real-time images along an X-Y axis plane.

The User Interface 132 denotes typical computer interfaces and displays for displaying images and video to the user. The user interface may take inputs from various sources and display visualizations. Inputs include data entry from the HCP for system configuration, including selection of the procedure to be performed or anatomy to be targeted, as well as tools for procedure planning and confirmatory steps. Visualizations include real time imaging of ultrasound that could be planar, multi planar, or volumetric depending on the US imaging hardware capabilities.

In step 612, IGRIS may additionally augment the real-time images on the User Interface 132 with a first graphical overlay that represents the desired target for final location of the instrument tip, and a second graphical overlay that represents the desired trajectory (or path) of the Instrument Guide 128 across or through the image. For example, the first graphical overlay provides the intended final destination for the instrument (e.g., needle), and the second graphical overlay provides an estimation of the path of an instrument (e.g., a needle) being inserted into the object (e.g., human anatomy) using the instrument guide. Visually, the first graphical overlay may appear as a dotted circle or may appear as another visualization that indicates the final target for the needle tip, while the second graphical overlay may appear as a colored solid or dotted line over the real-time images of the object, or may appear as another visualization that indicates the desired trajectory of an instrument inserted into the object using the Instrument Guide 128. The first graphical overlay may provide the user with guidance for the depth the needle will travel, while the second graphical overlay may provide the user with guidance of the path the needle will travel into the object during a needle insertion.

Advantageously, the first and second graphical overlays and instrument guide may be used to guide an instrument (e.g., a needle) inserted into an object (e.g., human anatomy). For example, IGRIS may be used for medical procedures to determine insertion points and paths.

In step 614, IGRIS may include a mode selector input to trigger either the Backdrive or Tap to Target modes. The mode selector input may appear on the user interface as a "button" or option, or may also be integrated as a hardware indicator (e.g., a button or toggle), or any other toggle or selection method known to one of skill in the art. In some embodiments, the mode selector input may be obviated by automating detection of the preferred mode. For example, mode selection may be automated by determining the last received input of IGRIS 100 and switching IGRIS to the appropriate mode (e.g., IGRIS may switch to Tap to Target mode if IGRIS detects input is received to the User Interface, and may switch to Backdrive mode if IGRIS detects robotic manipulator has been manually adjusted). In some embodiments, IGRIS may include an indicator (e.g., on the user interface, or a physical indicator such as an LED) of the mode status (e.g., current mode, a change in mode, conflicts, etc.). For example, in the case of a conflict in input (e.g., both manual adjustment of the robotic manipulator and input on the user interface is received at relatively the same time), IGRIS shall provide an indication that there is a conflict in input.

Basic Targeting Backdrive

Basic Targeting Backdrive allows a user to adjust the pose of the instrument guide and/or the robotic manipulator manually. For example, a user may manually position and/or orient the robotic manipulator and/or the instrument guide to prepare for a medical procedure, such as inserting a needle into a specific region of the human body. In response to the adjustment of the pose(s), IGRIS updates the graphical overlays in real-time to provide the user a guide for the desired trajectory (or path) of an instrument (e.g., needle) being inserted using the instrument guide. Once the instrument is inserted into the object, IGRIS may augment the real-time images on the user interface with a second graphical overlay that represents the depth of the instrument inserted into the object. The second graphical overlay may be calculated based on measurements of depth, velocity, etc. of an instrument inserted using the Instrument Guide 128. Conveniently, the first graphical overlay (e.g., the desired trajectory of the instrument inserted into the instrument guide) and the second graphical overlay (e.g., the actual instrument inserted into the object using the instrument guide) should be similarly oriented, if not identical.

In some embodiments the robotic manipulator may be constrained to be backdriven in restricted degrees of freedom. Free backdriving allows for arbitrary motion of the robotic manipulator and instrument guide in six degrees of freedom. During constrained backdriving, the instrument guide may be constrained to always point at a target location defined in a previous basic targeting step, and denoted by the first graphical overlay. In this manner, the user may position the location of the instrument guide to define the insertion location and distance from the patient skin, while maintaining accurate targeting of the desired image location. This constrained motion may be calculated by the haptic rendering 138. Other embodiments may constrain the insertion location allowing for the adjustment of the target location.

Basic Targeting Backdrive Flow

Figure 6B:
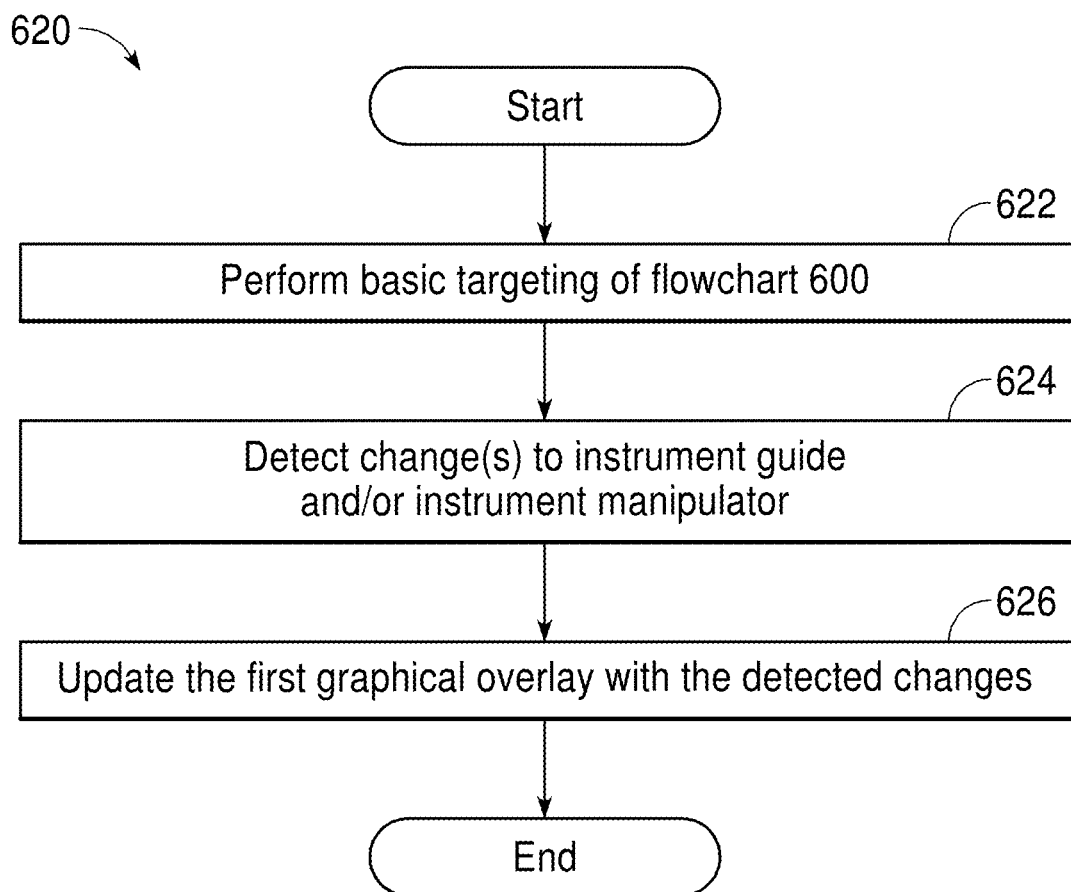

FIG. 6B depicts flowchart 620 disclosing an example of a method for Basic Targeting Backdrive flow, where the IGRIS 100 may be programmed or configured with instructions corresponding to the modules embodied in flowchart 620. In some embodiments, certain steps of this flow may be omitted.

In step 622, IGRIS 100 performs the Basic Targeting flow described in module 600.

In step 624, IGRIS 100 may detect that the position or orientation of Instrument Guide 128 or Robotic manipulator 126 has been changed. For example, a user may decide to manually adjust the Instrument Guide 128 or Manipulator 126. In response, IGRIS 100 may process the updated position information on the User Interface 132 to reflect the changes according to steps 606-612 of the Basic Targeting flow.

In step 626, the graphical overlays described herein are updated in real-time based on any adjustment of the relative pose of the Imaging Device 146, the Robotic manipulator 126, and the Instrument Guide 128. The graphical overlays may utilize different colors, shapes, or thicknesses to distinguish each overlay.

Basic Targeting Tap to Target

Basic Targeting Tap to Target allows a user to automatically adjust the pose of the instrument guide and/or robotic arm using an input device (e.g., touch screen, mouse, keyboard, joy stick, track ball, etc.) coupled to the computer to select, or "tap," an area of interest on the user interface displaying the real-time images of the object. In response, the instrument guide and/or robotic arm are automatically re-positioned such that the instrument guide path is directed to the "tapped" area of interest. For example, the display may be coupled to a touch screen on the user interface where a user may "touch" the pixel on the screen denoting the desired location to place a needle tip. In response, the pose of the instrument guide and/or robotic arm, and the graphical overlays, are automatically adjusted to reflect the desired positioning.

Basic Targeting Tap to Target also allows a user to adjust the first graphical overlay (e.g., the desired trajectory of the instrument guide) using the input device to "move," or adjust the approach angle, of the second graphical overlay to a desired pose. For example, a user may use a touch screen or mouse to move or drag the second graphical overlay to an area safe for needle insertion. In response, the orientation of the instrument guide and/or robotic arm, and the graphical overlays, are automatically adjusted to reflect the desired positioning. The second graphical overlay may be adjusted in different manners, such as directionally (e.g., up, down, left, right) or rotationally (e.g., clockwise, counter-clockwise).

Basic Targeting Tap to Target Flow

Figure 6C:
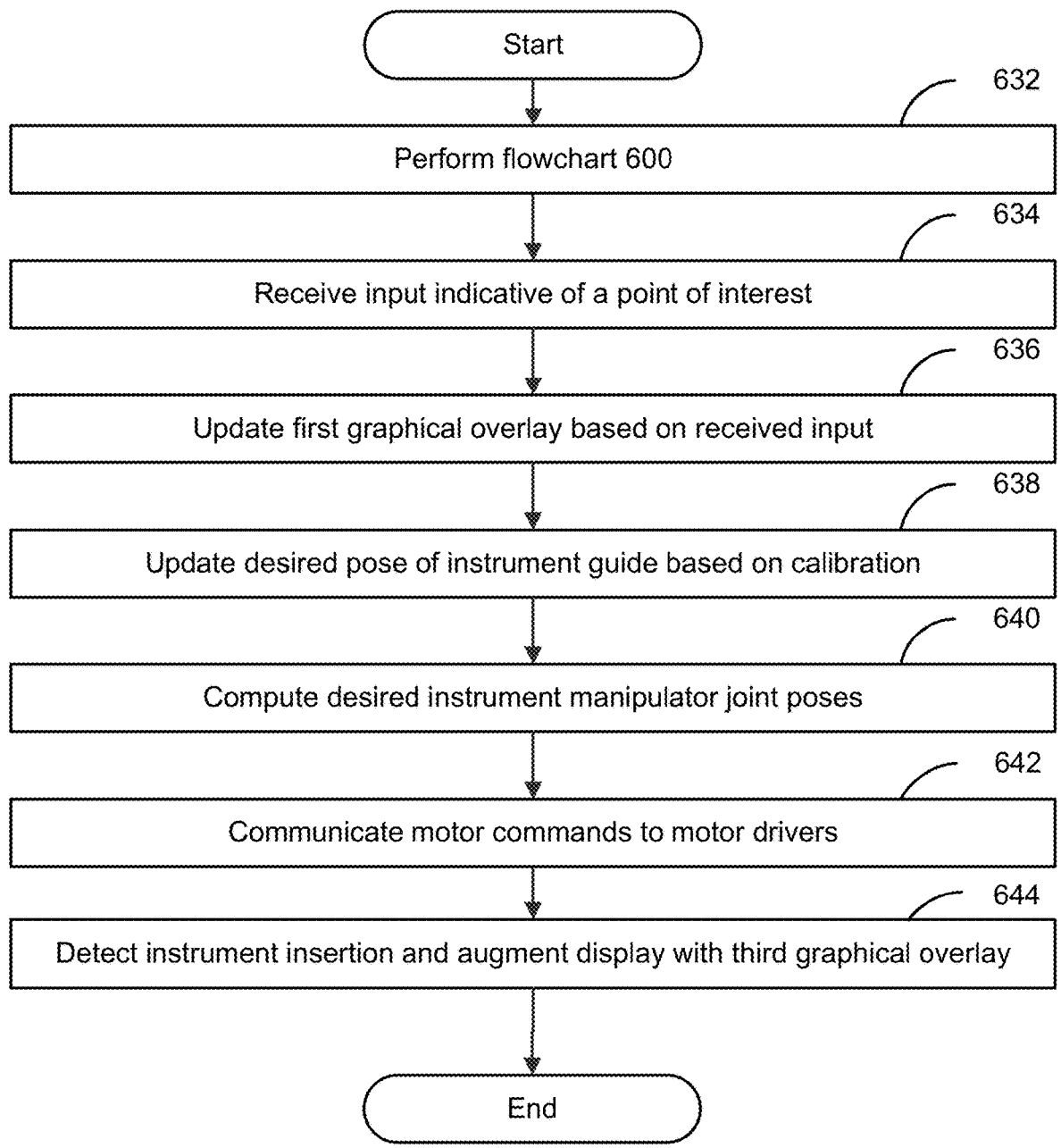

FIG. 6C depicts flowchart 630 disclosing an example of a method for tap-to-target, where the IGRIS 100 may be programmed or configured with instructions corresponding to the modules embodied in flowchart 630. In some embodiments, certain steps of this flow may be omitted.

In step 632, IGRIS 100 performs the Basic Targeting flow described in module 600.

In step 634, IGRIS 100 may receive an input indicating a point of interest from Display Unit 116, where the input may be a touch. For example, a user may select, or tap, a particular pixel of the real-time images of the object screen representing the desired target point for a needle. In an alternative embodiment, step 634 may receive an input indicating a desired movement of the first graphical overlay and the second graphical overlay. For example, a user may adjust the position or orientation of the Instrument Guide 128 by moving or dragging the pose of the second graphical overlay. The second graphical overlay may be adjusted in different manners, such as directionally (e.g., up, down, left, right) or rotationally (e.g., clockwise, counter-clockwise). The first graphical overlay may be adjusted as well, for example, by selecting, or tapping, an area of the screen. In some embodiments, alternative input devices to the Display Unit 116 may be utilized (e.g., mouse, keyboard, joy stick, track ball, etc.) to receive the input.

In step 636, User Interface 132 may update the position of the first graphical overlay and second graphical overlay based on the received input. For example, User Interface 132 may adjust the position of the first graphical overlay to point to the desired target point for the needle and adjust the pose of the second graphical overlay to the desired trajectory for the needle inserted via the instrument guide.

The calculation to determine the new pixel location may be performed a number of ways, including the pixel location of the previous position of the first graphical overlay relative to the new pixel location, the absolute pixel location along the X-Y axis plane, the pixel location along the X-Y axis plane relative to the Imaging Device 146, or any calculation that may be understood by one of ordinary skill in the art.

In step 638, Trajectory Planner 136 may calculate an updated desired trajectory for the Robotic manipulator 126 and Instrument Guide 128 based on the received input. In other words, IGRIS 100 will calculate an updated pose and move the Robotic manipulator 126 and Instrument Guide 128 based on the received input from step 634.

In step 640, Closed Loop Control 144 receives the updated pose calculations and related information from Trajectory Planner 136 to compute the motor commands to move Motors 122, Robotic manipulator 126, and Instrument Guide 128 to the desired pose.

In some embodiments, Closed Loop Control 144 uses the outputs of the Trajectory Planner 136, and compares those to an estimate of the state of the Instrument Guide 128 and Kinematics 142 to compute motor commands.

In step 642, Closed Loop Control 144 communicates the computed motor commands to Motors Drivers 124 based on joint commands from the trajectory planner 136. In some embodiments, Motor Drivers 124 converts the computed motor commands into current to adjust the torque applied by the motors.

In step 644, IGRIS 100 may detect that an instrument (e.g., needle) has been inserted into the object via Instrument Guide 128 and in response, User Interface 132 may augment the real-time images on the user interface with a third graphical overlay that represents the depth of the instrument inserted into the object. Conveniently, the second graphical overlay (e.g., the desired trajectory of the instrument inserted into the instrument guide) and the third graphical overlay (e.g., the actual instrument inserted into the object using the instrument guide) should be similarly oriented, if not identical. In some embodiments, IGRIS 100 may determine the instrument depth by measuring the instrument movement through Instrument Guide 128. In other embodiments, IGRIS 100 may determine the instrument depth by performing an image analysis on the real-time images to detect the instrument in the image. In other embodiments, IGRIS 100 may utilize multiple instrument depth determinations, including those disclosed herein, or as understood by one of skill in the art.

Intelligent Targeting

Using IGRIS, Intelligent Targeting allows a user to plan and execute an intervention using 3D reconstructions of anatomy generated from 2D real-time images and using enhanced localization techniques to target specific areas of the anatomy. This may assist an HCP visually and offload the cognitive burden of attempting to interpret and identify target areas in the real-time images. For example, an HCP, who may be unsuccessful in locating a specific target location in the anatomy for a needle insertion using real-time ultrasound, may instead use Intelligent Targeting to generate a 3D reconstruction of the anatomy based on the real-time ultrasound images to more easily identify the target location. The HCP may also use enhanced localization techniques to track and lock on to the target location to prepare for the needle insertion. In some embodiments, IGRIS 100 may perform an initial calibration step prior to use to ensure targeting accuracy.

Intelligent Targeting includes two main features to facilitate such interventions: 3D Reconstruction and Localization.

3D Reconstruction refers to the creation of volumetric information based on a plurality of 2D real-time images (e.g., ultrasound) of an object (e.g., anatomical region of a body) and rendering the reconstruction to present a human interpretable view of the anatomy for procedural planning, as well as assisting in automatically planning the procedure. This includes the anatomy of interest as well as surrounding anatomy for detailed trajectory planning.

Localization refers to computing the pose of a real-time image (e.g., ultrasound), and as a result IGRIS, with respect to the target object and the volumetric imaging data of the scanned anatomy. Localization provides the ability to infer the location of target and surrounding anatomy in space relative to IGRIS as well as any trajectory planning primitives defined as a result of analyzing or interpreting the volumetric data, whether it be by a human or computer.

In some embodiments, Basic Targeting may be performed using 3D Reconstruction and Localization techniques to assist in locating a target.

For example, IGRIS may acquire a plurality of real-time images of an object (e.g., a human anatomy) using an Imaging Device (e.g., ultrasound). IGRIS may also include sensors to generate metadata for each of the real-time images, including information related to IGRIS when each image was captured (e.g., the pose of the components of IGRIS, the location of IGRIS relative to the object, timestamp information, the orientation of IGRIS, the velocity and direction of IGRIS, etc.). IGRIS comprises a computer which receives the plurality of real-time images and the associated metadata. IGRIS performs a correlation of the real-time images and metadata to generate a 3D Reconstruction of the object. In some embodiments, IGRIS may perform a non-linear optimization of the real-time images (without the metadata), based on consistency or correlation to generate a 3D Reconstruction of the object.

IGRIS includes an interactive user interface for display of the 3D Reconstruction in multiple view angles (e.g., coronal view (frontal), sagittal (lateral), and transverse (axial)). IGRIS may augment the 3D Reconstruction on the user interface with a first graphical overlay that represents the pose of the Imaging Device relative to the object by way of localization information. Additionally, IGRIS may augment the 3D Reconstruction on the user interface with a second graphical overlay that represents the desired (or planned) trajectory of the instrument relative to the anatomy. The graphical overlays are updated in real-time based on any adjustments of the Imaging Device, the robotic manipulator, and the instrument guide. This may allow a user to more easily locate and select the specific target area.

IGRIS may then provide an indicator on the user interface of the position and orientation of IGRIS relative to the specific target area. IGRIS comprises a robotic manipulator (e.g., robotic arm) coupled to the Imaging Device (e.g., ultrasound) and an instrument guide. IGRIS may be "locked" to the specific target area to prepare for the needle insertion, and the robotic manipulator will keep the instrument guide "locked on," or targeted, to the specific target area even if IGRIS is not still.

Referring now to FIGS. 7A-7K, inclusive, localization and targeting methods or techniques that may be performed by IGRIS 100 are illustrated. For the purpose of illustration, localization is demonstrated in FIGS. 7A-7F, inclusive, followed by targeting in FIGS. 7G-7K, inclusive. It will be assumed that a 3D Reconstruction has been created, views rendered, and the views are presented to the HCP in three 2D images presented on the right-side of FIGS. 7A-7K, inclusive: an image 702 is a top view of a 3D model presented with a horizontal reference 702h and a vertical reference 702v, an image 704 is a side view presented with a horizontal reference 704h and a vertical reference 704v, and an image 706 is a front view presented with a horizontal reference 706h and a vertical reference 706v. The reference lines in each view, represent the slice being displayed in the other two panes. In some embodiments, the intersection of these reference lines denote a target object or anatomy.

As the scan of FIGS. 7B-7F was performed, it will be assumed for the sake of illustration that the HCP has discovered a target of interest, and that the target of interest is located at the intersections of the horizontal axes 702h, 704h, and 706h and the vertical axes 702v, 704v, and 706v, respectively.

Figure 7A:
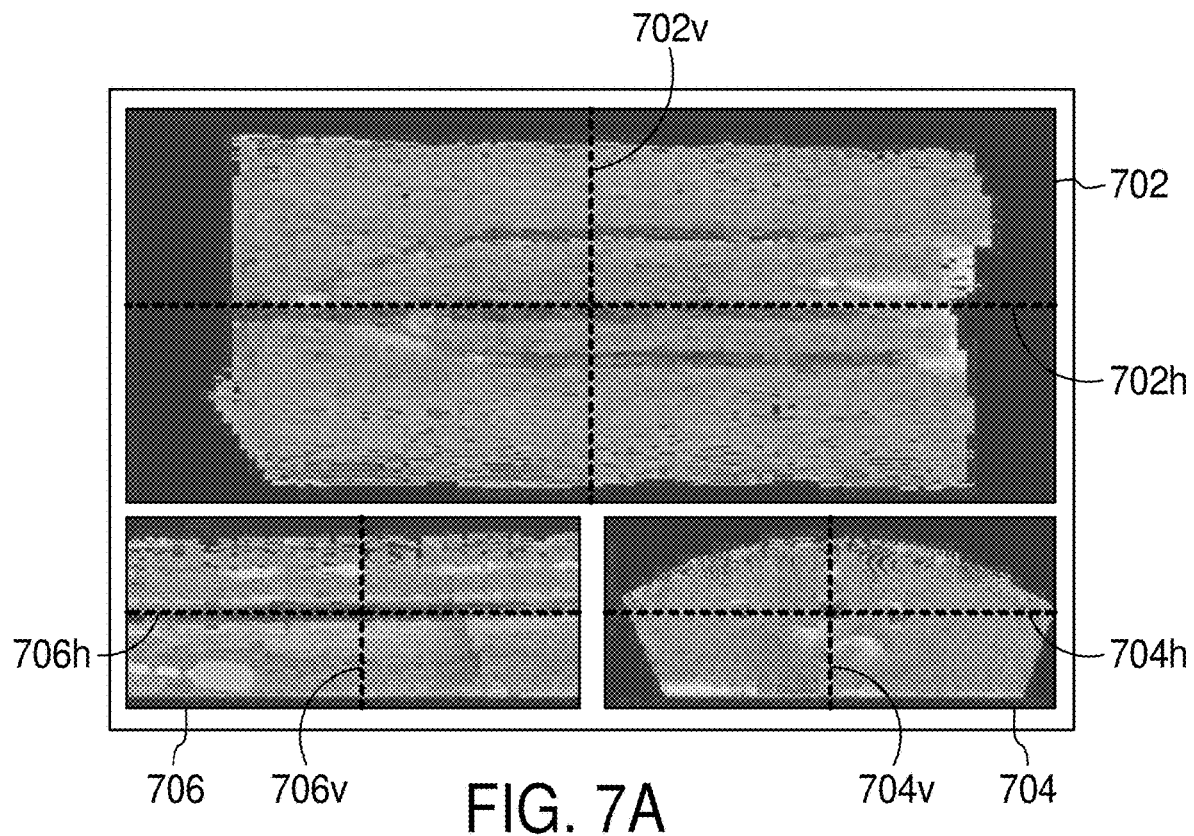
FIGS. 7A-7K, inclusive, illustrate an embodiment of Intelligent Targeting.
Figure 7B:
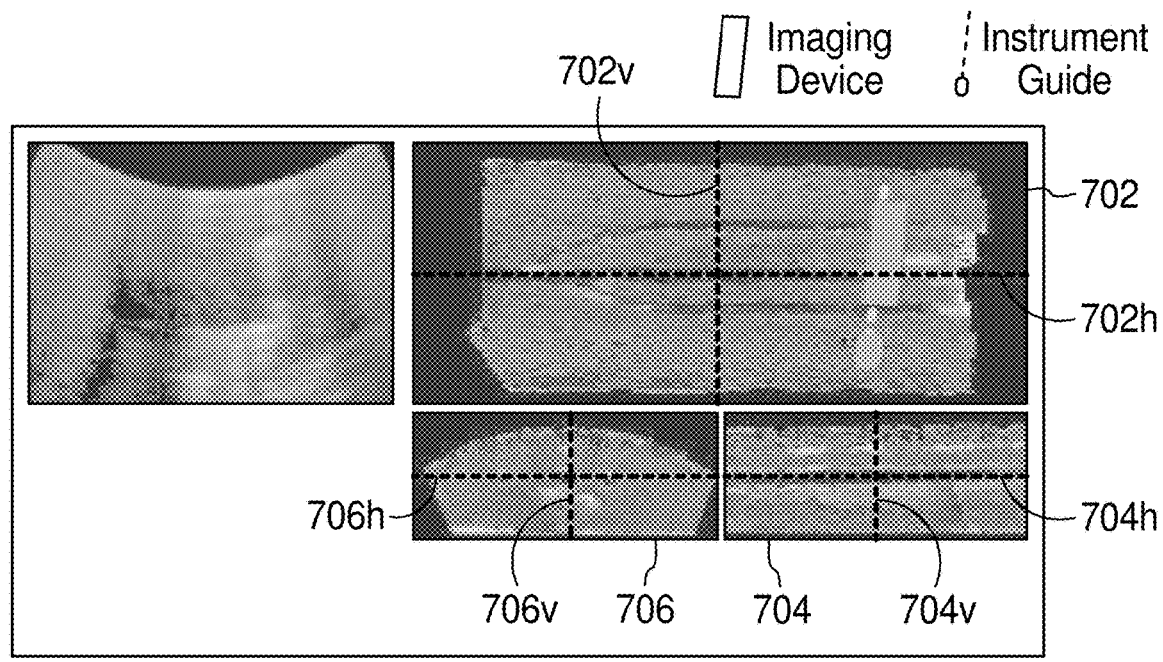
Figure 7C:
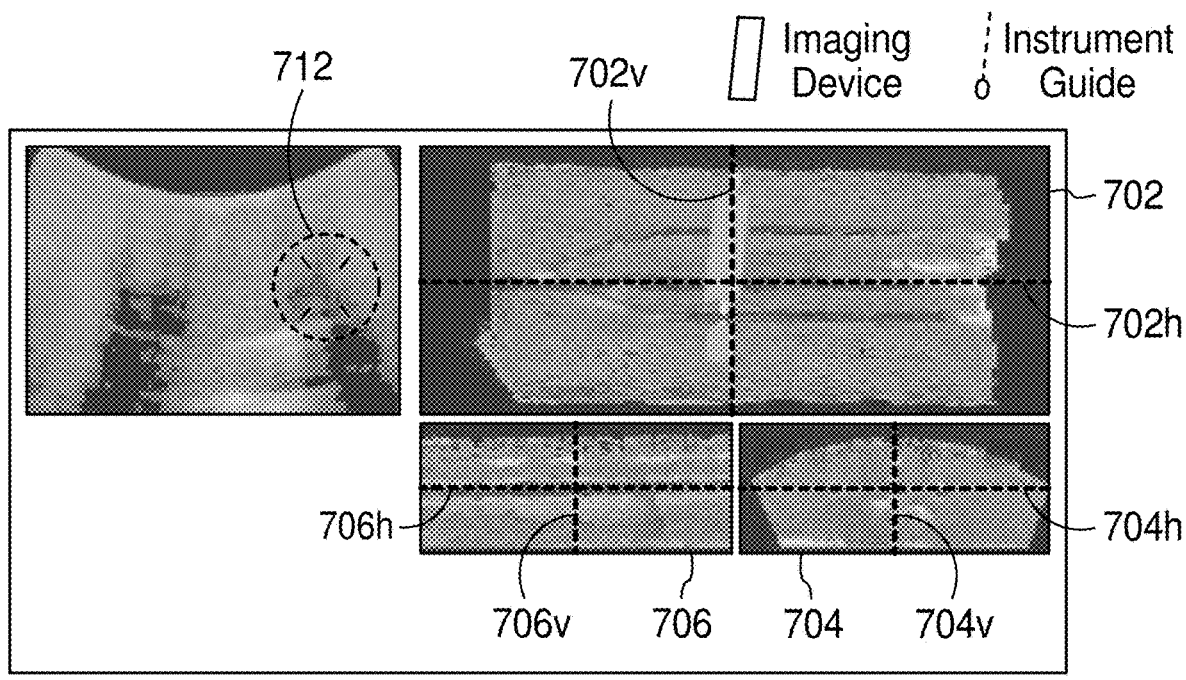
Figure 7D:
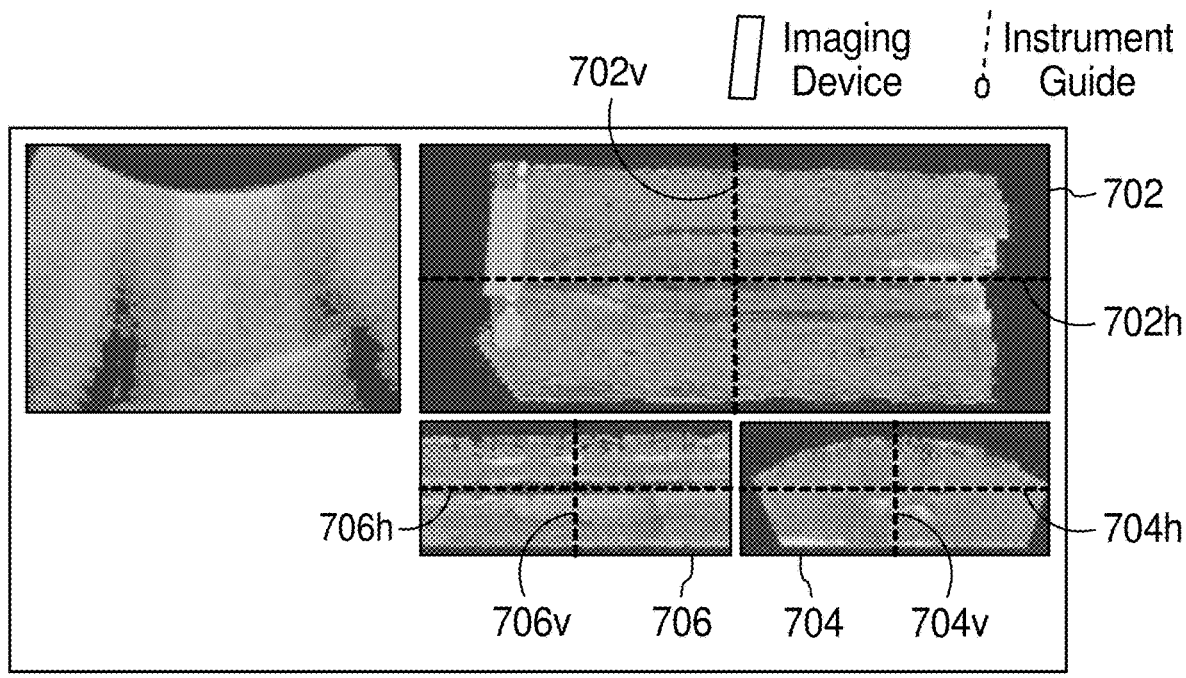

As shown in FIGS. 7B-7D, a right-to-left scan is being performed by the HCP using an imaging device indicated by the right-to-left movement of a first graphical overlay of an imaging device symbol and an instrument guide symbol. As embodied herein, one or more sources may be employed to localize the imaging device and the instrument guide within the room space from which the imaging device; for the purpose of illustration, the instrument guide is coupled to a robotic manipulator which, in turn, is coupled to the imaging device. As the imaging device changes its location during it travel, the sensors have been configured to capture its location from which IGRIS is programmed to receive location input from the source, determine its location relative to model, and generate a first graphical overlay of an imaging device and instrument guide symbols. In some embodiments, this may also be performed using various techniques described below in the "3D Reconstruction and Localization" sections.

In addition, an image of a scan being captured by the imaging device at that instance of time is presented. By presenting the imaging device and instrument guide symbols along with the scan, the HCP is informed of the location of the body corresponding to the scanned image.

As shown in FIG. 7C, the location of the imaging device symbol and the instrument guide symbol has just crossed over the intersections of the horizontal axes 702h, 704h, and 706h and the vertical axes 702v, 704v, and 706v. As observed in the scanned image, a graphical overlay 712 representative of the intersection is presented in the scanned image to convey this information; as noted, the graphical overlay 712 is presented to the right of the center of the image because the probe and needle guide have just crossed the intersections in its right-to-left travel.

Alternatively, when the imaging device is away from the target region, graphical overlay 712 may provide an indication of the target for the imaging device to move towards. This may be done by adjusting the size, color and or shape of the graphic to denote direction and distance to the object. These graphics may be used to help the user navigate to the target object. For example, the size and color of graphical overlay 712 may get larger and turn greener if the imaging device is getting closer, or may appear smaller and turn red if the imaging device is moving further away from the target. Once the imaging device has reached its target, graphical overlay 712 may turn into a solid green circle to indicate the imaging device is on target. In some embodiments, the user may navigate to the target object using these intelligent graphics, and then proceed with the intervention using Basic Targeting.

Figure 7E:
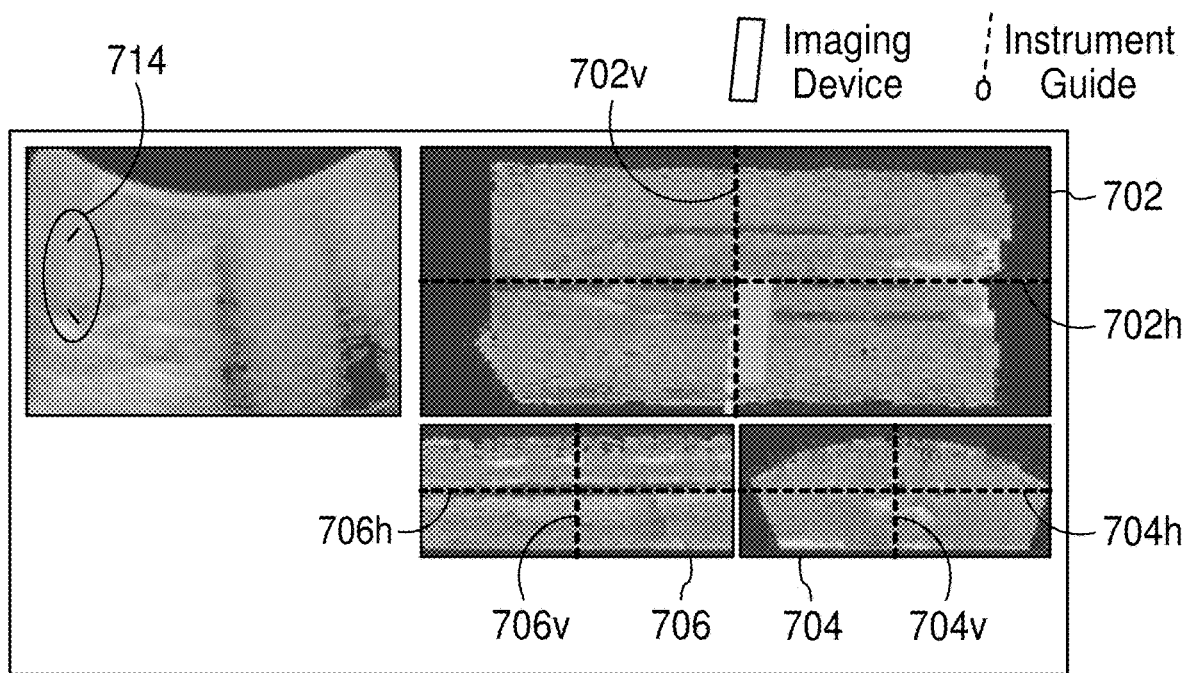
Figure 7F:
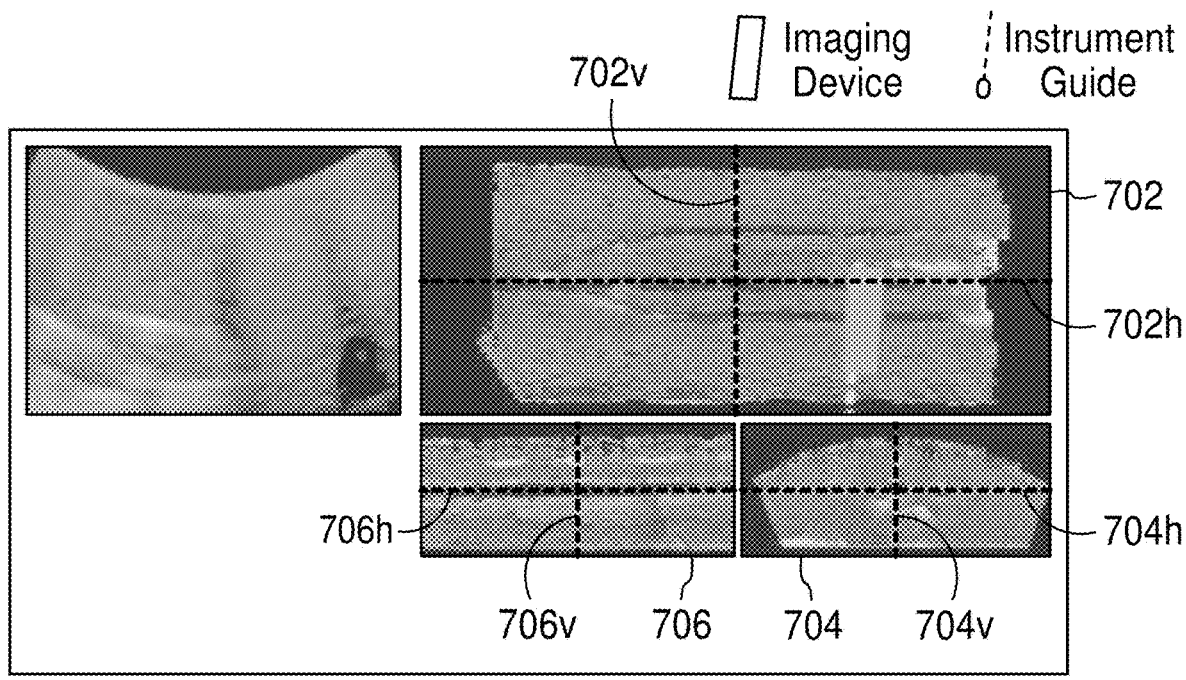

As shown in FIGS. 7E-7F, the HCP has reversed direction and is now performing a left-to-right scan as indicated by the movement of the imaging device symbol 708 and the instrument guide symbol 710. Referring to FIG. 7E, a symbol 714 is presented to the left of the center of the image briefly during the travel of the imaging device to convey to the HCP that the imaging device and the instrument guide is positioned just to the right of the target.

Figure 7G:
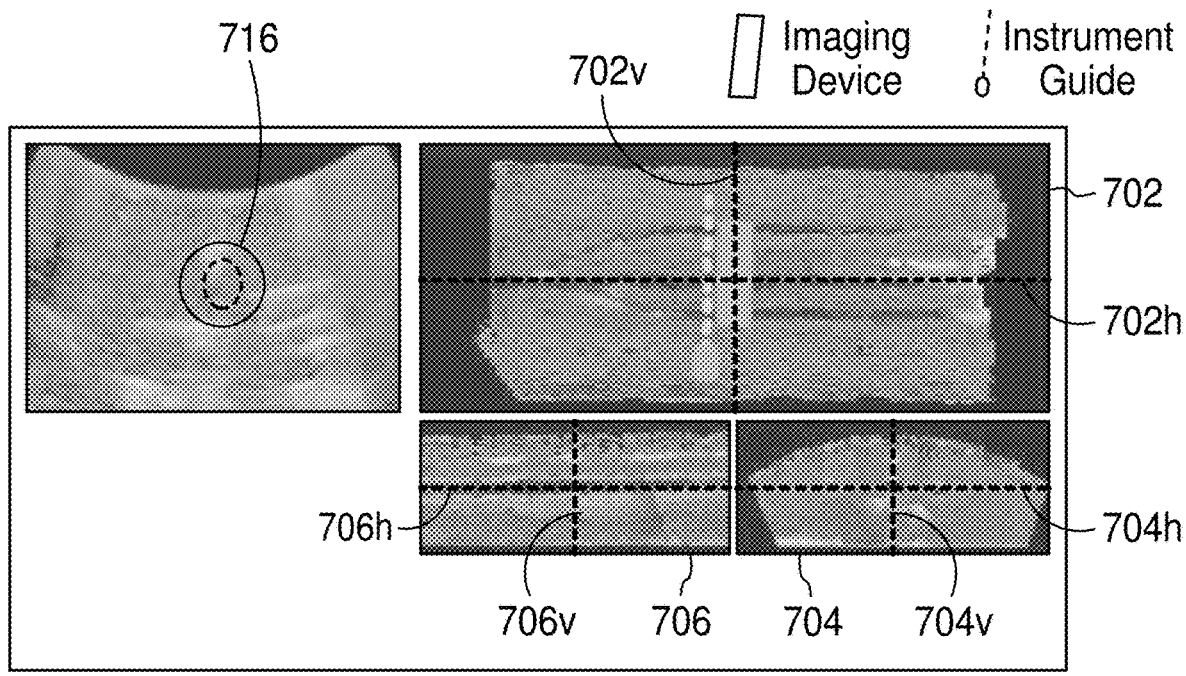

As shown in FIG. 7G, the targeting phase begins with the HCP moving the imaging device to the target as indicated by imaging device symbol 708 being located over intersection horizontal axis 702h and vertical axis 702v. As observed, the symbol 716 representative of the target has come into view; for the sake of illustration, the symbol 716 is used to indicate that the imaging device is positioned over the target.

As shown in FIGS. 7H-7K, now that the imaging device is properly aligned with the target, the HCP may prepare to orient the pose of the robotic manipulator and instrument guide to prepare for instrument insertion.

Figure 7H:
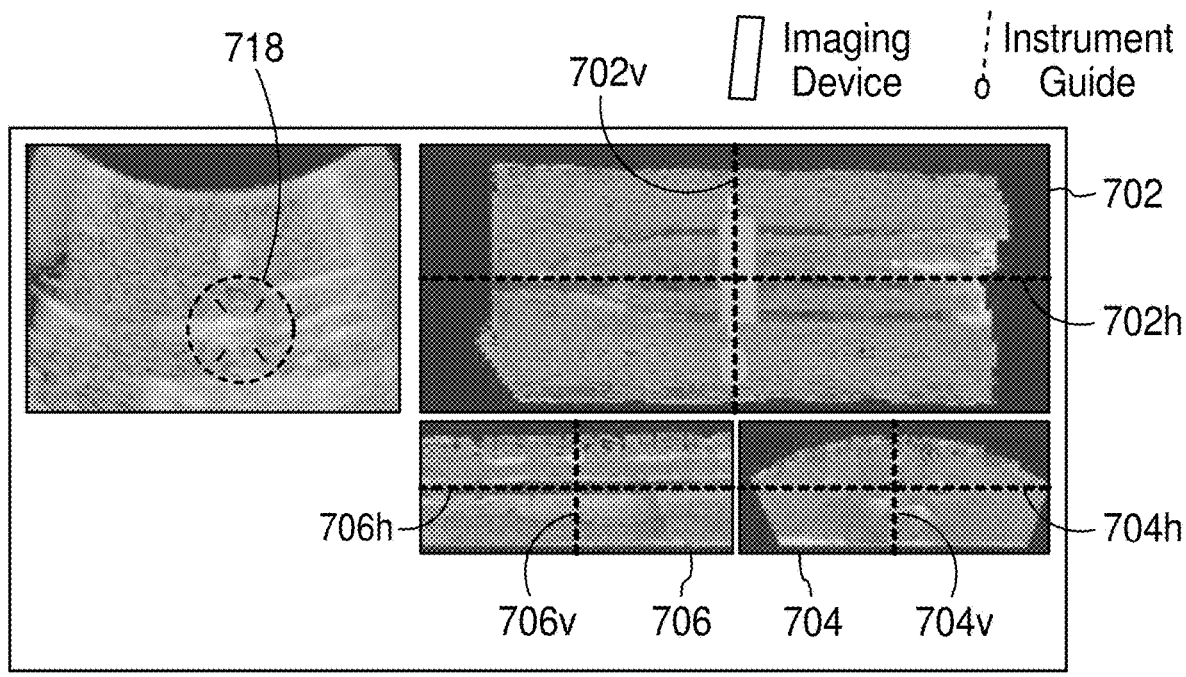

As shown in FIG. 7H, both the position of the imaging device symbol 708 and the instrument guide symbol 710 are centered over the target.

Figure 7I:
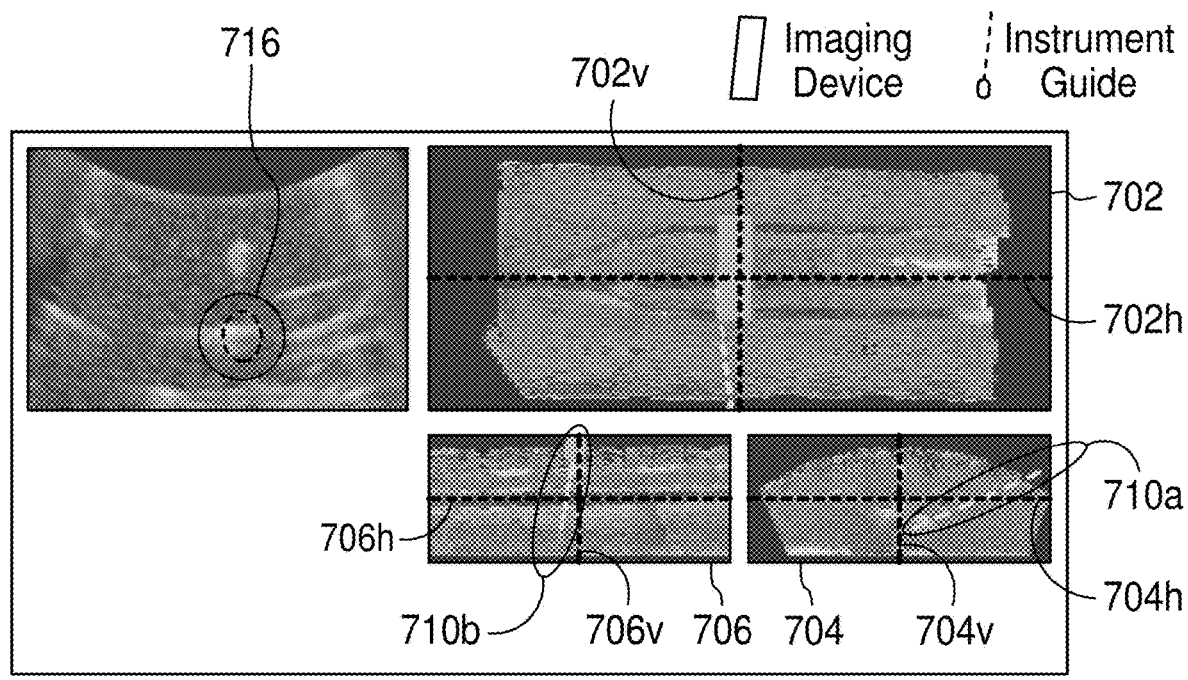
Figure 7J:
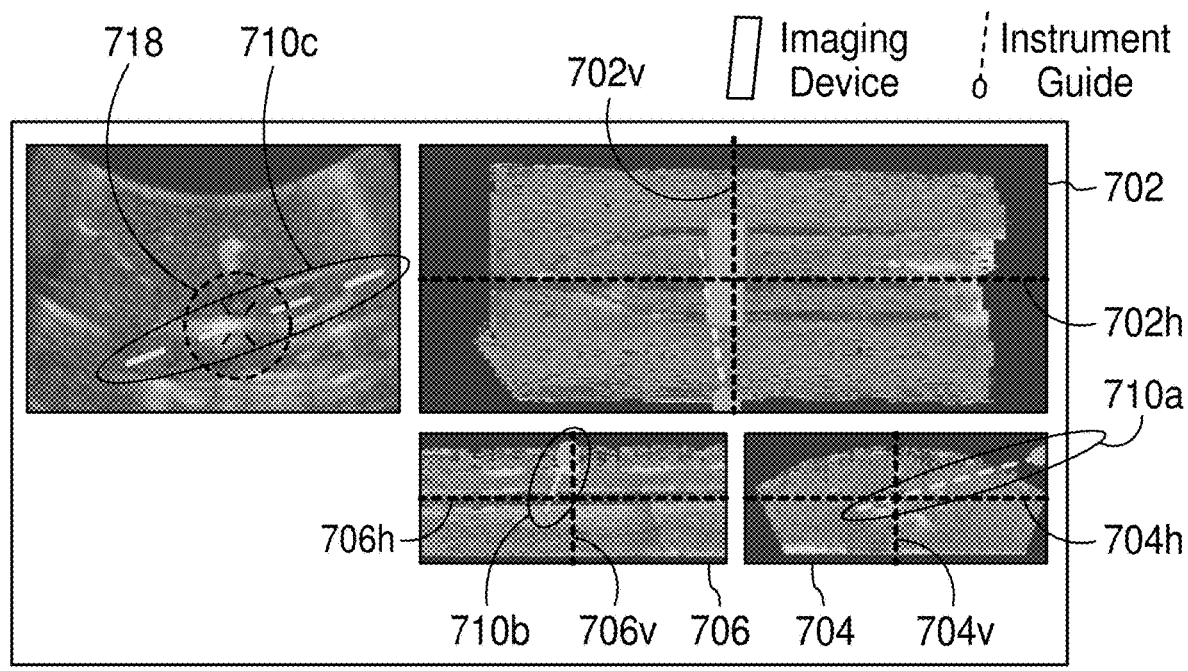

As shown in FIG. 7I, symbols 710a and 710b in images 704 and 706, respectively, represent the desired path for the instrument, indicating that the HCP has adjusted the pose of the instrument guide to prepare for instrument insertion.

Figure 7K:
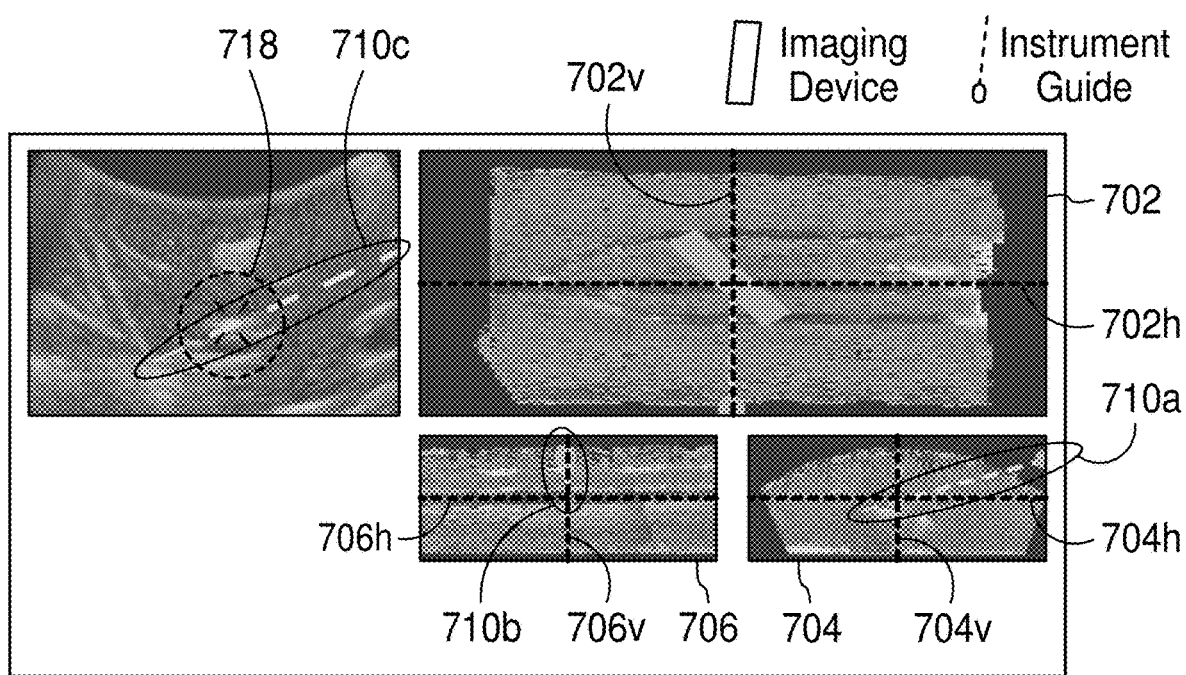

As shown in FIG. 7K, symbols 710a, 710b, and 710c indicate that the instrument guide pose is properly aligned such that symbols 710a, 710b, and 710c pass through the target. This indicates to the HCP that the instrument guide is aligned in all three dimensions with the target and that an instrument inserted into a patient's body will follow the path illustrated by the instrument guide and instrument trajectory symbols 710a, 710b, and 710c to reach the target. This ends the targeting phase.

3D Reconstruction & Localization (i.e., RecLoc)

3D Reconstruction refers to collecting, analyzing, creating, and displaying volumetric imaging (e.g., ultrasound)

data of an object (e.g., anatomical region of a body) to present a human interpretable rendering of the anatomy for procedural planning, as well as assisting in automatically planning the procedure. This includes the anatomy of interest as well as surrounding anatomy for detailed trajectory planning.

Localization refers to computing the position and orientation of the Imaging Device with respect to the patient and volumetric imaging data. This volumetric data is typically the 3D Reconstruction. Localization refers to identifying the current position and orientation of the Imaging Device with respect to the scanned anatomy. Localization may identify the location of anatomy in space relative to the robot as well as any trajectory planning primitives defined as a result of analyzing or interpreting the volumetric data, whether it be by a human or computer.

3D Reconstruction and Localization techniques may be used for Intelligent Targeting, and may also be used to enhance Basic Targeting. For example, 3D Reconstruction techniques may be used to generate a 3D rendering of ultrasound images of human anatomy, localization techniques may be used to precisely locate a target in the anatomy, and Basic Targeting (or Intelligent Targeting) may be performed for instrument insertion.

In some embodiments, IGRIS may perform 3D Reconstruction of an object and Localization using different techniques, including (1) External Sensing RecLoc, (2) Image Analysis RecLoc, or (3) combining both External Sensing RecLoc and Image Analysis RecLoc techniques to overcome deficiencies in each technique when used individually.

External Sensing RecLoc refers to techniques to generate 3D Reconstructions and perform Localization using external sensing paradigms. For example, IGRIS may utilize fiducial based techniques, such as one or more sensors (e.g., cameras) coupled to IGRIS to monitor its pose relative to the patient, and/or one or more sensors that may make contact with the fiducials (e.g., fiducial patterns analyzed by a camera that is in contact with the fiducial pattern, similar the operation of an optical mouse). In some embodiments, the fiducial patterns (e.g., ArUco) may be imprinted on a thin film dressing (e.g., tegaderm). External Sensing RecLoc techniques are very fast and robust to large or broad motions. However, External Sensing RecLoc may be limited to the area of the fiducial and does not account for deformations between the skin and anatomy. Inertial systems are even worse as any patient motion is not compensated for. External Sensing RecLoc is discussed in further detail below.

Image Analysis RecLoc refers to techniques to generate 3D Reconstructions and perform Localization, such as Neural Volume and Frame to Frame. These techniques are specific examples of a broader class of techniques called Slice-to-Volume. This class of algorithms attempts to stitch slices of ultrasound images into self-consistent volumes. Neural Volume techniques generate precise renderings and may include imaging (e.g., ultrasound) physics and deformation, but may require excessive computation cycles to perform and may require dense amounts of data. Frame to Frame techniques are limited to small inter frame displacements, require training data, and may be directionally ambiguous with respect to out of plane motion. Image Analysis RecLoc is discussed in further detail below.

Combining both External Sensing RecLoc and Image Analysis RecLoc techniques may overcome the deficiencies of each individually. This is discussed in further detail below.

External Sensing RecLoc

External Sensing RecLoc refers to techniques to generate 3D Reconstructions and perform Localization using external sensing paradigms. For example, IGRIS 100 may generate a 3D Reconstruction by using external sensors to generate additional metadata regarding the pose of the Imaging Device 146 while capturing a plurality of real-time images.

External Sensing RecLoc techniques may include tracking the pose of Imaging Device 146, (1) using cameras located around the procedure room, (2) using cameras located on IGRIS 100 (e.g., a constellation of cameras on top of the robotic assembly or imaging device), (3) using fiducial markers (skin texture, lighting patterns).

For example, IGRIS 100 receives a first plurality of real-time images generated from Imaging Device 146 scanning an object (e.g., human anatomy) sufficient to generate a 3D Reconstruction. In some embodiments, IGRIS 100 may use external sensors to generate metadata related to the first plurality of real-time images with additional information related to IGRIS 100 (e.g., pose, kinematics, velocity, movement, angle, direction, etc. of each of the components of IGRIS 100, image metadata, such as timestamp, resolution, etc.) when each of the real-time images were captured. The metadata may come from various sources, such as sensors, cameras, imaging (e.g., MRI, Ultrasonic Imaging, CT, Fluoroscopy), fiducials, LIDAR, etc.) In some embodiments, certain sources, such as sensors and cameras, may be coupled to IGRIS 100 itself, and/or dispersed around the room to track IGRIS 100 and the anatomy.

In some embodiments, fiducials may be utilized as reference points to generate additional metadata. Fiducials may refer to objects used as a point of reference placed in the procedural field and sensed to compute the pose of the imaging system and/or IGRIS. Fiducials may be either something placed into or on the patient or in the room.

In some embodiments, sensor inputs to estimate inertial probe motion may come from inertial sensors or by measuring the motion with respect to inertially stationary objects like the room itself. Sensors may be placed in the room and track the probe motion, or placed on the probe to track the apparent motion of external objects. These sensors include Inertial measurement units ("IMU"), Magnetometer, Altitude sensors, On-device cameras (optical flow, feature tracking, QR codes, optical mice sensors), LIDAR, Structure light sensors (e.g. Microsoft Kinect), Electromagnetic sensors (e.g. Polhemus sensors, magnetic hall distance sensors, capacitive distance sensors), Room-mounted camera-based motion capture apparatuses (e.g. OptiTrack), Encoders attached to external holding apparatuses, Reference using sound vibrations either from the Instrument or Imaging Device 146, or other sensors that may be understood by one of ordinary skill in the art.

As an example, External Sensing RecLoc may analyze images from a camera that capture fiducial markers attached to the surface of the object (e.g., skin of the anatomy). Examples of such fiducial markers may include a patch that sits on the skin. The patch may include a unique imprint (e.g., bar code, QR code, ARTag, ArUco markers, known patterns, etc.) which may be used to provide further metadata related to the first plurality of real-time images. The output of the image analysis is a six degree of freedom pose estimate of the camera including position and orientation. The camera may be coupled to IGRIS, which allow the poses to be mapped to poses of the Imaging Device 146. These techniques can be used to achieve reconstruction and localization as a standalone system.

However, an issue that may arise because the underlying anatomy is known to shift and deform relative to external features/fiducials. To overcome this relative motion, "skin localization" may be used to initialize real-time image (e.g., ultrasound) based pose estimation.

External sensing may compute in real-time the pose of a newly scanned image in the 3D Reconstruction. This estimate may be used to initialize or seed a real-time image localization algorithm across a short pose baseline in the neighborhood of the estimate.

When registering coordinate frames among an Imaging Device, a robotic instrument targeting system, and an object (e.g., patient anatomy of interest), more than one approach may be implemented.

In some embodiments, an array of beacons and observers may be used, whereby markers can be affixed to the patient via adhesive or other means to create a reference frame, inside of which the movements of the probe and robotic instrument targeting system assembly can be tracked. Methods to be employed may include time-of-flight, time difference of arrival, or other means of determining relative position among beacons and observers.

In another embodiment, a known pattern on the patient's skin over the intended procedural anatomy may be created. A known pattern could be created and observed in the following ways: Printing a deterministic pattern on a transparent layer (e.g., such as a sterile plastic film), and utilizing sensors to track the pattern motion and thus the Imaging Device (e.g., probe) and robotic instrument targeting system assembly (e.g., modular robotic arm) position over the transparent layer. The approach to performing such measurement may range from printing markers onto a transparent layer and reading known patterns with an array of optical cameras to using imperceptible markers and patterns that could be read by a sensor capable of viewing non-visible light spectrum. The primary benefit of this technique would stem from the pattern being adhered or fixated to patient anatomy. By combining a deterministic pattern on the patient's skin, an inertial measurement unit, and Imaging Device (e.g., ultrasound), the system may re-register and re-localize previously planned targets. In some embodiments, specific types of transparent layers with known patterns may be generated for specific clinical applications providing the system with information that could modify, change, or guide system software parameters.

In some embodiments, a technique of "skin localization" (e.g., using the skin patterns of the anatomy as a reference point) may be used to compensate for variations in the images due to shifting of skin.

If the external features/fiducial of the skin created a rigid body with the underlying anatomy, this would be sufficient to create accurate reconstructions by concatenating a number of ultrasound images with their pose estimates. Similarly, localization of new images could be achieved by comparing the pose of the new image to the reconstruction coordinate frame.

Figure 14:
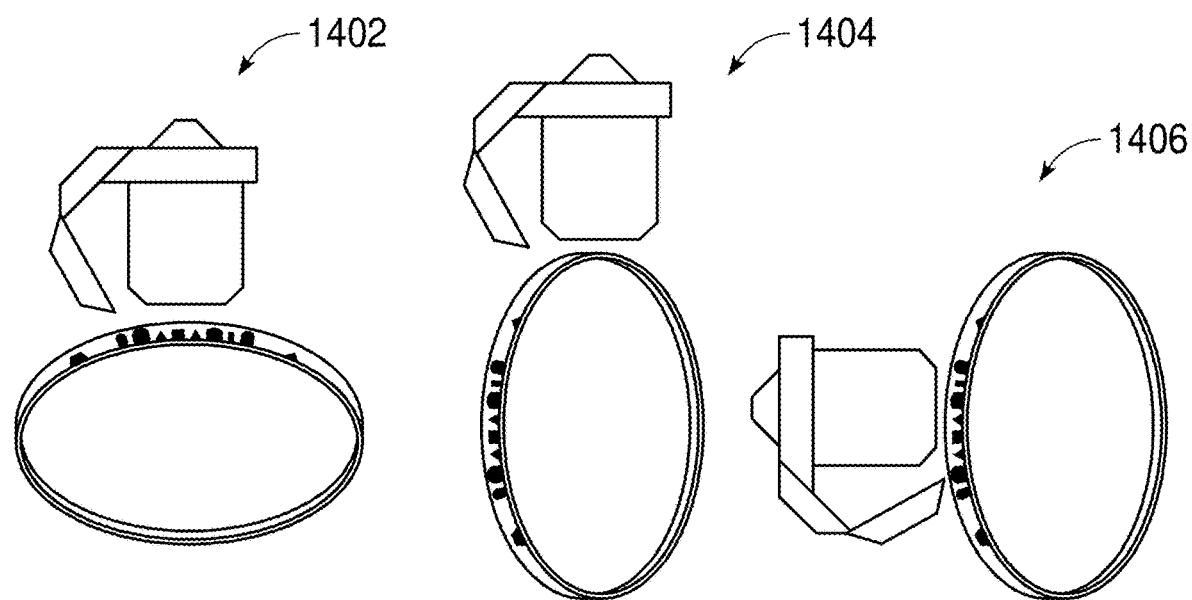
FIG. 14 illustrates an Imaging Device using a known pattern (e.g., ArUco) in a thin film dressing (e.g., tegaderm) to localize the pose of the Imaging Device.

Referring now to FIG. 14, localization techniques using a known pattern (e.g., ArUco) in a thin film dressing (e.g., tegaderm) to localize the position of an Imaging Device (e.g., ultrasound probe) and modular robotic arm are illustrated. In some embodiments, these techniques may also be performed by IGRIS 100.

The first panel 1402 illustrates the Imaging Device and modular robotic arm using a known pattern on a thin film dressing attached to a patient's arm. The Imaging Device (e.g., ArUco, shown on the pattern on the cross section of the patient's forearm) to localize the position of the Imaging Device (e.g., ultrasound probe) and modular robotic arm with respect to the patient. The second panel 1404 illustrates the modular robotic arm rotated 90 degrees, and registration and localization is temporarily absent. The third panel 1406 illustrates the Imaging Device (e.g., probe) and robotic arm repositioned to find the previously known pattern, and using positional information from IMUs, the Imaging Device (e.g., probe), the robotic arm, and the real-time images may be re-registered to one another.

In another embodiment, structured light could be projected onto the patient's skin over the intended procedural anatomy. This embodiment would forego the need to affix a known pattern to the patient. Rather, a light pattern would be emitted from a device or apparatus onto the anatomy of interest. That light pattern would be recognized or detected with optical sensors which could then provide positional information about the probe and the robotic instrument targeting system relative to the patient anatomy.

Figure 15:
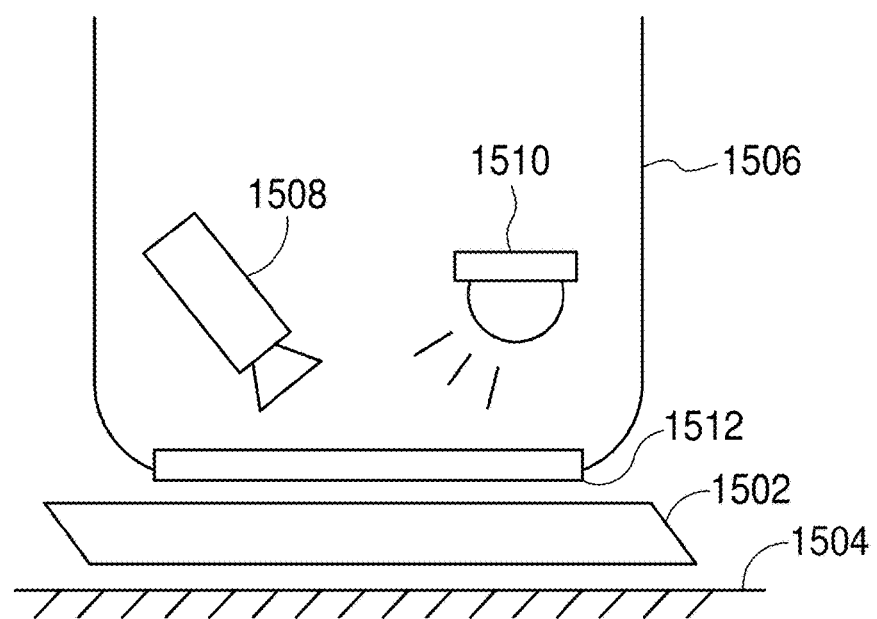
FIG. 15 illustrates an encoder that analyzes fiducial patterns (e.g., ArUco) analyzed by a camera.

Referring now to FIG. 15, an encoder that analyzes fiducial patterns (e.g., ArUco encoder) may be employed where fiducial patterns are analyzed by a camera that is in contact with the pattern similar to an optical mouse. The invention provides extremely high relative displacement between the surface 1504 and the instrument 1506. As shown, the surface 1504 may be the skin of a patient and the Imaging Device 1506 may be an ultrasound device.

The encoder may comprise a light emitter 1510 that illuminates the sticker 1502 through a protective lens 1512 and the illuminated pattern is captured by a camera 1508. Because of the unique fiducial pattern on the transparent layer, the camera 1508 is able to uniquely identify its corresponding placement relative to the pattern on the transparent layer.

In some embodiments, translucent materials between the sticker 1502 and the lens 1512, such as coupling gel or sanitary barriers, may be used.

The fiducial pattern (e.g., ArUco) encoder method provides: (1) imperviousness to any occlusions that may occur during a procedure; (2) imperviousness to lighting conditions due to the fact that the direct contact enforces no external lighting, and the sensor provides its own light; (3) flexibility in terms of scale and precision by simply modifying the patterns on the image; (4) absolute positioning assuming the pattern is unique at every point where, unlike other optical flow algorithms, one can return to the target; (5) camera sensor profiles such that the sensors may be shifted to better facilitate any procedures where, in one example in which fluorescent ink is selected, the sticker can be near transparent to the user, but fluorescent using a special UV light as a source; (6) robustness to translucent sanitary barriers (drapes), and wrinkles or folds or detritus (band aids, blood, powders) provide direct contact between the skin; and (7) robustness to translucent gels such as ultrasound coupling gel.

Figure 16:
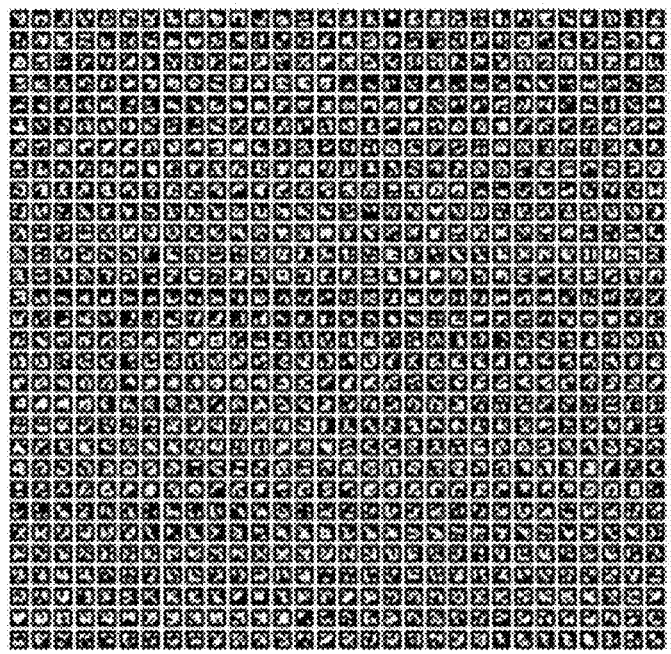
FIG. 16 illustrates an embodiment of a fiducial pattern (e.g., ArUco) that can uniquely identify its position in the entire grid.

Referring now to FIG. 16, the pattern of the sticker may include ArUco markers that can uniquely identify its position in the entire grid. A snapshot of a small subset of the grid may be sufficient to uniquely identify where the instrument is relative to the entire sticker.

In some embodiments, a similar approach may be taken where the cameras are mounted higher up on the Imaging Device handle. By way of longer focal length camera optics (mini zoom camera), the fiducials may be appear as if the camera was in close proximity with the sticker. In some embodiments, a camera may be embedded at the base of the robot near the probe adapter. The camera observes a region of the ArUco pattern near the probe and computes the absolute pose of the probe relative to the known ArUco array by way of tracking, calibrations and any required robot kinematics.

Image Analysis RecLoc

Image Analysis RecLoc refers to techniques to generate 3D Reconstructions and perform Localization, such as Neural Volume and Frame to Frame, by analyzing the images without external sensor metadata. In some embodiments, Image Analysis RecLoc may use metadata from various sources, such as previously performed scans from various imaging (e.g., Ultrasound, MRI, Ultrasonic Imaging, CT, Fluoroscopy).

Neural Volume

Neural volume techniques may include a process that ingests real-time images (e.g., ultrasound) of an object (e.g., anatomical target) and outputs both an anatomical model that is positionally self-consistent and a registration function that can register new real-time images to the model. This process may be robust to common ultrasound imaging complexities such as the view-dependence of various anatomical structures and deformation of the anatomy.

For example, a short sequence of real-time images may be collected and fit together in 3D space such that they form a coherent volumetric structure. This may be performed as a numerical optimization, which minimizes the difference between the recorded images and synthetic images inferred from the volumetric model.

During the process, an optimization is performed on both the poses and the volumetric model so that a volumetric representation of the scanned anatomy is created and the original images are registered to the volumetric representation simultaneously. Subsequent real-time images may be registered to the volumetric model via a similar optimization process that freezes the volume parameters while searching for the optimal pose of the new image.

In some embodiments, Neural Volume may comprise a single optimization technique to perform both 3D Reconstruction of an anatomical volume and Localization of new frames without multiple optimization objectives or data formats. Neural Volume may also be naturally extensible to higher dimensionality of the volumetric model (such as adding 3D view-dependence to each point in 3D space) by capturing the real-time image field in a highly non-linear parametric model as opposed to a more rigid grid-based model.

Figure 9:
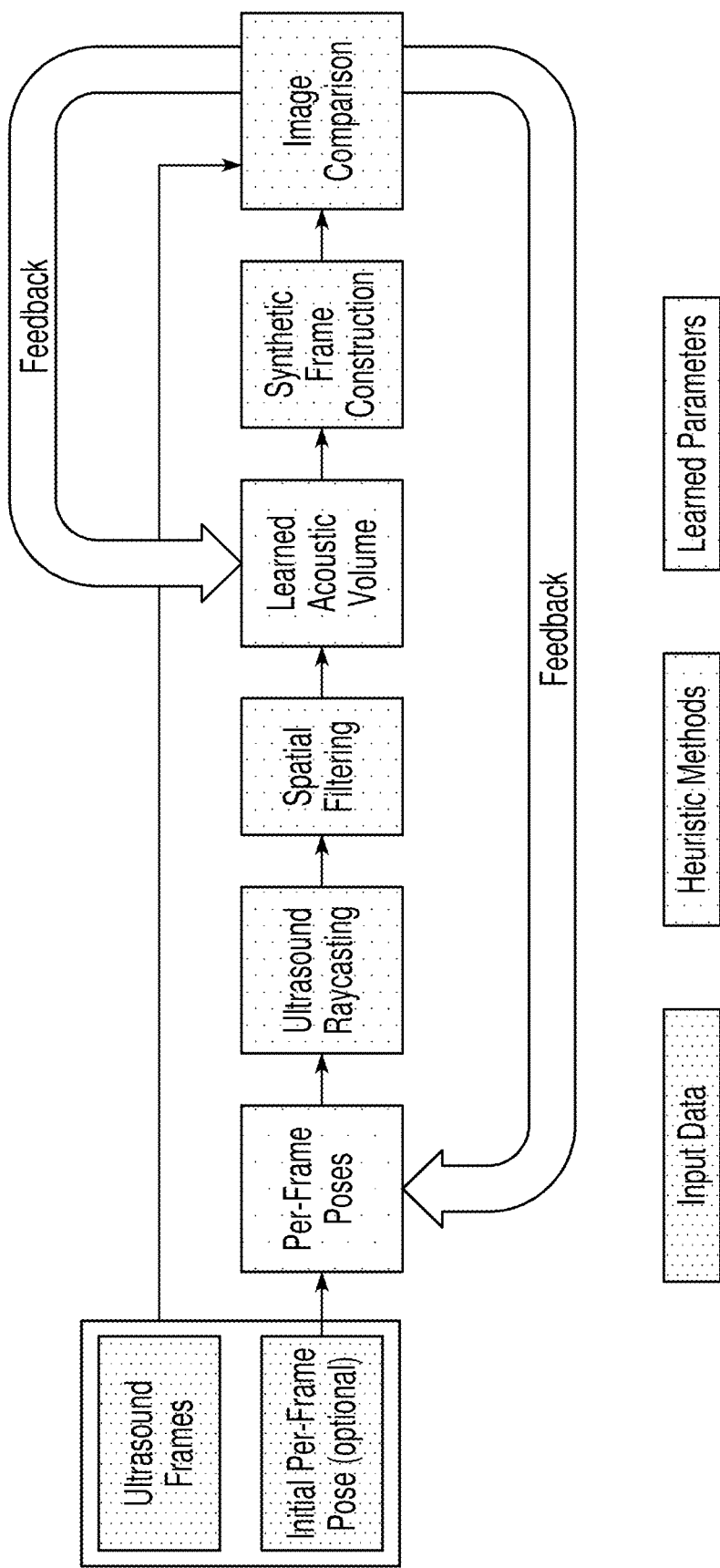
FIGS. 9-10, inclusive, illustrate an embodiment of a flow of a single optimization technique used to perform localization.

Referring now to FIG. 9, a flow of the same single optimization technique is used to perform localization of new frames without multiple optimization objectives or data formats.

The technique begins capturing input data, including a sequence of real-time images (e.g., ultrasound) of an object (e.g., anatomy) and an optional initial per-frame pose (e.g., device positions and orientations for each frame) and saving the data to a computer. If no initial per-frame pose is provided, an estimated initial per-frame pose may be calculated based on heuristics.

The real-time images and device poses may be fed to an optimization technique that iteratively adjusts both the device poses and the weights of a parameterized model that represents the acoustic intensity at each point in space that was captured in the ultrasound images. This volume model may take many forms, but generally is able to fit to high-dimensional and nonlinear data relationships, such as a neural net. The model may be set up to predict the acoustic intensity of any point in 3D space as a function of view angle, and so by evaluating this on a grid of points in space can be used to synthesize real-time image frames from any point of view.

Each individual probe pose may be converted to a grid of 3D points in space corresponding to each pixel in the corresponding ultrasound image using traditional raycasting and knowledge of the probe imaging characteristics. Referring to FIG. 9, the objective of the optimization is to minimize the difference between the recorded ultrasound image and the synthetic images at the assumed device poses for each input frame. This optimization method uses the assumed self-consistency of the ultrasound sequence with respect to the target anatomy to jointly derive the poses and volume model that results in a model that can accurately reproduce the input sequence. Once the optimization technique has reached a suitably low difference between the input sequence and the synthetic images at those poses, the optimization stops and the final poses are output as the poses that co-register the input sequence.

The parameterized model can generate synthetic images from arbitrary vantage points. As such this can be used to generate volumetric representations that are displayed to the user.

Figure 10:
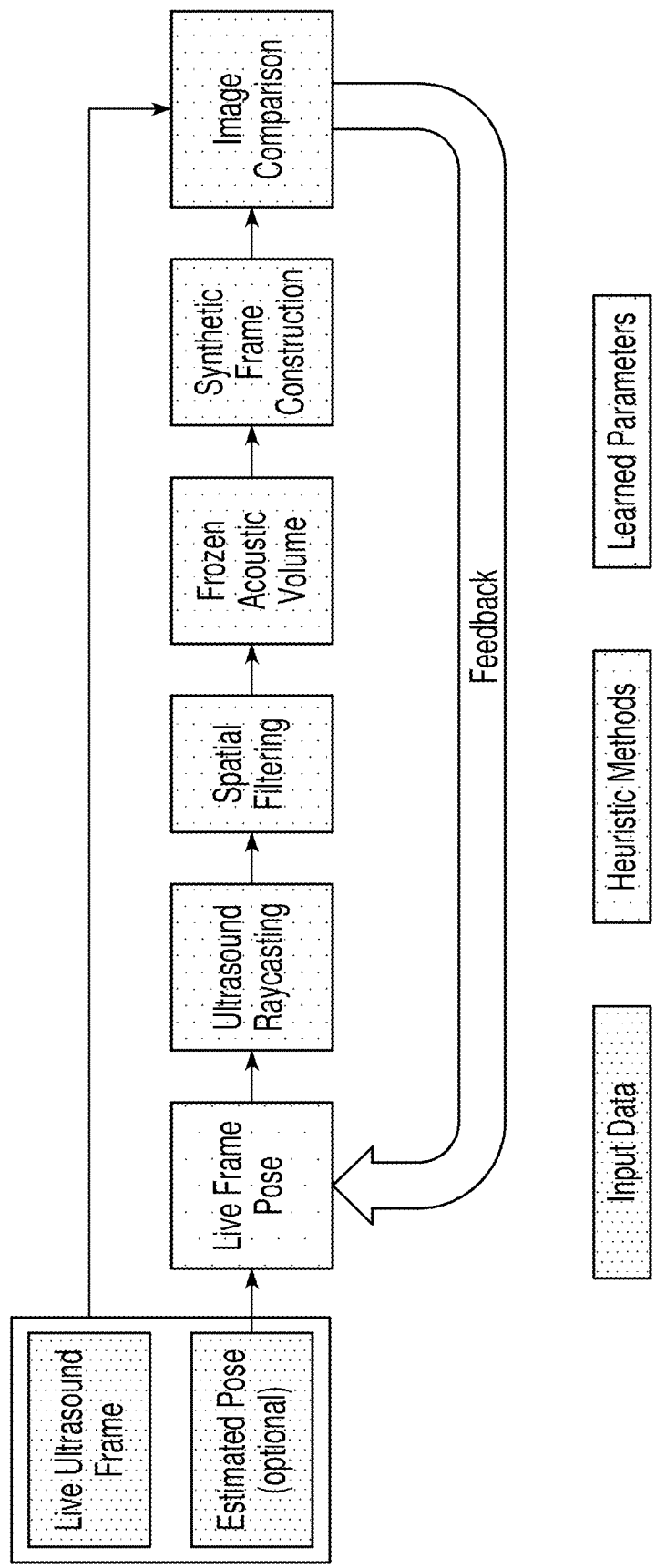

Referring to FIG. 10. this parameterized model can then be 'frozen' such that the parameters are no longer updated, which allows the model to ingests additional real-time image frames that were not part of the original input sequence and optimize only for the pose of these new frames. This process is essentially localizing new real-time images relative to the pre-recorded anatomical volume (e.g., 3D Reconstruction).

Beneficially, unlike methods that capture the volumetric acoustic intensity field as an explicitly volumetric data type (i.e., a 3D grid of voxels), neural volume techniques allows the volume to be stored in far fewer parameters by allowing the optimization to preferentially use more parameters for high-detail regions and fewer parameters for low-detail regions of the anatomy. Neural Volume may be able to find sparse patterns in high-dimensional data, allowing it to remain much smaller in complexity as the dimensionality increases. For example, extending a voxel grid from capturing 3D input data to 6D (adding view-dependence).

Moreover, the method of heuristically translating each real-time image pixel to a location in 3D space via raycasting (given a probe pose) allows for simple extensibility of the method to Imaging Device types and explicit accounting for various real-time image (e.g., ultrasound) artifacting. The parameters controlling the raycasting may be measurable by calibrating a new Imaging Device or by obtaining imaging parameters from a manufacturer, and updating these does not require any additional data collection for training ahead of time. This raycasting may be easily enhanced to account for a variety of other physics-based real-time image (e.g., ultrasound) effects like beam spreading and echoing which allows the optimization to at least partially undo these effects when learning the underlying anatomical representation.

Finally, since this optimization method only relies on the approximate self-consistency of different views of the same anatomy, it can be applied to a wide variety of clinical applications without the need for extensive and varied training data on patients.

Frame to Frame

Frame to Frame techniques describe a method of co-registering pairs of real-time images (e.g., ultrasound) using a machine learning model for the purpose of creating 3D volumetric reconstructions and performing real-time localization of real-time image frames to an existing 3D Reconstruction.

The techniques may include first training a neural network on data collected from a variety of patient anatomies where we have collected ground-truth data on the pose of the real-time images (e.g., ultrasound). Pairs of real-time images and the difference in pose between them may be presented to the model for training so that the model learns to approximate a function that maps image pairs to pose differences. The trained model may take in two real-time image frames taken from the same patient anatomy and output an estimation of the pose difference between the two images. This model may then be used in two ways: co-registering a sequence of images together to create a coherent anatomical reconstruction (e.g., 3D Reconstruction) and registering single images to an existing reconstruction (e.g., Localization).

Performing either of the two related tasks of co-registering a series of ultrasound images or registering individual ultrasound images to an anatomical reconstruction may be performed as a two-step process.

Figure 11:
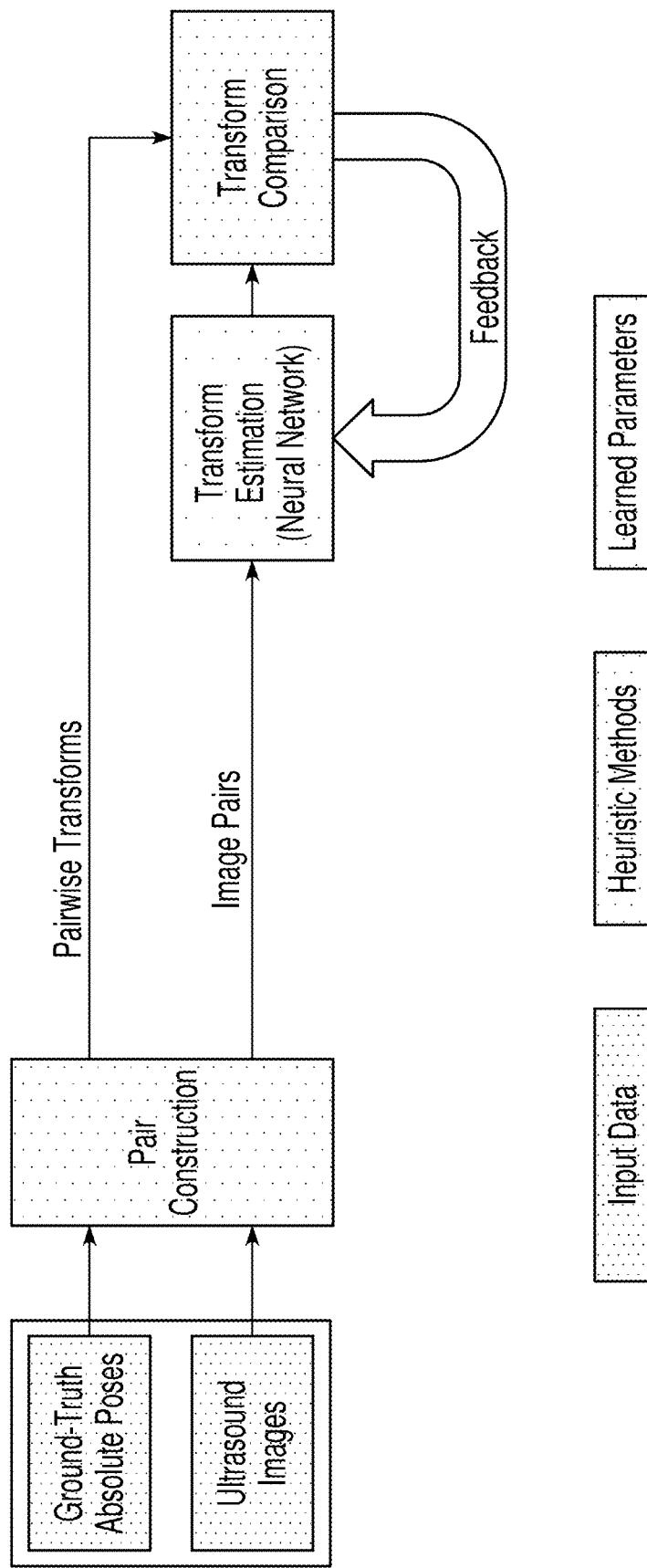
FIGS. 11-12, inclusive, illustrate an embodiment of a flow of a single trained network used for both reconstruction and localization.

Referring now to FIG. 11, the first step is to train a neural network to estimate the full positional and rotational transform between two real-time images (e.g., ultrasound). To perform this neural network training, ground-truth data is collected from a set of patients, and the absolute pose of an Imaging Device for every image taken by the device of the patient anatomy is recorded. The real-time images may be obtained via scans of patient anatomy as a series of sweeps or passes over a relevant anatomy, varying the position and view angle of the Imaging Device over each pass to create a variety of view offsets and directions over the same regions.

This ground-truth data may be used in training the neural network by presenting the network with examples of pairs of images as the input and the difference in absolute position and rotation between those same two images as the target output. While the collected data may contain pairs of images with possible transforms that span a wide range of values, the training pairs are limited to images that are collected within a small local region of each other (typically <2 cm). The network may take a variety of forms, all generally consisting of a sequence of neural network layers that process the input image pair and output a position and rotation transform. This network is trained over a large set of image-transform pairs that spans a variety of patients with varying anatomical detail. The final model, once trained, is capable of estimating the transform between two input real-time images for scans done of patients not seen in the training data.

Figure 12:
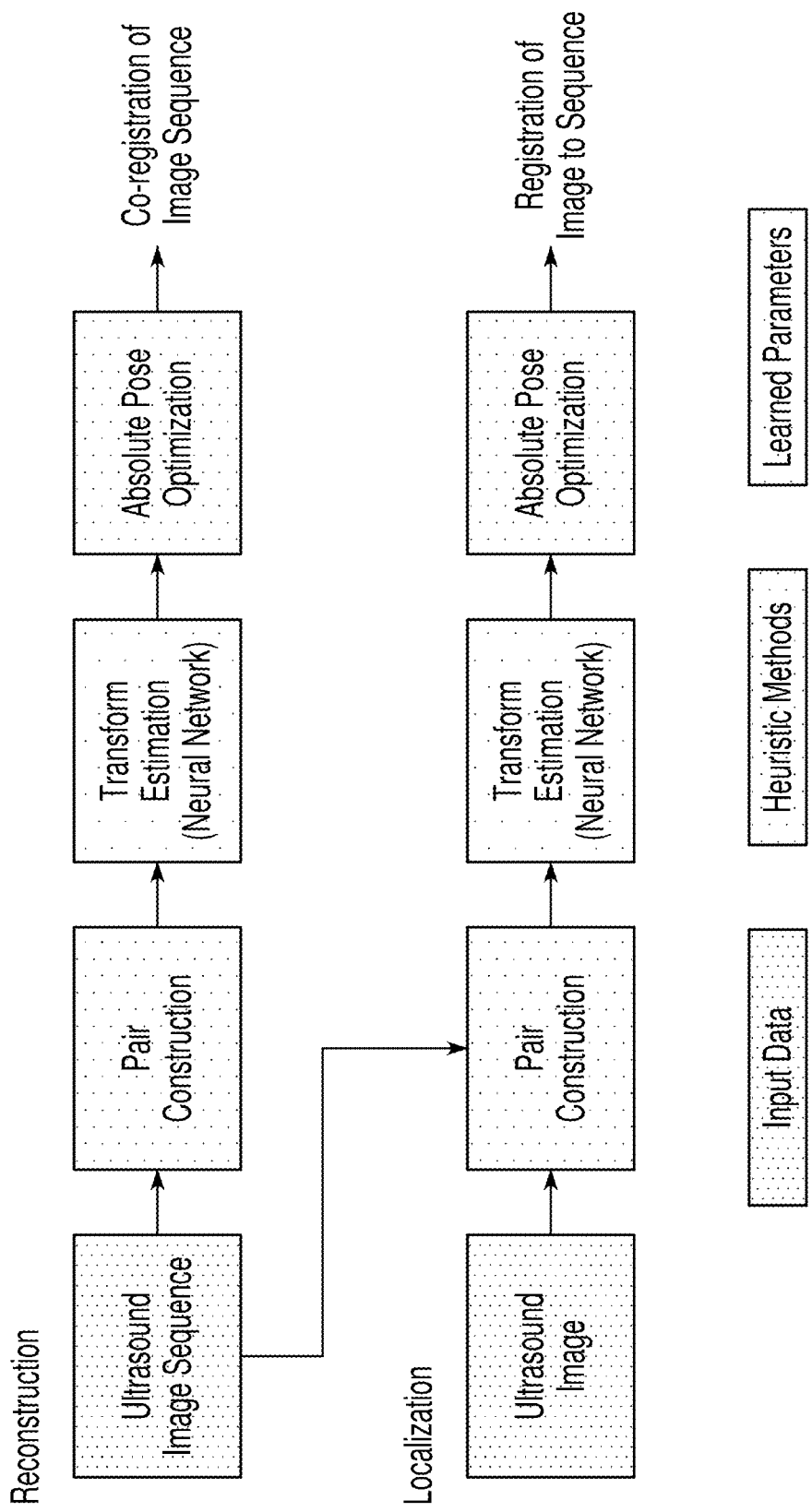

Referring now to FIG. 12, the second step is to use this trained model on new patients and real-time image (e.g., ultrasound) scans to either create anatomical reconstructions by way of co-registering a sequence of images, or to register individual images to a previously-created reconstruction. For example, for co-registration of a sequence of images, a given sequence of N images may be reorganized as a set of N*N image pairs representing every possible pairing of images from the sequence. The trained model may be run on each pair to create a set of N*N transform estimations. Then, a set of N absolute poses (that represent the poses of the Imaging Device for each recorded real-time image) is solved by optimizing these poses to minimize the difference between the model-estimated transforms and the corresponding transforms between each pair of optimized poses. This process may implicitly co-register the input sequence of real-time frames to each other. Different visualizations may be created of the patient anatomy using the image sequence and corresponding pose, such as by using the pose data and ultrasound imaging parameters (depth, width, etc.) to project the image pixels into 3D voxels and rendering cuts or volumetric renders of the data.

In another embodiment, the trained transform estimation model may be used to localize individual real-time (e.g., ultrasound) images to an existing 3D Reconstruction. To begin, start with a sequence of images and their optimized poses previously created to find the pose of a new real-time image that was not part of the original sequence relative to that sequence. Frames are organized to create a set of N image comparisons, where one image is from the pre-recorded sequence, and the other frame of every comparison is the new real-time image. The trained transform estimation model may be run on each image pair to create a set of N estimated transforms that describe the transform between the new image and the original sequence. Then, the new image to the sequence or reconstruction may be registered by creating a similar optimization problem as before, or more simply, each transform estimation may be looped through to find the pair with the smallest magnitude transform (which often implies highest accuracy of transform estimate) and use the single estimated transform of this image from the original sequence as the transform that registers the new image to the sequence.

Beneficially, compared to processes that only perform reconstruction or single-frame registration, our method shares one trained network for both tasks meaning we can accomplish two key tasks (reconstruction and localization) with one core system.

Frame displacement describes techniques identifying the displacement between real-time images to generate a 3D Reconstruction. For example, IGRIS 100 receives a first plurality of real-time images generated from Imaging Device 146 scanning an object (e.g., human anatomy) sufficient to generate a 3D Reconstruction. In some embodiments, IGRIS may also require a threshold quantity of real-time images for the first plurality of real-time images to generate the 3D Reconstruction. In some embodiments, IGRIS 100 may include an indicator (e.g., a hardware indicator, such as an LED, or a software indicator on the User Interface) that a sufficient quantity of images has been acquired.

In some embodiments, the plurality of real-time images are generated in a manner such that there is sufficient intersection points in each neighboring image. For example, a user may scan human anatomy using an ultrasound probe in various patterns (e.g., an S shape, 45 degrees, etc.) to achieve sufficient intersection points between each neighboring image.

In another embodiment, the plurality of real-time images are generated, where the plurality of real-time images include a first set of real-time images scanned in a first direction, and a second set of real-time images scanned in a second direction. Preferably, the second direction is substantially orthogonal to the first direction but may not be required so long as the first direction and second direction are not identical.

With sufficient intersection points, IGRIS may perform cross-stitching of the neighboring images to identify common or corresponding points between them. Or alternatively IGRIS may use the neural volume techniques previously described.

IGRIS 100 may perform the correlation in a variety of ways, including (1) estimation of probe motion between two consecutive B-mode image frames, (2) estimation of probe motion from a long series of B-mode images, (3) matching a B-mode image to an existing 3D ultrasound volume by optimizing an image-to-volume similarity metric, (4) jointly optimizing the estimated poses of a series of B-mode images by optimizing an image similarity metric, or others that may be known to one of ordinary skill in the art. IGRIS 100 may utilize both data-driven (machine learning) algorithms and heuristic algorithms to perform the correlation.

B-Mode is a two-dimensional ultrasound image display composed of bright dots representing the ultrasound echoes. The brightness of each dot is determined by the amplitude of the returned echo signal. This allows for visualization and quantification of anatomical structures, as well as for the visualization of diagnostic and therapeutic procedures for small animal studies. Aspects of the present invention also operate with other modes of imaging, including and not limited to A-mode, B-mode (2D, extended 2D, 3D), M-mode, Doppler, Speckle-tracking, Tissue Harmonic Imaging, raw transducer data, and combinations of imaging modes.

From this volumetric model, simulated ultrasound scans can be generated by artificially taking slices of the 3D model using simple interpolation of the voxels or some more complex neural net algorithms to generate images of high quality. IGRIS 100 generates the 3D mapping by computing the pose (position and orientation) of a number of ultrasound images and render them as a three dimensional volume by unionizing them appropriately.

Combining External Sensing RecLoc with Image Analysis RecLoc

External Sensing RecLoc and Image Analysis RecLoc techniques individually may generate sufficient 3D Reconstructions for use with Localizations on their own with some drawbacks that may compromise the quality of the 3D Reconstruction and affect Localization. However, combining External Sensing RecLoc with Image Analysis RecLoc overcomes many of the drawbacks of each.

Some External Sensing RecLoc techniques (e.g., using cameras) may have issues, such as difficulty compensating for patient movement, shifting of skin or internal anatomy, or compensating for anomalies from the Imaging Device itself (e.g., odd shadows in Ultrasound images). Other External Sensing RecLoc techniques (e.g., using fiducials, or skin patterns) may compensate for shifting of skin or patient movement, but may have difficult compensating for shifting of internal anatomy.

Image Analysis RecLoc techniques may overcome the deficiencies of External Sensor RecLoc techniques, but may come at the expense of time and processing cycles required optimization algorithms to converge. Additionally, for example, Frame to Frame operates well with short baseline operations (e.g., processing images that have a higher statistic relationship between each other, such as comparing two images of a heart from different angles), but not as well with wide baseline (e.g., processing images that have a lower statistic relationship between each other, such as comparing an image of a heart and an image of the calf).

Combining (or fusing) External Sensing RecLoc with Image Analysis RecLoc provides: (1) robustness to large motions due real time computation and absolute accuracy of external sensing; (2) accurate ultrasound based pose estimation by using external sensing as an initial condition or seed for image analysis, thus reducing the baseline of the estimate; (3) reduced runtime complexity of ultrasound based pose estimation; (4) disambiguation of out of plane ultrasound estimation due to skin sensing; and (5) robustness to ultrasound anisotropy due to image analysis techniques.

For example, real-time image (e.g., ultrasound) based pose estimation may be well suited for machine learning algorithms. Given a first real-time image and an initial pose estimate, a neural network can be trained to estimate the actual pose of the first scan relative to a second scan or a number of scans with known poses. The model may be trained in a way that is generic to human anatomy because it learns the statistics or model of adjacent real-time images in humans. This algorithm may be used to iteratively create 3D Reconstructions, or search in a local region of volumetric data to perform localization. Datasets generation and real-time inference runtime are both tractable.

For example, External Sensing RecLoc techniques may be used reliably to provide an estimation of image/probe pose pairs. This estimation may be used with, or to seed, Image Analysis RecLoc to reduce the time and processing required to generate 3D Reconstruction. In some embodiments, the Image Analysis RecLoc my search a smaller optimization space to perturb these initial estimates and upgrade the reconstruction to be more accurate. This decreases optimization cycles and improves runtime.

For example, combining "skin localization" techniques to initialize ultrasound based pose estimation with Image Analysis RecLoc may overcome relative motion issues (e.g., the underlying anatomy may shift and deforms relative to external features/fiducials, such as the skin) with skin localization alone.

For 3D Reconstruction, the "skin localization" may be used to initialize or seed an image based pose estimation algorithm. Frame to Frame like algorithms loop over the images and pose estimates as inputs, and estimate an upgraded solution that is more consistent and accurate with the information in the images themselves. This could be done in a batch fashion simultaneously over a set of images, or iteratively as new image/pose pairs are scanned by the system. The result is volumetric information by way of an image set with corresponding poses. This data could be mapped to a volume that is rendered to a user for planning. However, in its raw form, it is some higher dimensional data set that considers not only a pixel to voxel mapping, but may also capture deformation and directionally dependent ultrasound imaging physics. These algorithms may also compensate and account for deformations, such as deformation of anatomy and motion of organs.

For example, Frame to Frame 3D Reconstruction tasks with fused IMU have been shown to be more accurate (e.g., on the order of 10 percent). However, they may require the scans to move in a single direction due to out of plane motion ambiguity. Further, over large distances, this error can build up and cause large reconstruction errors due to drift. These reconstructions must also be done in one pass due to the incremental integrative assembly of the reconstruction. Fusing external patient tracking information disambiguates out of plane motion and compensates for drift. It also allows multiple passes during reconstruction data collection.

Intelligent Targeting Flow

Intelligent Targeting may utilize 3D Reconstructions to plan the interventional procedure and as an input to Localization to compute the position and orientation of IGRIS with respect to the object (e.g., anatomy) and the volumetric imaging data (e.g., 3D Reconstruction) of the scanned anatomy. For example, using 3D Reconstruction and Localization techniques disclosed herein allows IGRIS to target specific areas in an object (e.g., anatomy) by analyzing the pose of IGRIS in relation to 3D Reconstructions of the object. In some embodiments, Intelligent Targeting may be used to automatically point the instrument guide to the target based on the Localization and other lower level state estimation techniques (e.g., dead reckoning). The Intelligent Targeting flow may continue with the Intelligent Targeting Backdrive or the Intelligent Targeting Tap to Target flows described below.

Figure 13A:
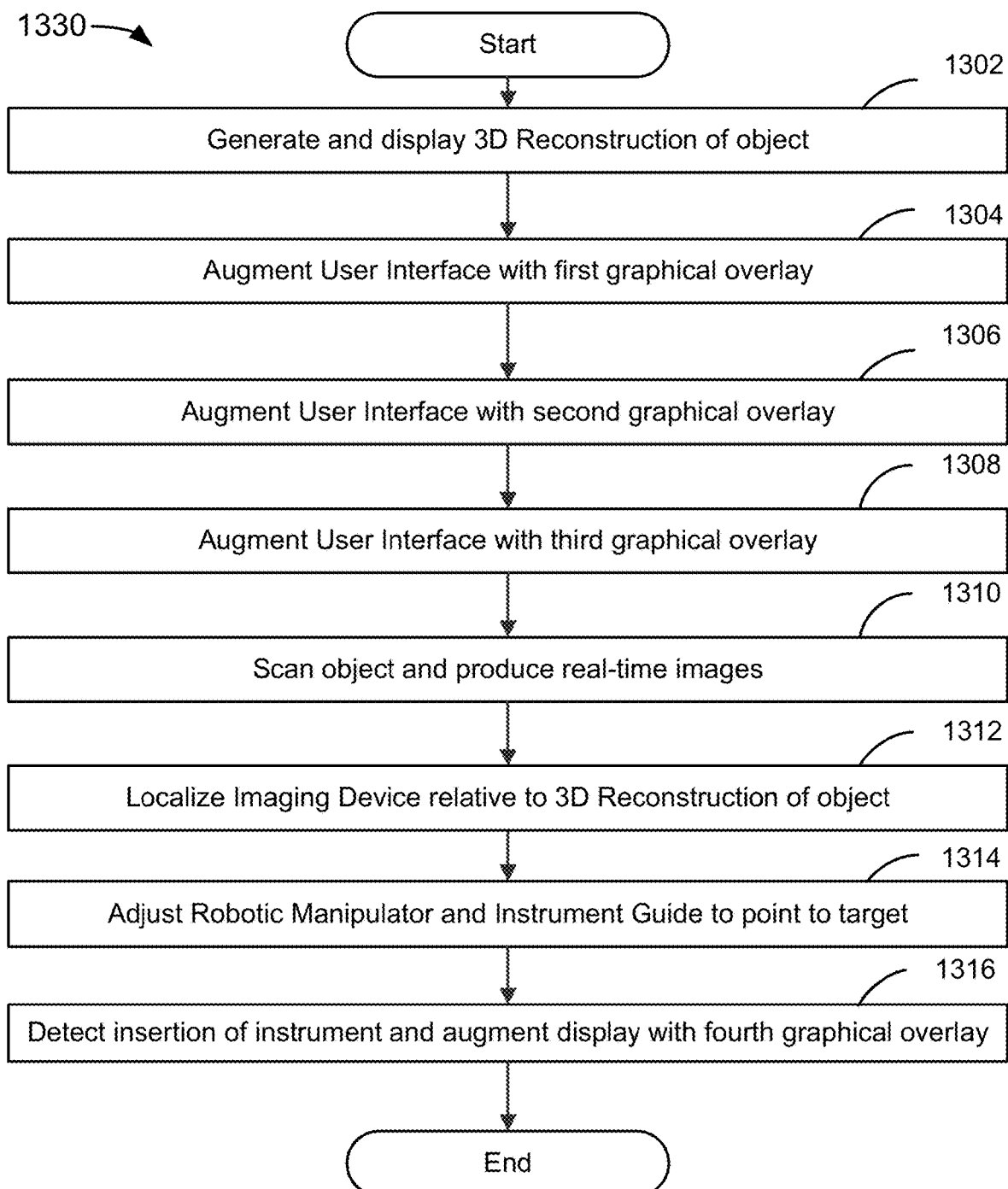
FIGS. 13A-13C, inclusive, illustrate an embodiment of Intelligent Targeting, including Backdrive and Tap to Target.

Referring to FIG. 13A, an embodiment of the Intelligent Targeting 1300 is disclosed.

In step 1302, IGRIS 100 generates and displays the 3D Reconstruction of the object on User Interface 132. In some embodiments, IGRIS 100 may use a previously generated 3D Reconstruction. The 3D Reconstruction may appear different forms, including a 3D rendering, views in different angles, etc. For example, the 3D Reconstruction may appear in coronal view (frontal), sagittal (lateral), and transverse (axial). The display of the 3D Reconstruction may be interactive and may receive input (e.g., from a touch screen, mouse, keyboard, joy stick, track ball, etc.) to manipulate (e.g., move, drag, zoom in/out, rotate, etc.) the display of the 3D Reconstruction of the object.

User Interface 132 may also display the real-time images of the object for the user to view. The real-time images are updated based on any change in pose (e.g., position or orientation) of the Imaging Device 146. In some embodiments, the User Interface 132 displays the real-time images along an X-Y axis plane.

In step 1304, IGRIS may augment the 3D Reconstruction on the User Interface 132 with a first graphical overlay that represents the pose of the Imaging Device 146 relative to the anatomy. The first graphical overlay may be updated based on any adjustment of the pose of the Imaging Device 146.

In step 1306, IGRIS 100 may augment the User Interface 132 with a second graphical overlay which represents the desired target for the final location the instrument tip inserted via the instrument guide. For example, User Interface 132 may place a target indicator over the selected target point of interest. The target indicator may appear on all available views of the 3D Reconstruction and live view. Beneficially, the target indicator may assist a user in navigating the Imaging Device 146 and/or Instrument Guide 128 towards the target anatomy based on selecting the target (e.g., localization) in the 3D Reconstruction.

In step 1308, IGRIS may augment the 3D Reconstruction and live view on the User Interface 132 with a third graphical overlay that represents the desired trajectory (or path) of the Instrument Guide 128 across or through the image. For example, the third graphical overlay provides an estimation of the path of an instrument (e.g., a needle) being inserted into the object (e.g., human anatomy) using the instrument guide. Visually, the third graphical overlay may appear as a colored solid or dotted line over the real-time images of the object, or may appear as another visualization that indicates the desired trajectory of an instrument inserted into the object using the Instrument Guide 128. The third graphical overlay may provide the user with guidance of the path the needle will travel into the object during a needle insertion.

In step 1310, the Imaging Device 146 may scan the object and produce real-time images (e.g., ultrasound imaging) of the object (e.g., human anatomy of a patient). The first graphical overlay may be updated based on any adjustment of the pose of the Imaging Device 146.

In step 1312, the Imaging Device 146 is positioned on the object such that it is localized relative to the 3D Reconstruction of the object.

In step 1314, the pose of the Robotic Manipulator 126 may be adjusted to align the Instrument Guide 128 with the third graphical overlay to point at the target in the object (e.g., anatomy).

In step 1316, IGRIS may include a mode selector input to trigger either the Backdrive or Tap to Target modes. The mode selector input may appear on the user interface as a "button" or option, or may also be integrated as a hardware indicator (e.g., a button or toggle), or any other toggle or selection method known to one of skill in the art. In some embodiments, the mode selector input may be obviated by automating detection of the preferred mode. For example, mode selection may be automated by determining the last received input of IGRIS 100 and switching IGRIS to the appropriate mode (e.g., IGRIS may switch to Tap to Target mode if IGRIS detects input is received to the User Interface, and may switch to Backdrive mode if IGRIS detects robotic manipulator has been manually adjusted). In some embodiments, IGRIS may include an indicator (e.g., on the user interface, or a physical indicator such as an LED) of the mode status (e.g., current mode, a change in mode, conflicts, etc.). For example, in the case of a conflict in input (e.g., both manual adjustment of the robotic manipulator and input on the user interface is received at relatively the same time), IGRIS shall provide an indication that there is a conflict in input.

Intelligent Targeting Backdrive

Intelligent Targeting Backdrive allows a user to adjust the pose of the instrument guide and/or the robotic manipulator manually. Intelligent Targeting Backdrive may operate in a similar manner as Basic Targeting Backdrive. For example, a user may manually orient the robotic manipulator and/or the instrument guide to prepare for a medical procedure, such as inserting a needle into a specific region of the human body. In response to the adjustment of the pose(s), IGRIS updates the graphical overlays in real-time to denote the desired trajectory (or path) of an instrument (e.g., needle) being inserted using the instrument guide.

In some embodiments the robotic manipulator may be constrained to be backdriven in restricted degrees of freedom. Free backdriving allows for arbitrary motion of the robotic manipulator and instrument guide in six degrees of freedom. During constrained backdriving, the instrument guide may be constrained to always point at a target location defined in a previous intelligent targeting step, and denoted by the first graphical overlay. In this manner, the user may position the location of the instrument guide to define the insertion location and distance from the patient skin, while maintaining accurate targeting of the desired image location. This constrained motion may be calculated by the haptic rendering 138. Other embodiments may constrain the insertion location allowing for the adjustment of the target location.

Intelligent Targeting Backdrive Flow

Intelligent Targeting Backdrive may operate according to the following steps and may be performed using IGRIS 100. In some embodiments, certain steps of this flow may be omitted.

Figure 13B:
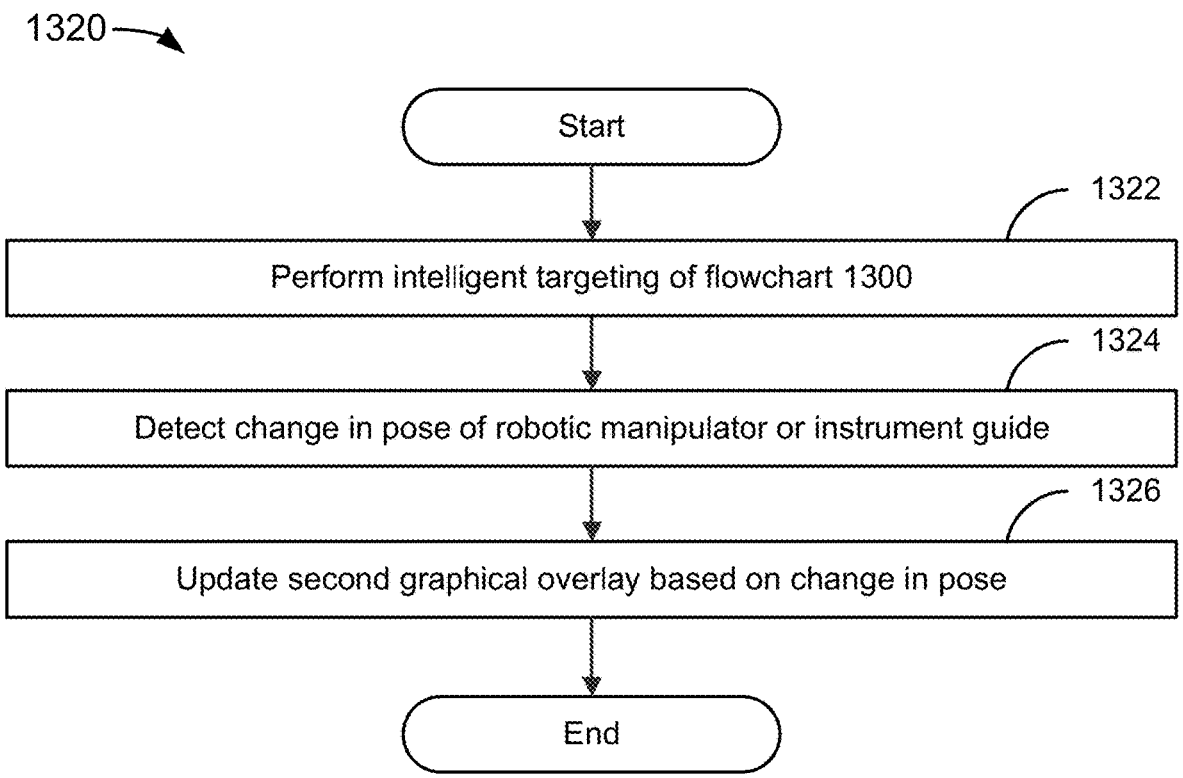

Referring to FIG. 13B, an embodiment of Intelligent Backdrive 1320 is disclosed.

In step 1322, IGRIS 100 performs the Intelligent Targeting flow 1300 described starting with the 1302 step.

In step 1324, IGRIS 100 may detect that the pose of Instrument Guide 128 or Robotic manipulator 126 has been changed. For example, a user may decide to manually adjust the Instrument Guide 128 or Manipulator 126. In response, IGRIS 100 may process the updated position information on the User Interface 132 to reflect the changes according to steps 1302-1310 of the Intelligent Targeting flow.

In step 1326, the second graphical overlay is updated on the 3D Reconstruction in real-time based on any adjustment of the pose of the Imaging Device 146, the Robotic manipulator 126, and the Instrument Guide 128. The graphical overlay may utilize different colors, shapes, or thicknesses to distinguish each overlay.

Intelligent Targeting Tap to Target

Similar to Basic Targeting Tap to target, Intelligent Targeting Tap to Target allows a user to automatically adjust the pose of the instrument guide and/or robotic arm using an input device (e.g., touch screen, mouse, keyboard, joy stick, track ball, etc.) coupled to the computer to select, or "tap," an area of interest on the user interface displaying the real-time images and the 3D Reconstruction of the object. Where in basic targeting, the user was tapping on pixels corresponding to static locations to target under the probe, intelligent targeting allows the user to tap pixels corresponding to the object or anatomy to target. In response, the instrument guide and/or robotic arm are automatically repositioned such that the instrument guide path is directed to the "tapped" object of interest. For example, the display may be coupled to a touch screen on the user interface where a user may "touch" the pixel on the screen denoting the location of the object to place a needle tip. In response, the pose of the instrument guide and/or robotic arm, and the graphical overlays, are automatically adjusted to reflect the desired positioning, and are updated in real time via localization to keep the instrument guide pointed at the object or anatomy.

Intelligent Targeting Tap to Target Flow

Intelligent Targeting Tap to Target may operate according to the following steps and may be performed using IGRIS 100. In some embodiments, certain steps of this flow may be omitted.

Figure 13C:
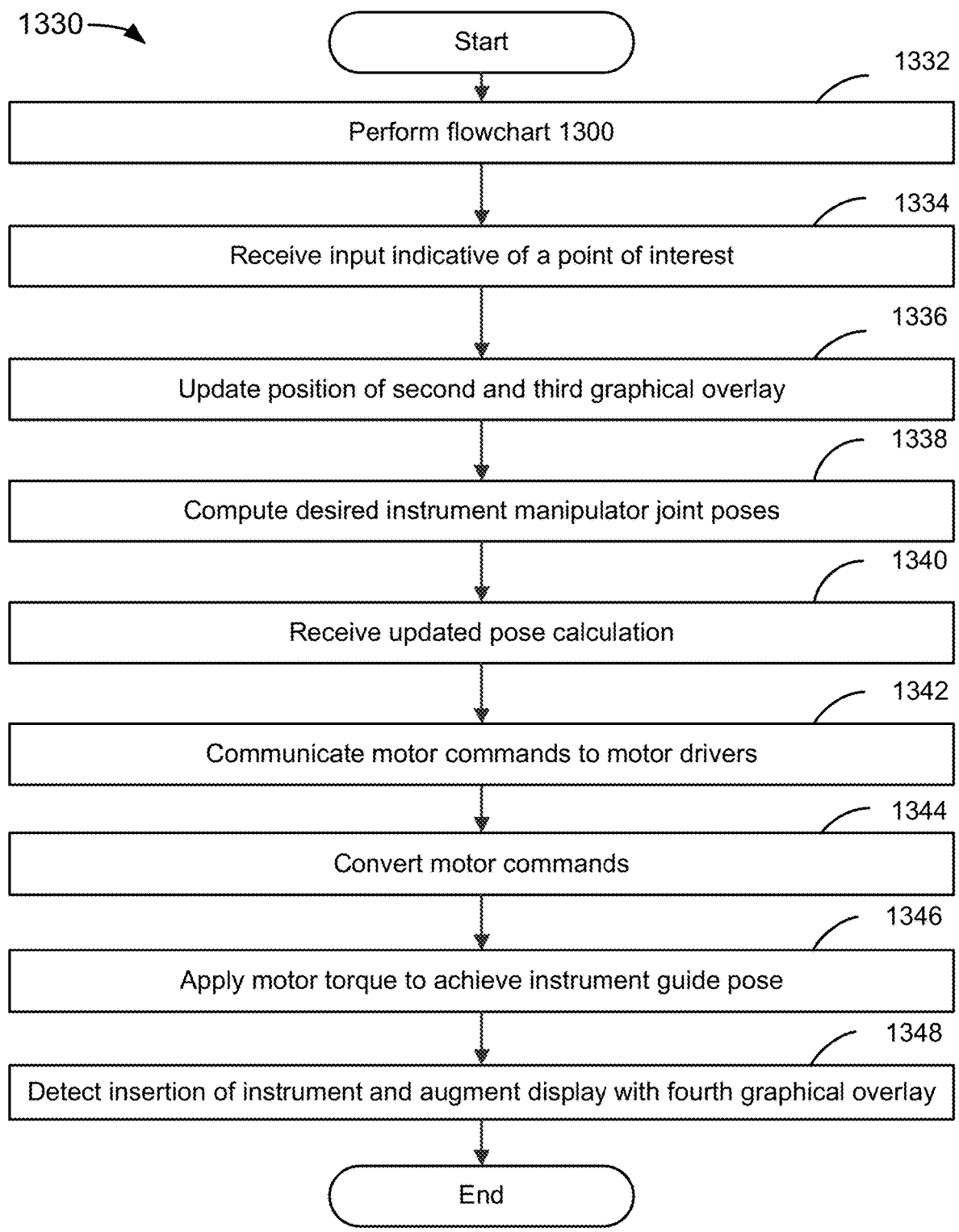

Referring to FIG. 13C, an embodiment of Intelligent Tap to Target 1330 is disclosed.

In step 1332, IGRIS 100 performs the Intelligent Targeting flow 1300 described starting with the 1302 step.

In step 1334, IGRIS 100 may receive an input indicating a point of interest from Display Unit 116, where the input may be a touch. For example, a user may select, or tap, a particular pixel of the 3D Reconstruction denoting the object representing the desired target point for a needle. In some embodiments, the user may also select a location on the live real-time image if during active localization. In an alternative embodiment, step 1334 may receive an input indicating a desired movement of the second graphical overlay (e.g., e.g., desired target for final location of the instrument tip). For example, a user may adjust the position or orientation of the Instrument Guide 128 by moving or dragging the orientation of the second graphical overlay. The second graphical overlay may be adjusted in different manners, such as directionally (e.g., up, down, left, right) or rotationally (e.g., clockwise, counter-clockwise). In some embodiments, alternative input devices to the Display Unit 116 may be utilized (e.g., mouse, keyboard, joy stick, track ball, etc.) to receive the input.

In step 1336, User Interface 132 may update the position of the second graphical overlay and third graphical overlay based on the received input. For example, User Interface 132 may adjust the position of the second graphical overlay to point to the desired target point for the needle and adjust the position of the third graphical overlay update the desired trajectory of the instrument inserted via instrument guide 128.

In step 1338, Trajectory Planner 136 may calculate an updated desired trajectory for the Robotic manipulator 126 and Instrument Guide 128 based on the received input and the current pose of the robot relative to the reconstruction provided by localization. In other words, IGRIS 100 will calculate an updated pose and move the Robotic manipulator 126 and Instrument Guide 128 based on the received input from step 1334 and localization to point the instrument guide at the target object.

The calculation to determine the new pixel location may be performed based on a number of ways, including the pixel location of the previous position of the second graphical overlay relative to the new pixel location, the absolute pixel location along the X-Y axis plane, the pixel location along the X-Y axis plane relative to the Imaging Device 146, or any calculation that may be understood by one of ordinary skill in the art.

In step 1340, Closed Loop Control 144 receives the updated pose calculations and related information from Trajectory Planner 136 to compute the motor commands to move Motors 122, Robotic manipulator 126, and Instrument Guide 128 to the desired pose.

Haptic Rendering 138 comprise other reference geometries and associated control laws that the Closed Loop Control 144 uses to guide the user in a collaborative manner. Haptic displays such as walls, springs, dampers, repulsive fields (opposite of spring), masses etc. This is useful to guide the HCP to adjust the interventional plan, enforce boundaries to prevent the user from inadvertently hitting objects that should be avoided or inserting an instrument tip beyond an intended target.

Kinematics 142 measures the current state of the mechanism joints (e.g., Motors 122, Robotic manipulator 126, Instrument Guide 128) and computes the instantaneous position (and velocity) of the Instrument Guide 128.

In some embodiments, Closed Loop Control 144 uses the outputs of the Trajectory Planner 136 and Haptic Renderer 138, and compares those to an estimate of the state of the Instrument Guide 128 coming from the Dead Reckoning 140 and Kinematics 142 to compute motor commands. This results in trajectory following, haptic display, and active compensation of the user's hand motion to keep the needle guide stable despite rotations and small translations of the device ("inertial disturbance rejection").

In step 1342, Closed Loop Control 144 communicates the computed motor commands to Motors Drivers 124. In some embodiments, Kinematics 142 may instead communicate the computed motor commands to Motor Drivers 124 based on the updated pose calculations from Trajectory Planner 136.

In step 1344, Motor Drivers 124 converts the computed motor commands into current to adjust the torque applied by the motors.

In step 1346, the pose of Robotic manipulator 126, and Instrument Guide 128 are adjusted to the indicated point of interest based on the joint trajectory commands from the trajectory planner.

In step 1348, IGRIS 100 may detect that an instrument (e.g., needle) has been inserted into the object via Instrument Guide 128 and in response, User Interface 132 may augment the real-time images on the user interface with a fourth graphical overlay that represents the depth of the instrument inserted into the object. In some embodiments, IGRIS 100 may determine the instrument depth by measuring the instrument movement through Instrument Guide 128. In other embodiments, IGRIS 100 may determine the instrument depth by performing an image analysis on the real-time images to detect the instrument in the image. In other embodiments, IGRIS 100 may utilize multiple instrument depth determinations, including those disclosed herein, or as understood by one of skill in the art.

Instrument Insertion

Once IGRIS is in position for instrument insertion, possibly via the Basic Targeting and Intelligent Targeting flows, IGRIS may prepare for insertion of the instrument into the object (e.g., patient anatomy).

In some embodiments, instrument insertion may be performed by the user manually inserting the instrument through the Instrument Guide into the object. For example, the HCP may manually press the instrument into the object via the instrument guide with the assistance of the User Interface and graphical overlays. The instrument guide may comprise a tube to constrain the instrument motion axially as inserted.

In some embodiments, instrument insertion may be performed by the user inserting the instrument through the Instrument Guide into the object with assistance from sensing modalities, such as a depth estimation rail, measuring rollers, or even a needle with fiducials which may be used as a reference for instrument insertion depth. For example, IGRIS may include sensing mechanisms that measuring the depth of a needle inserted through the instrument guide into the body.

In some embodiments, instrument insertion may be performed by IGRIS automatically using active rails to insert the instrument into the body. For example, Instrument Guide may comprise a robotically actuated insertion rail capable of inserting the instrument or needle through the instrument guide.

In some embodiments, instrument insertion may be performed by IGRIS automatically using grips (or locks) and an arm to insert the needle in robotically. In some embodiments the insertion arm is the instrument manipulator itself. For example, the instrument guide may grip the needle and/or instrument, and drive the needle to the target my commanding the instrument manipulator to move the instrument guide along an insertion trajectory parallel to the axis of the needle.

During instrument insertion, the User Interface display and graphical overlays are updated accordingly to display the instrument (e.g., needle) insertion into the object (e.g., anatomy). Aspects of the robotic and mechanical aspects of the instrument insertion mechanisms are described in further detail in the "Modular Robotic Arm" and "Instrument Guide" sections above.

Locking features may also allow a robotic manipulator with "last mile" placement of the instrument tip. For example, when piercing a vessel, the robotic arm may follow the instrument freely along the insertion axis. With an inclusion of haptic functionality, a haptic wall may be created such that when the instrument approaches the far side of the vessel, the user may be kept from piercing through the far side and exiting the vessel.

Locking features may also allow a robotic manipulator to perform fully autonomous targeting and insertion of the instrument. For the purpose of illustration and not of limitation, when piercing a vessel, a robotic manipulator may grab an instrument and actively drive the needle to the appropriate depth to place the instrument inside of the vessel. This modality can be applicable to any and all instrument insertion tasks including, but not limited to, injections, aspirations, ablations, biopsies, and/or cannulation.

Furthermore, IGRIS may include instrument deflection compensation techniques to detect any deflection of the instrument tip from the desired trajectory and can be actively adjusted to track to the target along the desired approach path. For example, a needle inserted into human anatomy may experience slight deflection due to various reasons, such as skin thickness, needle flexibility, etc. In some embodiments, IGRIS may detect the instrument (including the instrument tip) inserted into the anatomy via the real-time images from Imaging Device, and determine that the instrument has veered off its desired trajectory. For example, IGRIS may detect the curvature of the needle shaft has reached a level sufficient to cause the needle to veer off target. IGRIS may perform deflection compensation techniques to adjust the instrument trajectory back on course, including and not limited to, performing a calculation to compute the difference between the desired trajectory and the actual instrument location, and perform a proportional robotic adjustment to bring the instrument back on course.

The foregoing description of the preferred embodiments of the present invention is by way of example only, and other variations and modifications of the above-described embodiments and methods are possible in light of the foregoing teaching. The various embodiments set forth herein may be implemented utilizing hardware, software, or any desired combination thereof. For that matter, any type of logic may be utilized which is capable of implementing the various functionality set forth herein. Components may be implemented using a programmed general purpose digital computer, using application specific integrated circuits, or using a network of interconnected conventional components and circuits. Connections may be wired, wireless, modem, etc. The embodiments described herein are not intended to be exhaustive or limiting.

What is claimed is:
1. A system, comprising:
 a modular robotic arm, comprising:
  a robotic manipulator; and
  an instrument guide coupled to the robotic manipulator;
 a processing unit, comprising:
  at least one processor coupled to the modular robotic arm; and
  memory storing instructions that when executed by the at least one processor cause the system to:
   receive, from an imaging device coupled to the modular robotic arm, a plurality of real-time images of an object;
   receive, from the modular robotic arm, sensor and positional information of the robotic manipulator;
   receive, from the modular robotic arm, sensor and positional information of the instrument guide;

display, on a user interface coupled to the processing unit, the plurality of real-time images of the object;
augment the real-time images with a first graphical overlay, the first graphical overlay representing a desired trajectory of the instrument guide, wherein the desired trajectory indicates the path of an instrument inserted into the object using the instrument guide; and
perform a calibration, the calibration comprising:
receiving, from the imaging device, a plurality of desired settings of the imaging device;
receiving, from the imaging device, a plurality of real-time images of a known object, the known object comprising one or more embedded objects;
performing an image registration function, the image registration function comprising mapping the location of the real-time images of the known object to an X-Y pixel coordinate system, the mapping including mapping the location of the one or more embedded objects;
performing a scale function to determine a scale value based on the pixel location of the one or more embedded objects;
performing a scale transformation function based on the scale function; and
calculate, based on the scale transformation function, a calibration score.

2. The system of claim 1, the processing unit further to:
detect a change in pose of the robotic manipulator or instrument guide;
update the first graphical overlay based on the detection.

3. The system of claim 1, the processing unit further to:
receive, from an input device coupled to the processing unit, an input indicating a point of interest of the object on the user interface;
update the position of the first graphical overlay based on the received input;
calculate an updated desired trajectory of the modular robotic arm based on the received input;
update the pose of the modular robotic arm to match the desired trajectory based on the calculation.

4. The system of claim 1, wherein the instrument guide may be detachable.

5. The system of claim 1, wherein the instrument guide may comprise a sterile barrier encompassing the instrument guide.

6. The system of claim 1, wherein the modular robotic arm may comprise a sterile barrier encompassing the modular robotic arm.

7. A method, comprising:
receiving, from an imaging device coupled to a modular robotic arm, a plurality of real-time images of an object;
receiving, from the modular robotic arm coupled to the computer, sensor and positional information of the robotic manipulator, the modular robotic arm comprising a robotic manipulator and an instrument guide;
receiving, from the modular robotic arm, sensor and positional information of the instrument guide;
displaying, on a user interface coupled to the processing unit, the plurality of real-time images of the object;
augmenting the real-time images with a first graphical overlay, the first graphical overlay representing a desired trajectory of the instrument guide, wherein the desired trajectory indicates the path of an instrument inserted into the object using the instrument guide; and
performing a calibration, the calibration comprising:
receiving, from the imaging device, a plurality of desired settings of the imaging device;
receiving, from the imaging device, a plurality of real-time images of a known object, the known object comprising one or more embedded objects;
performing an image registration function, the image registration function comprising mapping the location of the real-time images of the known object to an X-Y pixel coordinate system, the mapping including mapping the location of the one or more embedded objects;
performing a scale function to determine a scale value based on the pixel location of the one or more embedded objects;
performing a scale transformation function based on the scale function; and
calculate, based on the scale transformation function, a calibration score.

8. The method of claim 7, further:
detecting a change in pose of the robotic manipulator or instrument guide;
updating the first graphical overlay based on the detection.

9. The method of claim 7, further:
receiving, from an input device coupled to the processing unit, an input indicating a point of interest of the object on the user interface;
updating the position of the first graphical overlay based on the received input;
calculating an updated desired trajectory of the modular robotic arm based on the received input;
updating the pose of the modular robotic arm to match the desired trajectory based on the calculation.

10. The method of claim 7, wherein the instrument guide may be detachable.

11. The method of claim 7, wherein the instrument guide may comprise a sterile barrier encompassing the instrument guide.

12. The method of claim 7, wherein the modular robotic arm may comprise a sterile barrier encompassing the modular robotic arm.

13. A non-transitory computer readable storage media comprising instructions, the instructions executable by a processor to perform a method, the method comprising:
receiving, from an imaging device coupled to a modular robotic arm, a plurality of real-time images of an object;
receiving, from the modular robotic arm coupled to the computer, sensor and positional information of the robotic manipulator, the modular robotic arm comprising a robotic manipulator and an instrument guide;
receiving, from the modular robotic arm, sensor and positional information of the instrument guide;
displaying, on a user interface coupled to the processing unit, the plurality of real-time images of the object;
augmenting the real-time images with a first graphical overlay, the first graphical overlay representing a desired trajectory of the instrument guide, wherein the desired trajectory indicates the path of an instrument inserted into the object using the instrument guide; and
performing a calibration, the calibration comprising:
receiving, from the imaging device, a plurality of desired settings of the imaging device;

receiving, from the imaging device, a plurality of real-time images of a known object, the known object comprising one or more embedded objects;

performing an image registration function, the image registration function comprising mapping the location of the real-time images of the known object to an X-Y pixel coordinate system, the mapping including mapping the location of the one or more embedded objects;

performing a scale function to determine a scale value based on the pixel location of the one or more embedded objects;

performing a scale transformation function based on the scale function; and calculate, based on the scale transformation function, a calibration score.

14. The non-transitory computer readable storage media of claim 13, further:

detecting a change in pose of the robotic manipulator or instrument guide;

updating the first graphical overlay based on the detection.

15. The non-transitory computer readable storage media of claim 13, further:

receiving, from an input device coupled to the processing unit, an input indicating a point of interest of the object on the user interface;

updating the position of the first graphical overlay based on the received input;

calculating an updated desired trajectory of the modular robotic arm based on the received input;

updating the pose of the modular robotic arm to match the desired trajectory based on the calculation.

16. The non-transitory computer readable storage media of claim 13, wherein the instrument guide may be detachable.

17. The non-transitory computer readable storage media of claim 13, wherein the modular robotic arm may comprise a sterile barrier encompassing the modular robotic arm.

18. The system of claim 1, wherein the calibration score indicates the quality of the calibration.

19. The method of claim 7, wherein the calibration score indicates the quality of the calibration.

20. The non-transitory computer readable storage media of claim 13, wherein the calibration score indicates the quality of the calibration.

* * * * *